US010434492B2

United States Patent
Lu et al.

(10) Patent No.: US 10,434,492 B2
(45) Date of Patent: Oct. 8, 2019

(54) COMPOSITIONS AND METHODS FOR SOLID PHASE EXTRACTION OF LIPIDS

(75) Inventors: Xiaoning Lu, State College, PA (US); Olga I. Shimelis, State College, PA (US); Maochun M. Ye, State College, PA (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 475 days.

(21) Appl. No.: 12/785,160

(22) Filed: May 21, 2010

(65) Prior Publication Data

US 2010/0291688 A1 Nov. 18, 2010

Related U.S. Application Data

(63) Continuation-in-part of application No. 12/019,445, filed on Jan. 24, 2008.
(Continued)

(51) Int. Cl.
| | |
|---|---|
| *G01N 1/34* | (2006.01) |
| *B01J 20/02* | (2006.01) |
| *B01J 20/06* | (2006.01) |
| *B01J 20/10* | (2006.01) |
| *B01J 20/32* | (2006.01) |
| *G01N 30/60* | (2006.01) |
| *G01N 30/46* | (2006.01) |

(52) U.S. Cl.
CPC ......... *B01J 20/06* (2013.01); *B01J 20/0211* (2013.01); *B01J 20/103* (2013.01); *B01J 20/3204* (2013.01); *B01J 20/3219* (2013.01); *B01J 20/3236* (2013.01); *B01J 20/3244* (2013.01); *B01J 20/3265* (2013.01); *G01N 30/6091* (2013.01); *G01N 30/466* (2013.01); *Y10T 436/107497* (2015.01)

(58) Field of Classification Search
CPC ...... B01J 20/06; B01J 20/103; B01J 20/3236; B01J 20/32; G01N 30/6091
USPC .............................. 436/17; 422/261; 502/402
See application file for complete search history.

(56) References Cited

U.S. PATENT DOCUMENTS

| | | |
|---|---|---|
| 5,919,909 A | 7/1999 | Josic et al. |
| 6,254,780 B1 | 7/2001 | Bouvier et al. |

(Continued)

FOREIGN PATENT DOCUMENTS

WO  2007090081 A2  8/2007

OTHER PUBLICATIONS

Office Action dated Jun. 21, 2012 for related U.S. Appl. No. 12/019,445; 11 pages.
(Continued)

*Primary Examiner* — Rebecca M Fritchman
(74) *Attorney, Agent, or Firm* — Kristin J. Frost

(57) ABSTRACT

A composition, method and device for the preparation of biological samples for subsequent instrumental analyses, such as GC, GC-MS, LC and LC-MS analysis, using a solid phase extraction (SPE) process is described. Through SPE process alone or an integrated combination of protein precipitation, filtration, and SPE using a hydrophobic zirconia-coated chromatographic media, interfering compounds, such as proteins, glycerides and phosphate-containing compounds, are eliminated from the biological, food, environmental and biotechnology samples, affording an enhanced analyte response during the instrumental analysis.

9 Claims, 34 Drawing Sheets

Related U.S. Application Data

(60) Provisional application No. 60/886,697, filed on Jan. 26, 2007.

(56) References Cited

U.S. PATENT DOCUMENTS

| | | | |
|---|---|---|---|
| 6,350,383 | B1 | 2/2002 | Douglas |
| 6,524,487 | B2 | 2/2003 | Kulperger et al. |
| 6,541,263 | B2 | 4/2003 | Gao |
| 6,846,432 | B2 | 1/2005 | Mills |
| 6,974,702 | B2 | 12/2005 | Dasseux et al. |
| 7,074,327 | B2 | 7/2006 | O'Connor et al. |
| 7,256,049 | B2 * | 8/2007 | Bennett et al. .......... 436/71 |
| 7,384,794 | B2 | 6/2008 | Pawliszyn |
| 7,402,243 | B2 * | 7/2008 | Liu et al. ............ 210/198.2 |
| 8,193,123 | B2 | 6/2012 | Rank et al. |
| 2004/0026324 | A1 | 2/2004 | Luca et al. |
| 2004/0126890 | A1 | 7/2004 | Gjerde et al. |
| 2004/0195182 | A1 | 10/2004 | Elliott |
| 2004/0235188 | A1 | 11/2004 | Soldin |
| 2005/0153297 | A1 | 7/2005 | Ahmad et al. |
| 2006/0216206 | A1 | 9/2006 | Hudson et al. |
| 2007/0090052 | A1 * | 4/2007 | Broske ............ B01J 20/286 210/656 |
| 2008/0213906 | A1 | 9/2008 | Aurand et al. |
| 2008/0287661 | A1 | 11/2008 | Jones |
| 2009/0062234 | A1 * | 3/2009 | Wilson ............ C08G 77/50 514/63 |

OTHER PUBLICATIONS

Mauer, "Advances in analytical toxicology: the current role of liquid chromatography-mass spectrometry in drug quantification in blood and oral fluid", Analytical and Bioanalytical Chemistry, 2005, vol. 381. pp. 110-118.

Patel et al., "Determination of total mycophenolic acid and its glucuronide metabolite using liquid chromatography with ultraviolet detection and unbound mycophenolic acid using tandem mass spectrometry", Journal of Chromatography B, 2004, vol. 813, pp. 287-294.

International Search Report for PCT/US07/61214, dated Sep. 11, 2007, 1 page.

Non-Final Office Action for U.S. Appl. No. 12/019,445, dated Jun. 17, 2009; 11 pages.

Non-Final Office Action for U.S. Appl. No. 12/019,445, dated Jan. 15, 2010; 10 pages.

Final Office Action for U.S. Appl. No. 12/019,445, dated Jul. 13, 2010; 9 pages.

Office Action in U.S. Appl. No. 12/019,445; dated Mar. 28, 2013 (8 Pages).

Notice of Allowance in U.S. Appl. No. 12/019,445; dated Aug. 26, 2013 (10 pages).

Office Action in U.S. Appl. No. 12/019,445; dated Jan. 16, 2014 (9 Pages).

Office Action related to U.S. Appl. No. 12/019,445, dated Jul. 28, 2015, 10 pages.

Non Final Office Action regarding U.S. Appl. No. 12/019,445 dated Oct. 16, 2014, 12 pages.

\* cited by examiner

Time (min)

Time (min)

COMPOSITIONS AND METHODS FOR SOLID PHASE EXTRACTION OF LIPIDS

CROSS REFERENCE TO RELATED APPLICATIONS

This application is a continuation-in-part of U.S. Non-Provisional application Ser. No. 12/019,445, filed on Jan. 24, 2008, which claims the benefit of U.S. Provisional Patent Application No. 60/886,697, filed Jan. 26, 2007, the contents of which are incorporated herein by reference in their entirety.

FIELD OF THE INVENTION

The present invention relates generally to a solid phase extraction stationary media. In particular, the present invention relates to solid phase extraction stationary media that includes a transition metal oxide and hydrophobic moiety bonded to a substrate.

BACKGROUND OF THE INVENTION

Lipids are a family of naturally occurring amphiphilic small molecules. Representative examples of lipids include fats, waxes, sterols, fat-soluble vitamins (such as vitamins A, D, E and K), monoglycerides, diglycerides, and phospholipids. The removal or capture of lipids from within various compositions finds application in a broad range of fields including food processing, medicine development, and chemical analysis.

Within each field, a variety of existing methods for capturing or removing lipids from a composition may be used depending on the particular composition, including thermal rendering, skimming, supercritical fluid extraction, solvent extraction, liquid-liquid extraction (LLE), and solid phase extraction (SPE). Depending on the intended use for the particular composition, a number of constraints on the method of lipid extraction and choice of reagents selected to carry out the lipid removal may be considered. Thermal rendering and skimming are economical methods of removing lipids from a composition, but these non-specific removal methods may unintentionally eliminate desirable non-lipid compounds from the composition, or the high temperatures of these methods may alter or damage the remaining compounds in the composition. Supercritical fluid extraction may also have similar disadvantages such as the non-specific extraction of lipid compounds as well as potentially damaging process conditions. Solvent extraction and liquid-liquid extraction are more selective lipid removal methods that may have less adverse effects on other compounds in the composition, but may also produce large volumes of solvent waste. SPE is another existing method of selectively removing lipids from a sample with minimal adverse effects on other compounds in the composition, while generating significantly lower amounts of waste solvents and other waste reagents compared to solvent extraction or liquid-liquid extraction methods.

SPE methods are based on contacting the composition with a solid phase adsorbent that has a selective affinity for lipids, and then separating the remaining lipid-free composition from the adsorbent. The adsorbent compositions used to immobilize the lipids in existing SPE methods are typically one of two types. The first adsorbent composition, typically used for immobilizing the phospholipid subset of the lipids includes a transition metal oxide such as titania, ceria, or zirconia, as described in US published application US2008/0213906, the contents of which are hereby incorporated by reference in entirety. A second type of adsorbent composition currently used for the capture or removal of lipids such as triglycerides include hydrophobic alkyl moieties or hydrophobic filtration materials such as PVDF membranes or frits.

The SPE compositions currently used for lipid removal have proven to be ineffective at removing more than a limited subset of the lipids, due to the wide range of chemical characteristics of the various lipid types. The transition metal oxide moieties of the first type of adsorbent composition are effective at binding polar moieties of certain lipids such as the phosphate groups of single-chain phospholipids, but are less effective at binding lipids with a higher proportion of nonpolar moieties such as the dual-chain phospholipids that include two nonpolar long-chain hydrocarbon moieties. The hydrophobic alkyl moieties of the second adsorbent composition type are effective at binding lipids possessing larger proportions of nonpolar long chain alkyls such as triglycerides, but are less effective at binding monoglycerides, which have a lower proportion of nonpolar alkyl chains.

A need exists for an SPE media composition that is effective at selectively capturing a wide range of lipid types that may include polar and nonpolar moieties in various proportions from a sample that may also contain other compounds such as target analytes that are of interest to the pharmaceutical sciences, environmental testing, and food science. In addition, a need exists for an SPE media composition that captures a wide range of lipid types in a sample that may contain additional compounds such as protein precipitation agents that may influence the chemical properties of the sample. Further, a need exists for an SPE media composition that is effective at selectively capturing a wide range of lipid types without capturing a variety of acidic, nonacidic and neutral target analytes.

SUMMARY OF THE INVENTION

The present disclosure provides compositions, devices, and methods used to perform solid phase extraction (SPE) to remove lipids from various samples. The SPE may be performed either alone or in combination with a protein precipitation process used to remove proteins from the samples. By combining the two techniques, the benefits of each technological platform are realized while minimizing their respective shortcomings. In general, the method combines the generic simplicity of protein precipitation with the selectivity benefits inherent with solid phase extraction. Unlike existing SPE methods that selectively retain the analyte of interest, followed by subsequent wash steps to induce the elution of the analyte, the SPE chromatographic media of the present disclosure retain or chemically filter out key endogenous sample interferences common in biological, food, environmental and biotechnology samples. These interfering molecules are particularly problematic in subsequent instrumental analyses, such as LC, LC-MS, GC and GC-MS analysis due to confounding effects induced by the molecules such as ion-suppression, low sensitivity, high background, low recovery. Some of the major interfering molecules in pharmaceutical bioanalysis include, but are not limited to, phospholipids and polyethylene glycol.

In one aspect, the present disclosure provides a solid phase extraction (SPE) media for selective removal of lipids from a sample is provided that includes a substrate, a hydrophobic linker compound bonded to the substrate at an attached end, and a metal oxide. The metal oxide may include a transition metal oxide, ceria, or any combination of a transition metal and ceria.

In another aspect, the present disclosure provides a solid phase extraction (SPE) media for selective removal of lipids from a sample that includes a mixture of a first particle and a second particle. The first particle includes a metal oxide bonded to a first substrate, where the metal oxide may be a transition metal oxide, ceria, or any combination of a transition metal oxide and ceria. The second particle includes a free hydrophobic compound bonded to a second substrate at a bound end.

In another aspect, the present disclosure also provides a solid phase extraction (SPE) media for selective removal of lipids from a sample that includes a porous silica substrate with any one or more of a particle size ranging from about 10 nm to about 1000 μm, a pore size ranging from about 30 Å to about 1000 Å, and a surface area ranging from about 5 $m^2$/g to about 1000 $m^2$/g. In addition, the SPE media includes a hydrophobic alkyl that includes a bound end bonded to the substrate and an unbound end opposite the bound end. The alkyl may range from C3 to C18 in length. The SPE media further includes zirconia bonded to the porous silica substrate.

In yet another aspect, the present disclosure also provides a solid phase extraction (SPE) media for selective removal of lipids from a sample that includes a porous silica substrate having any one or more of a particle size ranging from about 10 nm to about 1000 μm, a pore size ranging from about 30 Å to about 1000 Å, and a surface area ranging from about 5 $m^2$/g to about 1000 $m^2$/g. The SPE media also includes a hydrophobic alkyl linker that includes an attached end bonded to the substrate and a free end opposite the attached end as well as zirconia coupled to the free end of the hydrophobic alkyl linker. The alkyl ranges from C3 to C18 in length.

In a further aspect, the present disclosure provides a solid phase extraction (SPE) media for selective removal of lipids from a sample, including a mixture of a first particle that includes zirconia bonded to a porous silica substrate, and a second particle comprising a hydrophobic alkyl compound ranging from C3-C18. Both the first and second porous silica substrates have any one or more of a particle size ranging from about 10 nm to about 1000 μm, a pore size ranging from about 30 Å to about 1000 Å, and a surface area ranging from about 5 m2/g to about 1000 m2/g.

A method of producing an SPE media that includes a hydrophobic alkyl linker bound to a substrate at an attached end and bound at a free end opposite to the attached end to a metal oxide that includes a transition metal oxide, ceria, or any combination thereof, is also provided. The method includes drying the substrate to a constant weight and suspending the substrate in an organic solvent to form a suspension. In addition, the method includes contacting the suspension with the hydrophobic alkyl linker to form a coated substrate that includes the hydrophobic alkyl linker bound to the substrate at the attached end. In addition, the method includes contacting a metal alkoxide with the coated substrate to form the SPE media.

In another aspect, the present disclosure also provides a method of producing an SPE media that includes a hydrophobic alkyl linker bound to a substrate at an attached end and bound at a free end opposite to the attached end to a metal oxide that may include a transition metal oxide, ceria, or any combination thereof. This method includes drying the substrate and suspending the substrate in an organic solvent to form a suspension. This method further includes contacting the suspension with a hydrophobic alkyl linker precursor to form a coated substrate made up of a hydrophobic alkyl coating bound to the substrate at the attached end and a reactive group at the end opposite to the attached end. This method further includes contacting a metal alkoxide with the coated substrate to form the SPE media.

Also provided is a method for producing an SPE media made up of a hydrophobic alkyl bonded to a substrate at an attached end and a metal oxide made up of a transition metal oxide, ceria, or any combination thereof bonded to the substrate. The method includes drying the substrate and suspending the substrate in an organic solvent to form a suspension. In addition, the method also includes contacting the suspension with a hydrophobic alkyl precursor to form a coated substrate made up of a hydrophobic alkyl bonded to the substrate at the attached end. Further, the method includes contacting a metal alkoxide with the coated substrate to form the SPE media.

In another aspect, the present disclosure also provides a method for the selective removal of lipids from a sample is provided. The method includes contacting the sample with an amount of a SPE media, which includes a substrate, a hydrophobic linker compound bonded to the substrate at an attached end, and a metal oxide that may include a transition metal oxide, ceria or any combination of a transitional metal oxide and ceria.

Also provided is a method for the selective removal of lipids from a sample which includes contacting the sample with an amount of a SPE media. The SPE mixture includes a mixture of a first particle that includes a metal oxide that includes a transition metal oxide, ceria, or any combination of the two, as well as a second particle that includes a hydrophobic linker compound bonded to a second substrate at an attached end.

In another aspect, the present disclosure also provides a device for the removal of lipids from a sample, which includes a container that may include a syringe barrel, a pipette tip, a test tube, a flask, or a well within a well plate. The container forms an internal volume and an amount of SPE media is situated within the internal volume. The SPE media includes a substrate, an alkyl linker, and a metal oxide that may include a transition metal oxide, ceria, or any combination of the two.

The simplicity and robustness of the SPE media compositions, methods, and devices described herein overcome many of the previous limitations of prior lipid removal techniques.

BRIEF DESCRIPTION OF THE DRAWINGS

FIG. 15A is an ion-trace of clonidine (m/z 230), FIG. 15B is an ion-trace of protryptiline (m/z 264), FIG. 15C is an ion-trace of clomipramine (m/z 315), FIG. 15D is an ion-trace of desmethyldiazepam (m/z 271), and FIG. 15E is an ion-trace of the phospholipids (m/z 184).

In FIG. 32A, the metal oxide is attached to the substrate via a hydrophobic linker compound. In FIG. 32B, both the metal oxide and the hydrophobic linker compound are bonded to the substrate. In FIG. 32C, the metal oxide and hydrophobic linker compound are bonded to separate substrates.

DETAILED DESCRIPTION OF THE INVENTION

A novel solid phase extraction (SPE) media, as described herein, can be used to selectively remove lipid compounds, such as phospholipids and glycerides, from a sample such as a biological sample, a food matrix, an environmental sample, or a sample from a biotechnological process. The SPE media includes a hydrophobic linker compound and a metal oxide such as a transition metal oxide or ceria. This SPE media composition overcomes many of the previous limitations by providing both the capability of binding non-polar lipid moieties such as long-chain hydrocarbon groups with the inclusion of the hydrophobic linker compound, as well as the ability to bind polar lipid moieties such as phosphate groups by the inclusion of the metal oxide in the same SPE composition.

Figure 32:
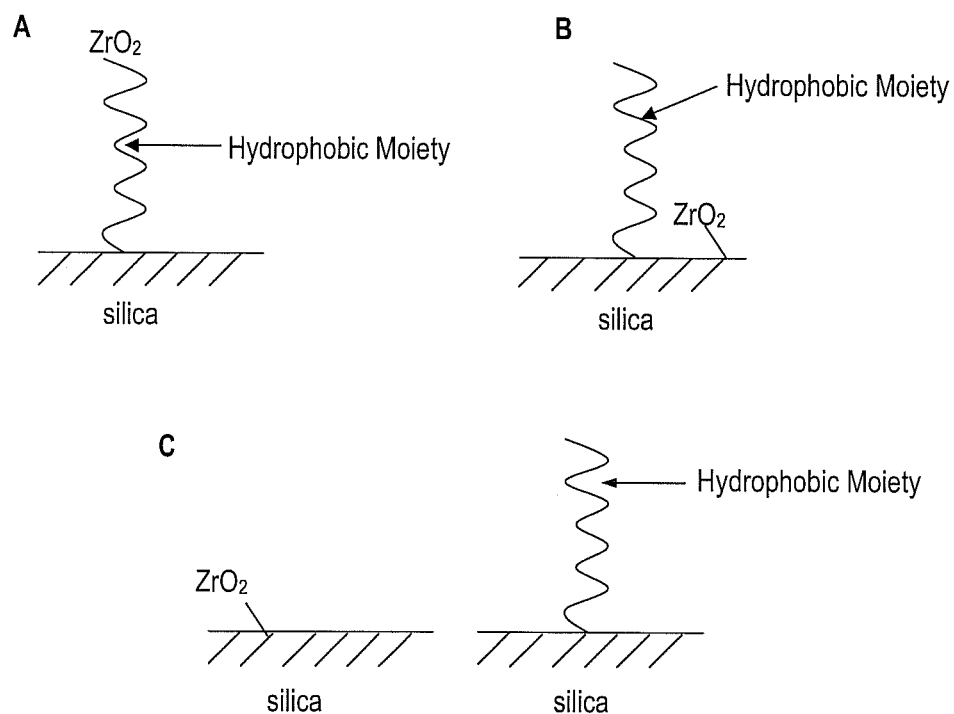
FIG. 32 is an illustration of three exemplary SPE media compositions.

The SPE media can include, for example, a hydrophobic linker compound such as a C3-C18 alkyl group with a free end coupled to a metal oxide such as zirconia and an attached end bonded to a substrate such as silica, as illustrated in FIG. 32A. The zirconia and hydrophobic linker may also both be bonded to the substrate, as illustrated in FIG. 32B. The SPE media may alternatively include a mixture of two particles in which the first particle includes zirconia bonded to the substrate and the second particle includes a hydrophobic compound such as a C3-C18 alkyl group bonded to a second substrate, as shown in FIG. 32C.

The hydrophobic linker compound and the metal oxide of the SPE media composition provide an affinity for the capture of a wide variety of the lipids in a sample. For example, the metal oxide may bind the phosphate group of a single-chain phospholipid, and the hydrophobic linker compound may bind to a long chain hydrocarbon tail of a triglyceride.

The substrates, hydrophobic linker compounds, and metal oxides included in various SPE compositions are described in detail below, as well as methods of producing the SPE media and devices for removing lipid compounds from a sample are described in detail below.

I) Samples

The SPE media are used for the selective removal of lipids from a sample. Non-limiting examples of a suitable sample includes a biological sample, a food matrix sample, an environmental sample, and a sample from a biotechnology process.

Non-limiting examples of biological samples from which lipids may be removed using the SPE media include any fluid samples collected from living or post-mortem eukaryotic organisms, including blood, urine, lymph, blood plasma, blood serum, bile fluid, cerebrospinal fluid, supernate from cell cultures, tissue extracts, or any combination thereof. Eukaryotic organisms, as defined herein, include any multicellular organism, including plants, animals, and fungi. Tissue samples may be centrifuged, desiccated and reconstituted, frozen and thawed, or otherwise treated using other known methods, prior to treatment using the method of the present disclosure.

A food matrix may be any food or feed suitable for human or animal consumption, and may include nutrients such as carbohydrates, fats, proteins, vitamins, minerals, soluble and insoluble fibers, preservatives, stabilizers, and any combination thereof. The food matrix may be in the form of a solid, semi-solid, or liquid form, although the solid and semi-solid forms may need to be suspended in a fluid solvent prior to lipid removal using the SPE media.

Environmental samples may include samples taken from natural or man-made bodies of water including oceans, lakes, streams, ponds, and reservoirs, from ground water, from industrial waste streams and runoff, from sewage streams, and from residential, commercial, and agricultural water supplies. Samples taken from a biotechnology process may include any fluid sample of an input to a process such as a culture medium or a mixture of reagents, a product such as a mixture or purified mixture containing one or more active pharmaceutical compounds, a mixture of by-products, and a mixture of waste products.

The sample may be a mixture of lipids, proteins, and other compounds including one or more target analytes that may include acidic analytes, non-acidic analytes, and neutral analytes. Further, if the sample is treated by the addition of other preconditioning compounds such as protein precipitation agents, the sample may also contain one or more preconditioning compounds.

a) Lipids

The lipids included in the sample to be removed by the SPE media may include one or more lipid compounds having a wide variety of chemical characteristics. Non-limiting examples of a lipid in the sample that is suitable for removal by the disclosed SPE media include a phospholipid, a glyceride, cholesterol, or any combination thereof. The phospholipids may include a single-chain phospholipid, a double-chain phospholipid, or any combination thereof. The glycerides may include a monoglyceride, a diglyceride, a triglyceride, or any combination thereof.

b) Target Analyte

The samples may further include at least one or more target analytes that are not captured by the SPE media. The particular species of target analyte included in the sample depends on at least one of several factors including the particular type of sample and the intended use of the sample. For example, if the sample is a blood sample and the intended use of the sample is to detect an amount of an active pharmaceutical compound in the blood sample, then the target analyte may be the active pharmaceutical compound. If the sample is an environmental sample, the target analyte may be a toxic compound or a dissolved mineral such as fluoride.

The target analytes may have any chemical structure or chemical property, and may be acidic, non-acidic, or neutral. Non-limiting examples of target analytes include active pharmaceutical compounds, environmental toxins, biologically active compounds such as peptides, hormones, and cytokines, and food components such as vitamins, minerals, carbohydrates, and proteins.

Non-limiting examples of active pharmaceutical compounds include m-toluamide, 4-hydroxy-3-methoxyphenylacetic acid, propazine, mirtazapine, benzoylecognine, linomycin, ritonavir, N-acetyl-L-cysteine, nalidixic acid, desipramine, benzylamine, dofetilide, 2-deoxyguanosine, mifepristone, benzanilide, nifedipine, quinapril, apigenin, corticosterone, folic acid, cytosine, imiquimod, nevirapine, simazine, estrone, venlafaxine, creatinine, 1-lysine, memantine, a-Methylbenzylamine, dapsone, prilocaine, desmethyldiazepam, diflucan (fluconazole), captopril, pyrimethamine, fenfluraime, dextromethorphan, xylazine, 2-deoxyadenosine, maprotiline, atrazine, mianserin, phenylbutazone, floxin (ofloxacin), niacinamide, clenbuterol, sulfadiazine, N-acetylprocainamide, promazine, 4-aminophenylacetic acid, trenbolone, tamoxifen, 5-fluorocytosine, 2-amino-3-phenyl-1-propanol, hippuric acid, sertraline, haloperidol, virginiamycin M1, vigabatrin, phenacetin (p-acetophenetidide), 4-decyloxybenzoic acid, clomipramine, fluoxetine, riboflavin, 5-aminosalicylic acid, xanthosine, mesoridazine, theobromine, clonidine, propanolol, ketoprofen, protryptiline, desmethyldiazepam, or any combination thereof. In addition, the target analytes may be active pharmaceutical compounds that are structurally, chemically, or functionally similar to the active pharmaceutical compounds listed above.

c) Other Compounds

The sample may include other compounds added to condition the sample prior to contacting the SPE media and removing the lipids in the sample. The sample may include added organic acids, protein precipitation agents, or any combination thereof.

An organic acid may be added to the sample to interfere with the binding of target analytes in the sample to the SPE media, thereby allowing the target analytes to contact the SPE media without being captured. Non-limiting examples of suitable organic acids include formic acid, acetic acid, citric acid, oxalic acid, maleic acid, malic acid, pyromellitic acid, or any combination thereof.

Protein precipitation agents may be added to sample, resulting in the precipitation of dissolved proteins, such as albumin, out of the sample. The protein precipitation agents may include salts, organic solvents, acids, or bases that alter the solubility of proteins in an aqueous solution, thereby causing the proteins to precipitate out of solution. Non-limiting examples of precipitation agents suitable for the sample preparation by protein precipitation include acetonitrile, formic acid, acetic acid, trichloroacetic acid, acetone, ethanol, hydrochloric acid, methanol, chloroform, ammonium sulfate, sodium citrate, sulfuric acid, polyethylene glycol, dextran, alginate, carboxymethycellulose, polyacrylic acid, tannic acid, polyphosphates, potassium chloride, ethanol, zinc chloride, t-butanol, or any combination thereof.

An organic acid and protein precipitating agent may be added to a sample in the form of solution containing the organic acid at a concentration of no more than about 5%, preferably between about 1% and about 2%, and most preferably about 1% by weight, dissolved in the protein precipitating agent. One example of an organic acid/protein precipitating agent solution is 1% formic acid in acetonitrile. The combined organic acid/protein precipitating agent solution may be added to the sample at a solution:sample volume ratio ranging between about 2:1 and about 5:1. Preferably, the combined organic acid/protein precipitating agent solution may be added to the sample at a solution:sample volume ratio of about 3:1.

II) SPE Media Composition

The SPE media for the selective removal of lipids from a sample can, for example, include a substrate, a hydrophobic linker compound bonded to the substrate at an attached end, and a metal oxide. The metal oxide may be coupled to the hydrophobic linker compound, as shown in FIG. 36A. Alternatively, the metal oxide may be bonded to the same substrate as the hydrophobic linker compound, as shown in FIG. 36B, or to a second substrate separate, as shown in FIG. 36C.

The substrate, hydrophobic linker compound, and metal oxide are described in detail below.

a) Substrate

In the SPE media, the substrate can provide a structural support to which the hydrophobic linker compound and optionally the metal oxide may be bonded. The substrate may be provided in any form, including a surface, a membrane, a filament, and a particle. In exemplary SPE media, the substrate is in the form of a porous particle or granule.

The substrate may be selected to possess chemical properties that allow for the covalent bonding of a hydrophobic linker compound, a metal oxide compound, or both a hydrophobic linker compound and a metal oxide compound.

Non-limiting examples of materials suitable for use as the substrate of the SPE media include porous silica, Immobilized Metal Affinity Chromatography (IMAC) materials, porous alumina, non-porous silica, non-porous alumina, carbon, zirconia, diatomaceous earth, controlled pore glass, porous polymers, and any combination thereof. Further, the substrate may be selected to enhance the surface area of the SPE media to enhance the capacity of the SPE media for the binding of lipids.

Exemplary SPE media include particulate and porous substrate materials, such as porous silica or porous alumina. The particle size of the substrate material, for example, may range between about 10 nm and about 1000 µm, or alternatively may range between about 5 µm and about 70 µm. The pore size of the substrate material can range between about 30 Å and about 1000 Å, or between about 60 Å and about 400 Å. The surface area of the substrate material may range between about 5 $m^2/g$ and about 1000 $m^2/g$, and more preferably between about 100 $m^2/g$ and about 600 $m^2/g$.

b) Metal Oxide

Exemplary SPE media include a metal oxide, which may include a transition metal oxide and ceria. These metal oxides exhibit a particularly selective affinity for polar moieties in lipids, including phosphate-containing compounds such as phospholipids. Non-limiting examples of transition metal oxides for the SPE media include zirconia, titania, or any combination thereof. The metal oxides may be chemically bonded to the substrate or the metal oxides may be coupled to a free end of the hydrophobic linker compound situated opposite to the end of the linker compound bonded to the substrate. Methods of bonding the metal oxide to the substrate and coupling the metal oxide to the hydrophobic linker compound are described in detail below.

c) Hydrophobic Linker Compounds

The SPE media may include a hydrophobic linker compound bonded to the substrate. The hydrophobic linker compound includes a free end that is situated opposite to an attached end that is bonded to the substrate. A single layer of hydrophobic linker compounds may be bonded to the substrate, or additional layers of hydrophobic linker compounds may be cross-linked to the free ends of bonded linker compounds to form multiple layers of cross-linked hydrophobic linker compounds.

The hydrophobic linker compound may be any alkyl group ranging from C3 to C18. Alternatively, the hydrophobic linker compound may be a C3 alkyl, a C4 alkyl, a C5 alkyl, a C6 alkyl, a C7 alkyl, a C8 alkyl, a C9 alkyl, a C10 alkyl, a C11 alkyl, a C12 alkyl, a C13 alkyl, a C14 alkyl, a C15 alkyl, a C16 alkyl, a C17 alkyl, a C18 alkyl, or any combination thereof. The hydrophobic alkyl linker may be any straight or branched alkyl group ranging from C3 to C18.

The chemical properties of the SPE media composition may be varied by the inclusion of a higher or lower proportion of hydrophobic linker compound relative to the amount of metal oxide. The proportion of hydrophobic linker compound may be increased using any one or more of at least several methods such as the inclusion of higher molecular weight alkyls as linker compounds, the use of multiple cross-linked layers of linker compounds, or any combination thereof. The amount of hydrophobic linker compound relative to the amount of metal oxide may be specified by variations in the process parameters and reagents used in the methods of producing the SPE media compositions, described in detail below.

III) Methods of Producing SPE Media

The present disclosure also encompasses a method of producing a SPE media for the selective removal of lipids from a sample. The SPE media are produced by bonding the hydrophobic linker compound to the substrate and then either bonding the metal oxide to the substrate or coupling the metal oxide to the free end of the linker compound. Overall, the steps of the process include drying the substrate to a constant weight, suspending the substrate in an organic solvent to form a suspension, contacting the suspension with the hydrophobic alkyl linker to form a coated substrate that includes the hydrophobic alkyl linker bound to the substrate at the attached end, and finally contacting a metal alkoxide with the coated substrate to form the SPE media. After the SPE media is formed, unused reactants and reaction byproducts are removed and the SPE media may be dried and stored in a humidity-controlled environment, such as a desiccator.

a) Step I—Drying the Substrate

In the initial step of the method of producing the SPE media, the substrate is dried to constant weight using known techniques, such as room temperature drying, oven drying, vacuum oven drying, azeotropic drying, or any combination thereof. An exemplary method of drying is conducted in a vacuum oven at a temperature ranging between about 30° C. and about 300° C. Another exemplary method of drying the substrate is drying in a vacuum oven at a temperature ranging between about 30° C. and about 300° C., followed by azeotropic drying using HPLC-grade toluene in a round bottom flask with a Dean Stark trap attached. During azeotropic drying, the substrate is added to the toluene in the round flask, the mixture is heated to a temperature ranging between about 100° C. and about 140° C., and then distillates from the flask are drained through the Dean Stark trap. This process of azeotropically drying the substrate may be repeated up to five times.

b) Step II—Suspend the Substrate in an Organic Solvent

The dried substrate may then be suspended in an organic solvent. For example, the organic solvent is an anhydrous solvent, resulting in anhydrous conditions for the subsequent reactions of the production method. The anhydrous conditions are particularly important because the metal alkoxides and the hydrophobic linker precursors may be unstable in water, and may polymerize in aqueous solution in a undesired manner.

Non-limiting examples of anhydrous organic solvents suitable for suspending the substrate include anhydrous toluene, 1,2-dichloroethane, 1-methyl-2-pyrrolidinone, acetonitrile, benzene, butyl ether, chloroform, dimethyl sulfoxide, ethyl acetate, heptane, isopropyl alcohol, methyl alcohol, methylene chloride, N,N-dimethylacetamide, N,N-dimethylformamide, p-dioxane, pentane, petroleum ether, pyridine, tetrahydrofuran, xylene, ethyl benzene, or any combination thereof. The substrate can be suspended, for example, in anhydrous toluene.

The suspension may be formed at room temperature or any other temperature well below the reflux temperature of the organic solvent. For example, the temperature of the suspension may be raised to above about 110° C. or above the reflux temperature of the organic solvent in order to distill away any residual water in the suspension. The suspension may be cooled to room temperature or any temperature well below the reflux temperature of the organic solvent prior to adding other reagents to the suspension in subsequent steps.

The mixture formed by the addition of the organic solvent to the dried substrate particles forms a suspension to which the alkyl linker precursors and metal alkoxides may be added in subsequent steps.

c) Step III—Contact Suspension with Hydrophobic Alkyl Linker Precursor

The suspension containing the substrate and organic solvent may then be contacted with a hydrophobic alkyl linker precursor to form a coated substrate comprising a hydrophobic alkyl coating bound to the substrate at the attached end and a reactive group at the end of the alkyl linker opposite to the attached end. As previously described, the hydrophobic linker compound may be an alkyl ranging from C3-C18. The hydrophobic alkyl precursor, for example, may be a compound that includes the alkyl group as well as reactive groups situated at opposite ends of the alkyl group. The reactive group at one end bonds to the substrate under the conditions of the reaction, and the second reactive group at the opposite end is available for either coupling to the metal oxide or for cross-linking with additional hydrophobic alkyl precursors.

Non-limiting examples of suitable hydrophobic alkyl linker precursors include 1,8-bis(trichlorylsilyl)octane, 1,18-bis(triclorylsilyl)octadecane, 1,4-bis(trichlorysilyl)butane, 1,3-bis(triclorylsilyl)propane, 1,8-bis(trimethoxysilyl)octane, 1,18-bis(trimethoxysilyl)octadecane, 1,4-bis(trimethoxysilyl)butane, 1,3-(trimethoxysilyl)propane, or any combination thereof.

The alkyl linker precursor may be added to the suspension slowly at room temperature over a period of time ranging from about 30 minutes to about two hours while stirring. Optionally, the vessel containing the suspension may be flushed with pure nitrogen prior to the addition of the alkyl linker precursor, and a slight nitrogen pressure maintain within the vessel for all subsequent steps of the production method.

In order to accelerate the bonding of the alkyl linker precursors to the substrate, the temperature of the reaction mixture that includes the suspension and the alkyl linker precursor may be raised to the reflux temperature of the organic solvent for a period ranging from about 12 hours to about 24 hours. For example, the temperature of the reaction mixture may be raised to about 110° C. for about 16 hours. After the completion of the reaction, the reaction mixture may be cooled down to room temperature.

The alkyl linkers may be cross-linked by the addition of a cross-linking agent to the reaction mixture at room temperature, and then heating the reaction mixture to a temperature ranging from about 50° C. to about 110° C. for a period ranging between about one hour and about twelve hours. Non-limiting examples of suitable cross-linking agents include water, a mixture of water and propanol (1:2 by volume), triethylamine, ptoluenesulfonic acid, or any combination thereof. The cross-linking agent may be added to the reaction mixture after the addition of the alkyl linker precursor, or just before the addition of the alkyl linker precursor.

The reaction mixture may be cooled to a temperature ranging between about 30° C. to about 70° C. and then filtered and rinsed with one or more rinse solvents in sequence. Non-limiting examples of suitable rinse solvents include toluene, methanol, water, and any combination thereof. The rinsed particles may then be dried in a vacuum oven at a temperature ranging from about 30° C. and about 300° C. before bonding the metal oxide to the particles.

Alternatively, the reaction mixture may be cooled to a temperature ranging between about 30° C. and about 70° C., and the reactants used to bond the metal oxide to the particles may be introduced to the reactant mixture directly.

The particles resulting from this step of the method include the substrate coated with an alkyl linker coating with reactive free ends. Non-limiting examples of alkyl linker coatings include (trichlorylsilyl)octane, (trichlorylsilyl)octadecane, (trichlorysilyl)butane, (trichlorylsilyl)propane, (trimethoxylsilyl)octane, (trimethoxysilyl)octadecane, (trimethoxysilyl)butane, (trimethoxysilyl)propane, or any combination thereof.

d) Step IV—Contact Hydrophobic Linker-Coated Particle with Metal Alkoxide

The resulting particle that includes the substrate coated with the hydrophobic linker compound may then contacted with a metal alkoxide in order to either couple the metal oxide to the free end of the alkyl linker compound, or to bond the metal oxide to the substrate.

A metal alkoxide, as defined herein, is a metal bonded to three or more negatively charged oxygen atoms from the conjugate bases of alcohols. The metal alkoxides may include a transition metal alkoxide, a ceria alkoxide, or any combination thereof. Non-limiting examples of metal alkoxides suitable for use in the bonding method of the present disclosure include zirconia butoxide, zirconia ethoxide, zirconia isopropoxide, zirconia methoxide, titania butoxide, titania ethoxide, titania isopropoxide, titania methoxide, ceria butoxide, ceria ethoxide, ceria isopropoxide, ceria methoxide, or any combination thereof. The metal alkoxide may be added a solution of the metal alkoxide in an alkanol such as propanol.

Exemplary transition metal alkoxides include zirconia butoxide, zirconia ethoxide, zirconia isopropoxide, and zirconia methoxide. A particularly exemplary transition metal alkoxide used in the production of the SPE media is zirconia isopropoxide.

The substrate coated with alkyl linkers may be provided in the form of a suspension in an organic solvent, as rinsed particles, or as dried particles. Rinsed particles or dried particles may be resuspended in an organic solvent such as toluene, and any residual water may be distilled out of the suspension by heating the suspension to a reflux temperature of about 110° C. for about one hour to about 16 hours. Prior to contacting the suspension to the metal alkoxide, the suspension may be cooled to a temperature ranging from about 30° C. to about 70° C.

The substrate coated with alkyl linkers resulting from the previous step is combined with the metal alkoxide under anhydrous conditions to avoid polymerization of the metal alkoxides. The metal alkoxide may be added to the suspension slowly over a period ranging from about 30 minutes to about two hours at about room temperature. The reaction mixture, that includes the suspension and the substrate, may be stirred at room temperature for a period of about one hour, and then heated to a reflux temperature of about 110° C. to maintain anhydrous conditions and stirred at that temperature for a period ranging between about 4 and about 24 hours. For example, the reaction mixture may be stirred at about 110° C. for a period ranging between about 8 hours and about 16 hours. The molar ratio of metal oxide:substrate in the reaction mixture may range between about 0.5 and about 3. During this time, the metal alkoxide reacts with the substrate or the free end of the alkyl linker compound, resulting in the bonding of the metal oxide to the substrate, or the coupling of the metal oxide to the free end of the alkyl linker compound.

e) Step V—Rinse and Dry SPE Media Particles

Once the bonding reaction has proceeded for a sufficient duration, the bonding reaction is halted by cooling the reaction mixture to a temperature below about 70° C. Any remaining solvents, excess reactants, and reaction by-products are separated from the SPE media that resulted from the bonding reaction by any known method including filtration. An exemplary filtration device suitable for filtering the SPE media particles out of the remaining liquid components of the reaction process is a sintered-glass Buchner funnel with a suitable pore size ranging between about 10 µm and about 100 µm.

After separating the SPE media particles from the solvents, excess reactants and reaction by-products, the SPE media may be rinsed using one or more rinse solvents sequentially. Non-limiting examples of suitable rinse solvents include toluene, water, methanol, dichloromethane, formic acid, or any combination thereof. After filtration and rinsing, the SPE media particles may be dried to constant mass using known methods. An exemplary method is drying in a vacuum oven at a temperature ranging between about 20° C. and about 150° C. After drying, the SPE media particles may be stored in a humidity-controlled environment such as a desiccator.

The SPE media particles may be used in a variety of devices and methods in order to contact the SPE media with the sample, and then to separate the SPE media and any captured lipids from the sample, resulting in the removal of the lipids from the sample.

IV) Method of Using the SPE Media

The SPE media may be used for the selective removal of lipids from a sample. The sample containing lipids is contacted with the SPE media, which binds to the lipids and removes them from the sample.

The SPE media may be contacted with the sample by any known method. The SPE media may be placed into a container and the sample may be trickled through the SPE media in the container. The sample may be mixed with the SEP media in the container using any known method including but not limited to shaking, agitating, stirring, or any combination thereof. Non-limiting examples of suitable containers include SPE cartridges, syringe barrels, pipette tips, test tubes, flasks, and wells within well plates. For example, the SPE media may be packed into an SPE cartridge between an upper PTFE frit with a nominal porosity of 5 µm and a lower 0.2 µm porosity filter.

The treated sample that is removed from the container after contacting the SPE media may then be analyzed using known analytical techniques in order to measure any target analytes that may also be present in the sample. Non-limiting examples of suitable analytical techniques include LC, HPLC-MS, GC, GC-MS, HPLC-ELSD, and HPLC-Fluorescence.

Figure 1:
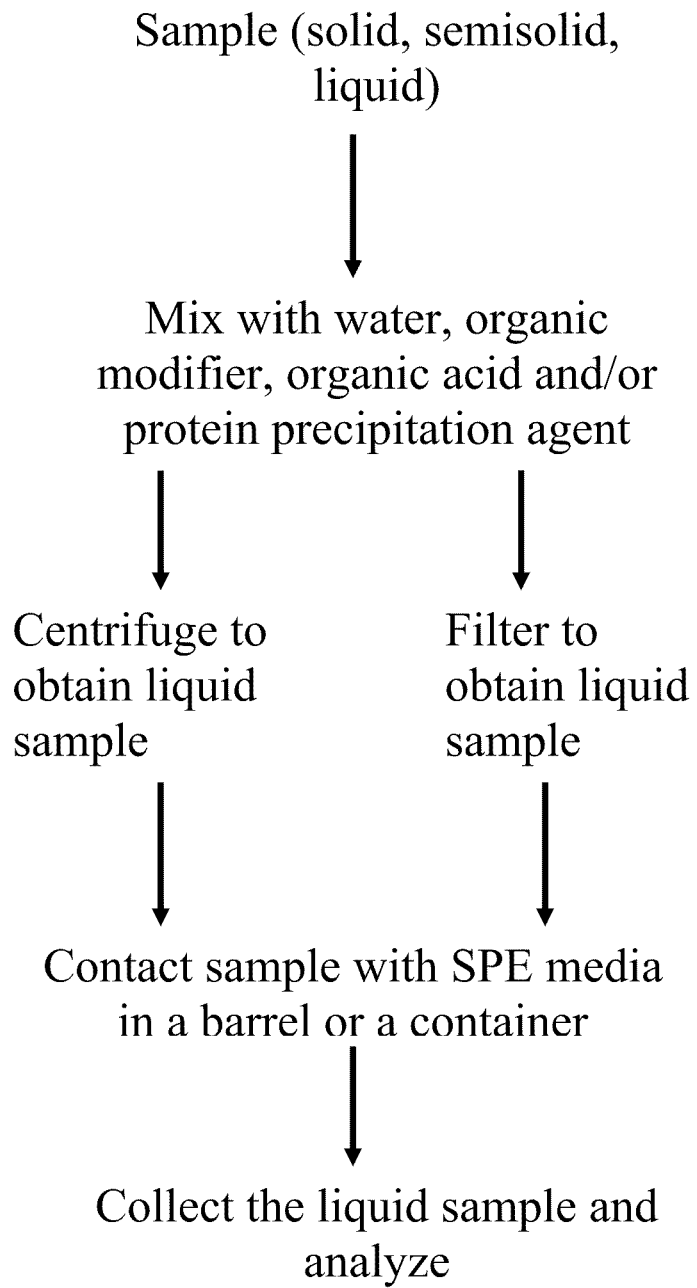
FIG. 1 is a flow chart of the method of the present disclosure.

The SPE media in an SPE cartridge between an upper and lower filter may be used to precondition a sample by a combined process of protein precipitation and SPE removal of lipids. A flow chart of this pre-conditioning process is presented in FIG. 1. The sample may be mixed with an organic acid and a protein precipitation agent and then introduced into the top of an SPE filter, first contacting an upper frit, which filters out the precipitated proteins that are suspended in the biological sample. The filtrate of the sample next contacts the SPE media, which preferentially binds any lipids, and allows any dissolved target analytes to pass through. The sample finally contacts the bottom filter, which filters out any remaining precipitated proteins or other particulate matter remaining in the sample. The eluate that emerges from the SPE cartridge may then be analyzed using any of the known analytical techniques described above.

In this method, proteins that are precipitated by the protein precipitation agent in the sample may be separated from the sample using any known methods including filtration, centrifugation, or any combination thereof. The sample may be centrifuged after contact with the protein precipitation agent, and the resulting supernate of the centrifuged sample may then be contacted with the SPE media. Alternatively, the sample may be filtered after the addition of the protein precipitation agent, and the filtered sample may be contacted with the SPE media.

If protein precipitation is not performed on the sample in conjunction with SPE, the contact with SPE media may also occur in a container, including but not limited to a flask or a test tube. The SPE media may be free-flowing to facilitate placement of the SPE media into the container. A liquid sample may be contacted with the SPE media within the container and mixed using known methods including but not limited to shaking and stirring. After thoroughly mixing, the liquid sample may be separated from the solid SPE media using known methods including but not limited to filtration or centrifugation.

V) Devices and Systems Using the SPE Media

The present disclosure further provides devices for the removal of lipids from a sample that include a container with an amount of SPE media situated within the internal volume of the container. The internal volume of the container may open to an inlet and to an exit at opposite ends, or the internal volume of the container may open to a single inlet used for the transfer of materials in and out of the internal volume.

In use, a sample is inserted into the internal volume and contacts the SPE media within the internal volume, resulting in a treated sample in which the lipids have been essentially removed from the sample. The sample may make intimate and extended contact with the SPE media by means of a number of known methods. The sample may contact the SPE media as it trickles from the inlet to the exit of a device such as a syringe barrel. The sample may move through the SPE media due to gravitational forces or by the application of pressure at the inlet, by the application of suction at the outlet, or any combination thereof. Alternatively, the sample may make intimate, extended contact with the SPE media by mixing the sample and SPE media using known methods including but not limited to shaking, agitating, stirring, and any combination thereof. The treated sample may be collected for subsequent use including analysis by LC or other analysis methods described previously.

Non-limiting examples of containers suitable for use in the disclosed device include syringe barrels (with or without plungers), pipette tips, SPE cartridges, tanks, vats, test tubes, flasks, and well plates. The syringe barrels and SPE cartridges may have volumes ranging between about 0.5 ml and about 60 ml. The test tubes may have volumes ranging between about 1 mL and about 50 mL, and the flasks may have volumes ranging from about 50 mL and about 500 mL. The 96-well plates may have headspace volume capacities ranging between about 0.5 mL and about 2 mL.

For example, if the container is a syringe barrel or a pipette tip, the sample may be contacted with the SPE media by aspirating the sample into the internal volume of the container through the inlet of the container, and then expelling the sample from the internal volume through the inlet. The sample may be aspirated and expelled in repeated cycles in order to increase the contact time between the SPE media and the sample.

Figure 2:
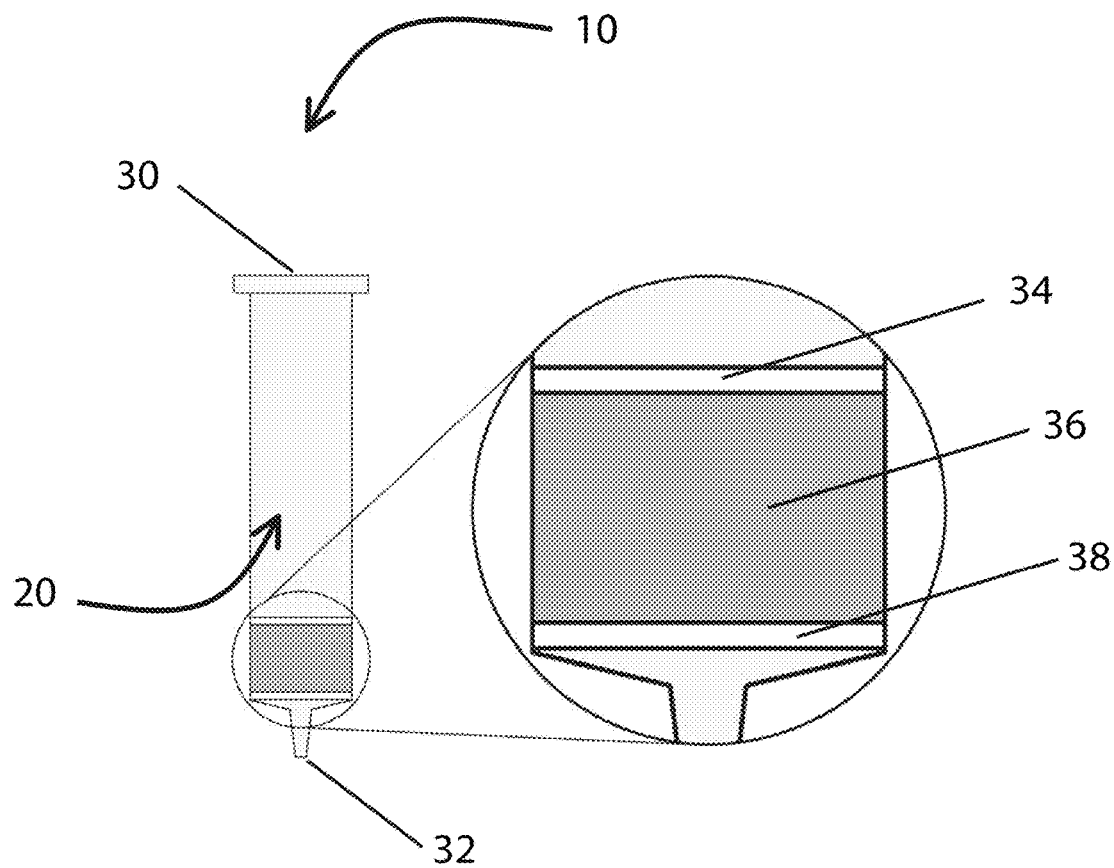
FIG. 2 shows the cartridge, filters and transition metal oxide components of the system of the present disclosure.

The SPE media may also be included in a system 10, shown in FIG. 2, for the selective removal of interfering components including lipids from a sample. The system includes a cartridge 20 having a cartridge entrance 30 and a cartridge exit 32, and having a volume ranging between about 0.5 ml and about 60 ml. Inside the cartridge 20 is a top filter 34 located near the cartridge entrance 30, and a bottom filter 38 located near the cartridge exit 32. The system 10 also includes a quantity of SPE media 36 packed inside of the cartridge 20 between the top filter 34 and the bottom filter 38.

The cartridge 20 used in the system 10 is preferably constructed from laboratory grade polypropylene, selected to avoid imparting foreign agents, such as plasticizers, phthalates, long chain hydrocarbons, or mold release agents, into the samples. The cartridges 20 may be any known container, including syringe barrels (without plunger) having volumes ranging between about 0.5 ml and about 60 ml, SPE cartridges with volumes ranging between about 0.5 ml and about 60 ml, and 96-well plates with headspace volume capacities ranging between about 0.5 ml and about 2 ml.

The upper filter 34 and lower filter 38 are either filters or frits possessing porosities ranging between about 0.1 µm and about 50 µm. Frits are defined herein as finely porous materials through which liquids may pass. More preferably, the upper filter 34 is a frit with a porosity ranging between about 5 µm and about 20 µm, and most preferably with a porosity of about 5 µm. The lower filter 38, more preferably, is a filter with a porosity ranging between about 0.1 µm and about 1 µm, and most preferably with a porosity of about 0.2 µm.

The upper filter 34 and lower filter 38 are constructed of materials including polypropylene, polyethylene (PE), polytetrafluoroethylene (PTFE), glass, or any combination thereof. PE is a common standard material that provides good aqueous wetting capability and chemical resistance. PTFE offers good chemical resistance and limited "sample leakage" when conducting protein precipitation within a well plate or a cartridge. Most preferably, the upper filter 34 is constructed from PTFE, and the lower filter 38 is constructed from PE.

The amount of SPE media 36 packed into each cartridges 20 ranges between about 20 mg and about 80 mg. Preferably, about 50 mg of SPE media 36 is packed into each cartridge 20.

During the use of the system 10, a biological sample is combined with an organic acid, such as formic acid, in solution with a protein precipitation agent, such as acetonitrile, and introduced into the cartridge entrance 30. The resulting precipitated proteins are filtered from the biological sample by the combined filtration of the upper filter 34, the lower filter 38, and the SPE media 36. Concurrently, lipids are preferentially bound to the SPE media 36. Target analytes, defined above, which have also have an affinity for the SPE media 36, may be prevented from binding to the SPE media 36 due to competitive interference and preferential retention of the organic acid, which possesses a stronger affinity for the SPE media 36 than the chromatographic media has for the target analytes. Rather than retaining target analytes for subsequent elution, as is a common practice in the art, the selective retention of lipids and the removal of precipitated proteins are conducted concurrently within the system 10. Typically, the resulting eluate containing the analytes of interest is ready to be immediately analyzed without further treatment using analytical methods described previously, such as LC-MS. In some instances, further sample treatment, such as evaporation and reconstitution, may be required or desired prior to analysis of the target analyte.

Figure 3:
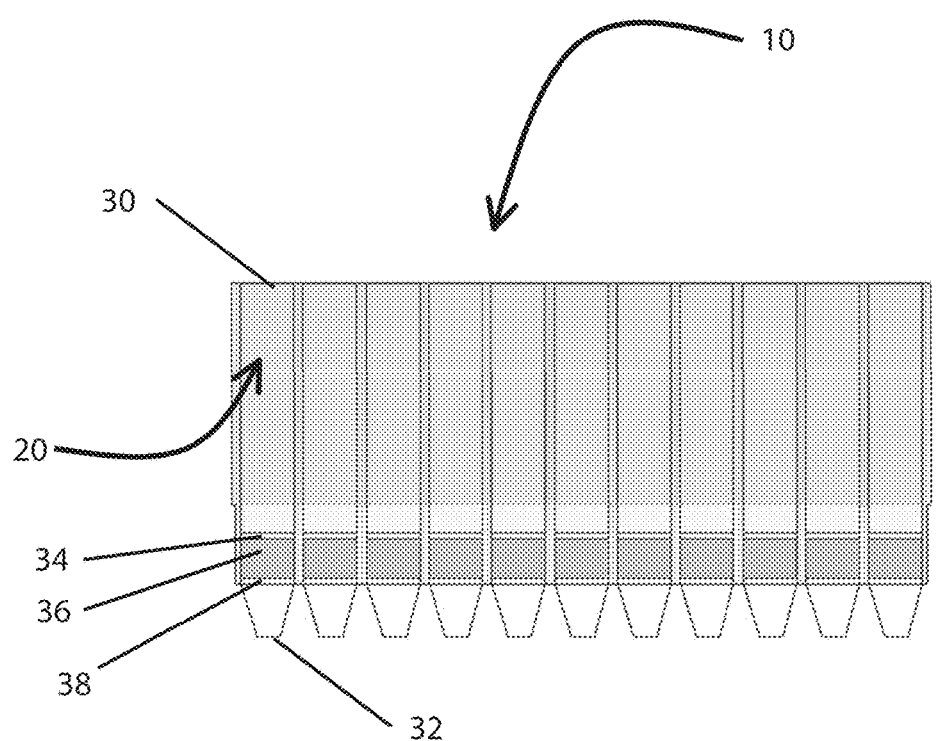
FIG. 3 shows a plurality of SPE cartridges arranged in a system.

The system 10 may optionally include two or more cartridges 20 packed with SPE media 36, as shown in FIG. 3, and the samples may be simultaneously processed in parallel. For example, each well of a 96 well plate may be used as a cartridge 20 in the system 10.

The precipitated sample may be pulled through the system 10 via negative pressure using a vacuum manifold common in general SPE methods and filtration practice. Alternatively, the precipitated sample may be pulled through the system 10 using a positive pressure SPE manifold commonly used in general SPE and filtration practice. Any method may be used to pull or push the precipitated sample through the system 10, so long as the sample is pulled through the system 10 without damaging the system 10, the sample, or target analytes within the sample.

Prior art knowledge and procedures may be applied to adapt and optimize elution protocols, for example by using organic modified buffers, aqueous miscible solvents, binary solvent mixtures, or combinations thereof, in order to achieve selective elution of the analyte. If necessary, multiple elution steps using different conditions may be employed.

Figure 39:
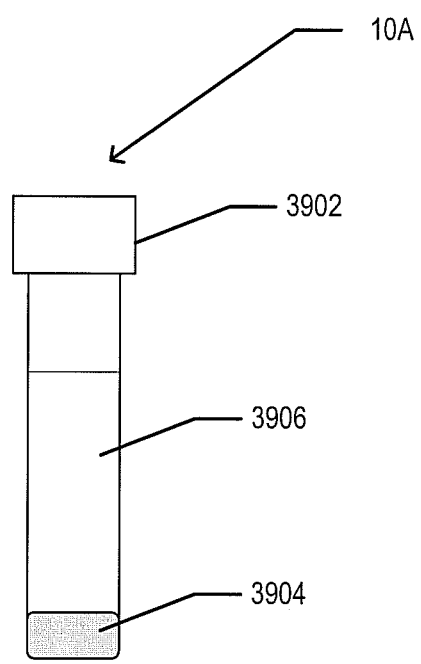
FIG. 39 shows the test tube and hydrophobic transition metal oxide SPE components of the system of the present disclosure.

An alternative system 10A is illustrated in FIG. 39. The system 10A includes a container 3902 in which an amount of SPE media 3904 is situated. A sample 3906 may be introduced into the container 3902 in order to make contact with the SPE media 3904 inside the container 3902. The SPE media 3904 in the container 3902, illustrated in FIG. 39 as a test tube, may have a mass ranging from about 20 mg to about 500 mg. The contents of the container 3902 may be sealed using an known method such as a cap over the test tube opening and mixed using any known method including shaking for a period of at least one minute to achieve the intimate and extended contact between the SPE media 3904 and the sample 3906. After mixing, the treated sample 3906 may be separated from the SPE media 3904 using known methods such as centrifugation. For example, the container 3902 may be centrifuged and upper layer containing the treated sample 3906 may be decanted from the container 3902.

As demonstrated herein, the SPE media, methods, and systems utilizing hydrophobic metal oxide compositions result in high retention rates of lipids with minimal obstruction of the target analytes. Without being bound to any theory, it is believed that the features of the transition metal oxide compositions are based on their unique amphoteric ion-exchange properties in combination with exhibiting strong Lewis acid properties and acting as electron acceptors for Lewis bases, such as phosphate groups. Thus, titanium oxides, zirconium oxides, and cerium oxides show specific chemisorptions of compounds containing one or more phosphate groups. Further, the hydrophobic linker groups also included in the SPE media compositions provide added affinity for non-polar moieties of various lipids. Thus, the polar metal oxide moieties and the non-polar hydrophobic linker compounds included in the SPE media compositions together provide the capability of preferably binding to a variety of lipid species including single-chain phospholipids, double-chain phospholipids, monoglycerides, diglycerides, triglycerides, and cholesterol.

EXAMPLES

The following examples illustrate the invention.

Example 1. Synthesis of Zirconia-Coated Silica and Titania-Coated Silica was Demonstrated Successfully To demonstrate the feasibility of coating silica with zirconia or titania substrates, a pilot study was conducted. Spherical porous silica particles (Daiso Co., Ltd., Osaka, Japan) were pretreated for bonding to the substrates by placing the silica particles into a vacuum oven at 150° C. for 16 hours under full vacuum. To assure anhydrous reaction conditions, the silica was azeotropically dried by adding the silica to HPLC-grade toluene in a 5 L round bottom flask with a Dean Stark trap attached, heating the mixture to 112° C., then draining the flask through the Dean Stark trap a total of 5 times.

After cooling the solution to 35° C., 70% zirconium propoxide in propanol was added to the solution through a dry addition funnel over a period of 1 hour. In this mixture, the zirconium propoxide was reduced to the unbound alcohol by-product, and the zirconia was grafted onto the silica for three hours at room temperature. The mixture was then heated to 112° C. for an additional 16 hours, cooled, and then filtered.

Unreacted zirconium propoxide was subsequently removed by rinsing three times with HPLC-grade toluene and then drying the reactants on the filter. After drying on the filter, the bonded silica was added to a beaker containing 1% formic acid and stirred for one hour, extracting any residual toluene by pipette as necessary.

Finally, the bonded silica was filtered, washed and dried to a constant mass. The bonded silica was filtered from the formic acid solution using a 10-20 μm glass fritted Büchner funnel, rinsed three times with deionized water, rinsed once with acetone, rinsed three times with methanol, and finally dried on the filter. After the initial drying on the filter, the bonded silica was placed into a vacuum oven and further dried until the mass of the bonded silica sample was unchanged with time.

The results of this pilot study demonstrated that zirconia may be bonded successfully to silica, yielding an SPE phase for use in solid phase extraction. Titanium or cerium alkoxides may also be bonded to silica in a similar manner to the methods described above.

Example 2. Filtration Time of Biosamples was Improved Using a Hybrid SPE-Precipitation 96-Well Plate To determine the effect of the arrangement of SPE media, frits, and membranes in the wells of a 96 well plate on the rate of filtration flow through the wells, the following experiment was conducted.

A 96-well plate was prepared in which each well was packed with SPE media that was sandwiched between a 20 μm polyethylene frit at the top of the well, and a 0.2 μm filter/membrane at the bottom of the well. Four different SPE media were used to pack the wells: 30 mg of titania-coated silica prepared using the methods described in Example 1, 30 mg of zirconia-coated silica prepared using the methods described in Example 1, 20 mg of zirconium oxide, and 100 mg of zirconium oxide. As a control, some wells contained only a 20 μm polyethylene frit at the top of each well, and a 0.2 μm filter/membrane at the bottom of each well, with no SPE media in between. For comparison, other wells contained only a standard 0.2 μm hydrophobic graded membrane that is typically used for filtering precipitated proteins (Orochem protein crash plate, catalog number 0021 PPT20, Orochem Technologies, IL).

200 μL of biological rat plasma was added to each of the wells of the packed 96-well plate described above. 600 μL of acetonitrile, a protein precipitation agent, was then pipetted into each well, and the resulting precipitated samples were filtered by applying vacuum to the well-plate using a standard 96-well plate vacuum manifold.

Figure 4:
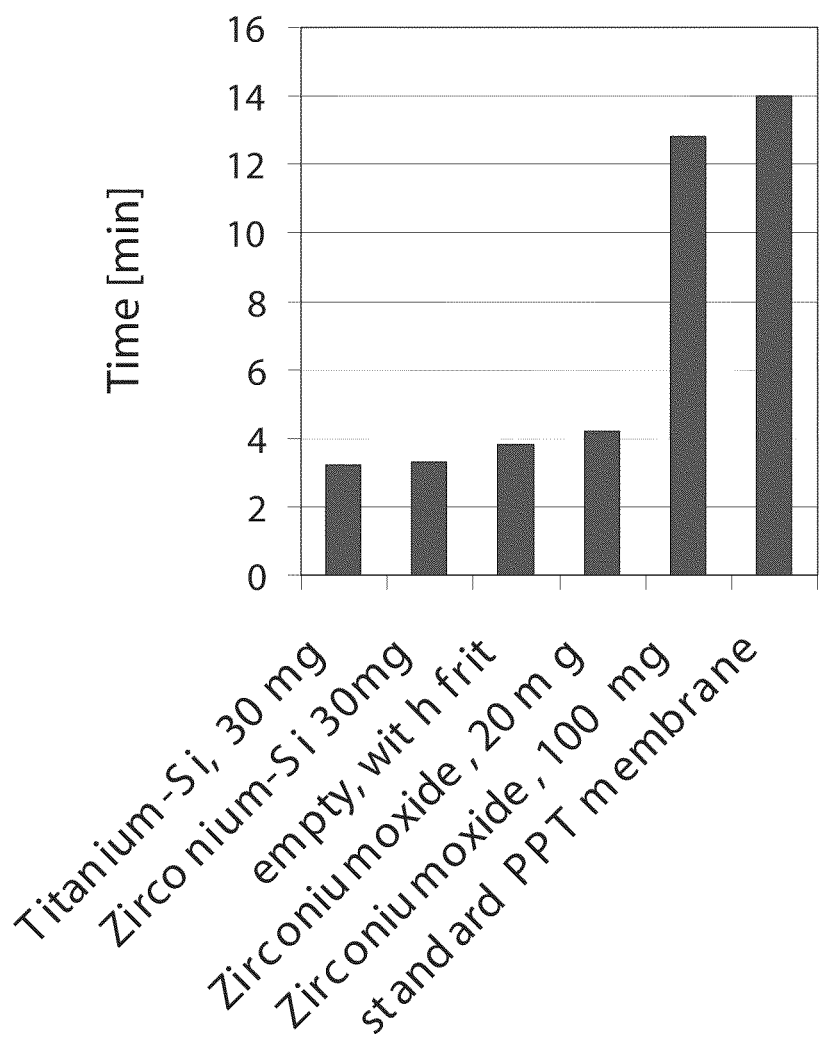
FIG. 4 is a comparison of filtration times of protein precipitated samples through wells packed with different arrangements of chromatographic media and filters.

The lengths of time taken for each of the samples to flow completely through each of the wells in the 96 well plate described above were measured and are summarized in FIG. 4. Complete sample flow-through for the titania-coated silica and zirconia-coated silica filtrations was accomplished in less than 4 minutes, whereas the complete sample flow-through for the standard 0.2 μm protein precipitation membranes took more than 14 minutes, and the complete sample flow-through for the filtration through 100 mg of zirconium oxide took more than 13 minutes The results of this experiment demonstrated that the combination of zirconia-coated silica or titania-coated silica SPE media, sandwiched between a 20 μm polyethylene frit at the top of the well and a 0.2 μM filter/membrane at the bottom of the well, significantly improved the overall sample filtration time over the previous sample preparation methods tested.

Example 3. Coating Silica SPE Media with Zirconia or Titania Significantly Improved the Extraction of Phosphatidylcholine from Samples To determine the effect of zirconia and titania coatings on the capacity of the silica SPE media for extracting phosphatidylcholine, the following study was conducted, comparing the capacities of three different SPE media.

1 ml polypropylene SPE cartridges containing the three different extraction media were prepared. The extraction media were held in place within the SPE cartridges using upper and lower 20 μm polyethylene frits. The first SPE cartridge contained 30 mg of uncoated porous silica (DAISOGEL® SP, Daiso Co., Ltd., Osaka, Japan) with a particle size of 20 μm. The second cartridge contained 30 mg of titania-coated silica, prepared using the methods described in Example 1. The third cartridge contained 30 mg of zirconia-coated silica, prepared using the methods described in Example 1. A fourth cartridge containing 30 mg of titania-coated silica was also tested to determine measurement repeatability.

Each of the SPE cartridges were loaded with 1.0 ml of a standard solution consisting of 1.0 mg/ml of phosphatidylcholine dissolved in 80% acetonitrile and 20% water. The phosphatidylcholine solution was pulled through each of the SPE cartridges drop-wise using an SPE vacuum manifold until the cartridges were dry.

The phosphatidylcholine content of the resulting filtrates were analyzed by HPLC, using a Supelco ASCENTIS® Si column (Sigma-Aldrich, St. Louis, Mo., USA) with a length of 15 cm, an inner diameter of 4.6 mm, and 5 μm particle size. The mobile phase consisted of a 2% $H_3PO_4$ solution in acetonitrile. The HPLC was conducted at a temperature of 35° C., a flow rate of 1250 μl/min and an injection volume of 5 μL. Detection was achieved using UV light at a wavelength of 205 nm.

Figure 5:
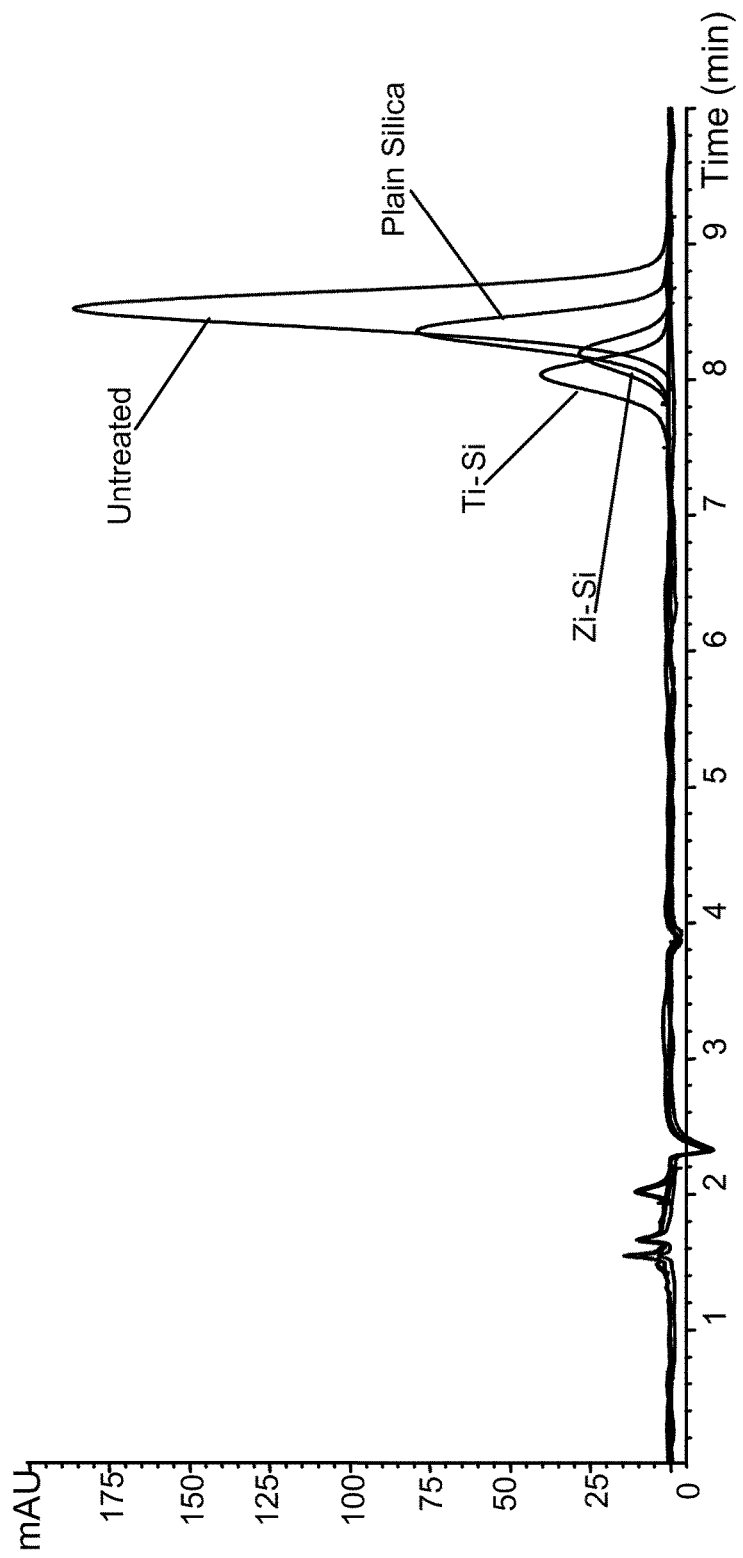
FIG. 5 is an LC-UV diagram comparing the phospholipids content of a phosphatidylcholine solution treated by filtration through SPE cartridges loaded with three different chromatographic media.
Figure 6:
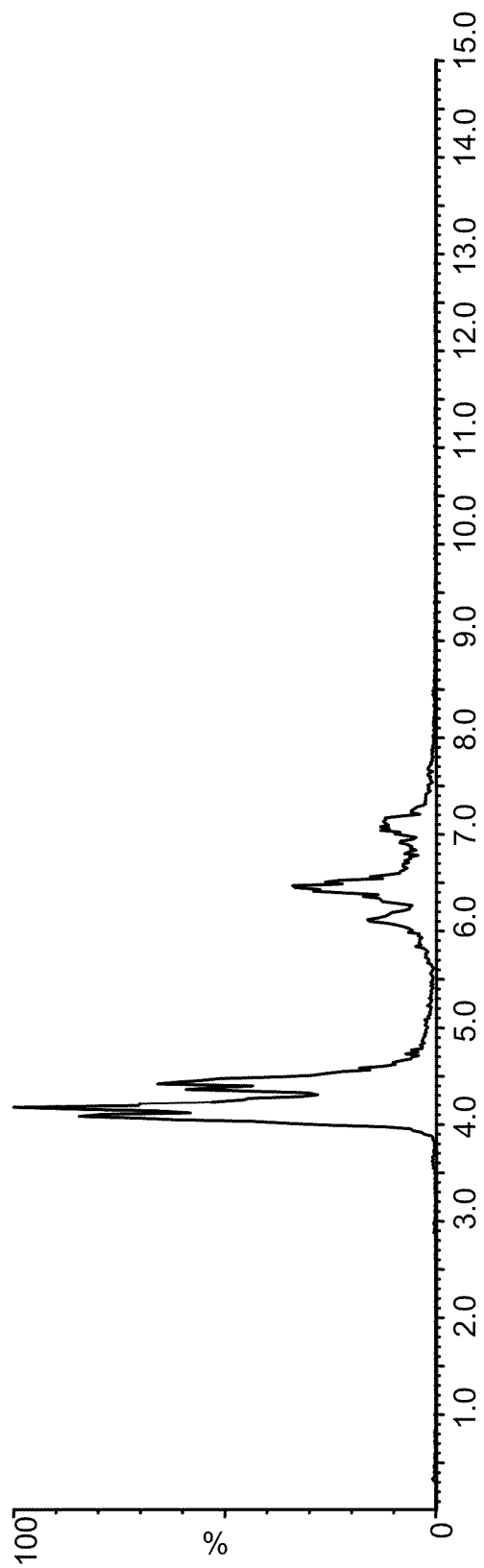
FIG. 6 is an LC-MS diagram of the phospholipids content (MRM: 184 and 104 m/z) of rat plasma after standard protein precipitation.
Figure 7:
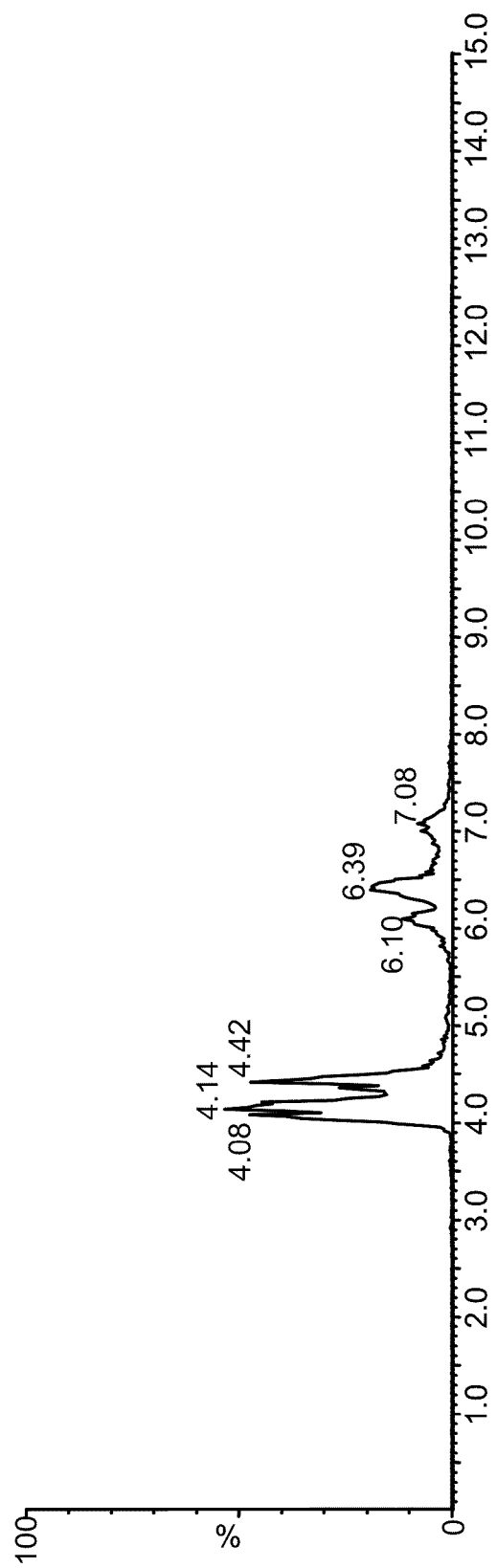
FIG. 7 is an LC-MS diagram of the phospholipids content (MRM: 184 and 104 m/z) of protein-precipitated rat plasma further treated by uncoated silica SPE filtration.
Figure 8:
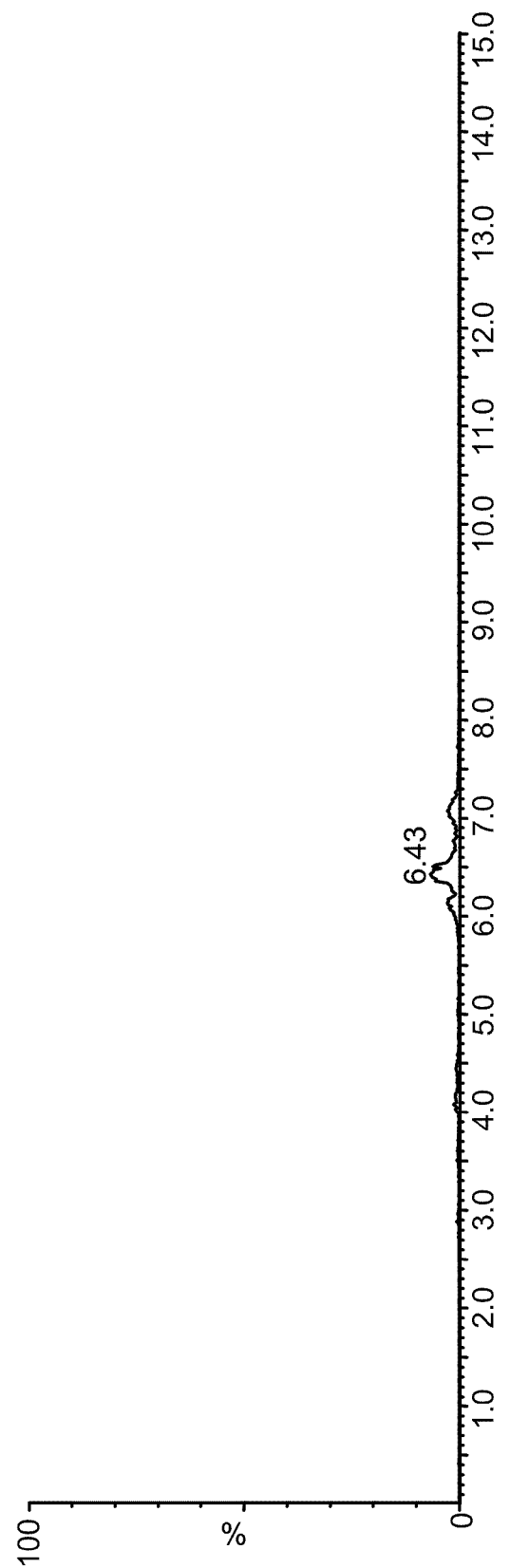
FIG. 8 is an LC-MS diagram of the phospholipids content (MRM: 184 and 104 m/z) of protein-precipitated rat plasma further treated by zirconia-coated silica SPE filtration.
Figure 9:
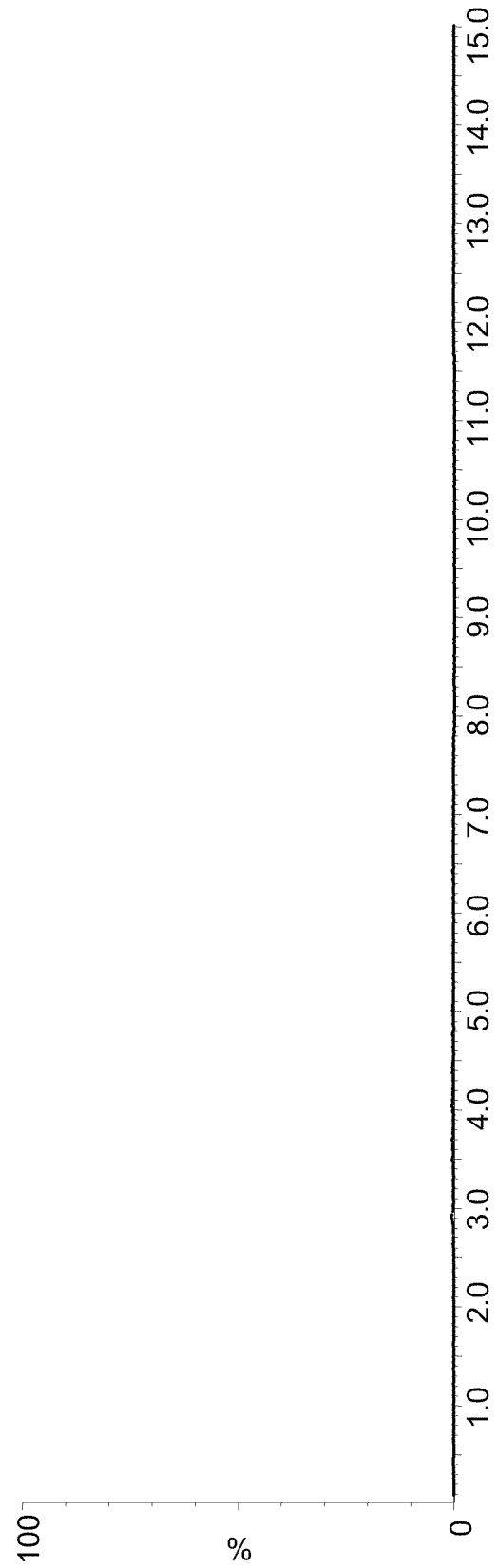
FIG. 9 is an LC-MS diagram of the phospholipids content (MRM: 184 and 104 m/z) of protein-precipitated rat plasma further treated by titania-coated silica SPE filtration.
Figure 10:
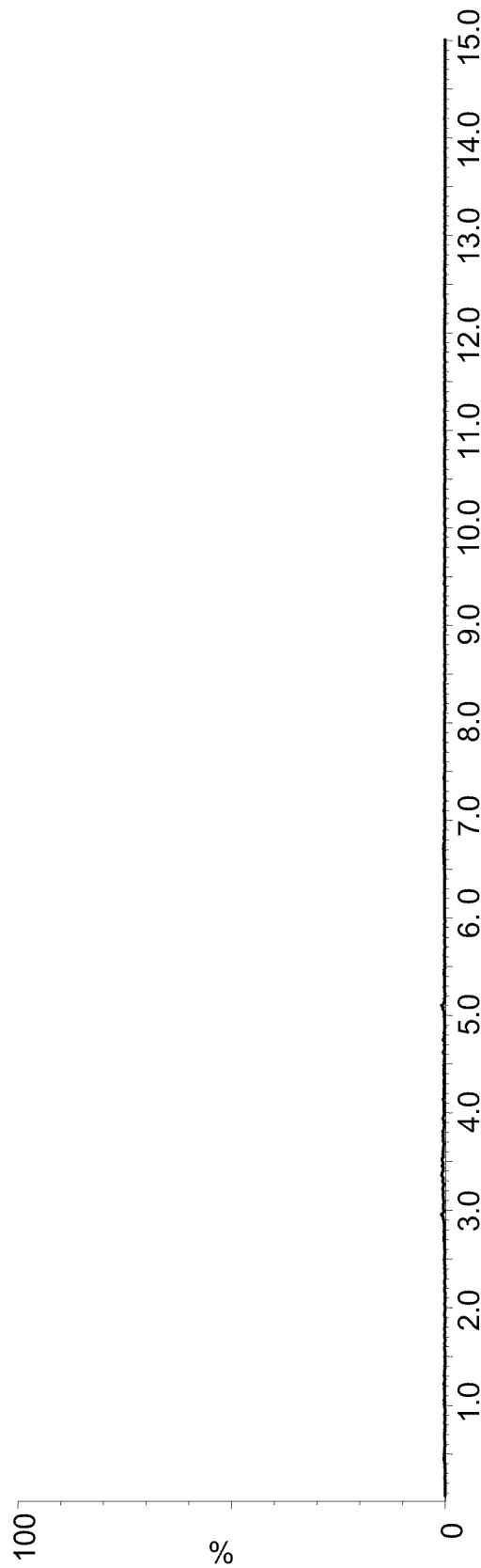
FIG. 10 is an LC-MS diagram of the phospholipids content (MRM: 184 and 104 m/z) of protein-precipitated rat plasma further treated by ceria-coated silica SPE filtration.

The HPLC diagrams obtained for the zirconia-coated silica SPE phase, titania-coated silica SPE phase, plain silica SPE phase, and the untreated standard solution are compared in FIG. 5. The HLPC measurements were converted into the masses of phosphatidylcholine retained by each type of SPE phase, and are summarized in Table 1 below:

TABLE 1

Phosphatidylcholine Retained by Three Different SPE Phases

| SPE Phase material | Mass of Phosphatidylcholine Retained (mg) | Retention by SPE Phase Material (% original) |
|---|---|---|
| None (control) | 0.00 | 0% |
| Silica only | 0.61 | 61% |
| Zirconia-coated silica | 0.81 | 81% |
| Titania-coated silica | 0.87 | 87% |
| Titania-coated silica (repeat) | 0.94 | 94% |

The results of this experiment indicated that coating the silica SPE phase with either zirconia or titania, using the methods described in Example 1, significantly enhanced the capacity of the SPE phase to retain phosphatidylcholine, a common phospholipid in bioanalytical samples.

Example 4. The Capacity of Four Different SPE Phases for Phospholipid Extraction from Rat Plasma was Assessed Under Protein Precipitation Conditions Example 3 demonstrated the enhanced effectiveness of titania-coated and zirconia-coated silica SPE media relative to uncoated silica SPE media at the extraction of phospholipids from a standard solution. However, the effectiveness of the coated silica extraction media under conditions similar to those likely to be used by pharmaceutical bioanalysts had not yet been measured. An experiment was conducted to compare the effectiveness of four different extraction media compositions for the removal of phospholipids from a biological sample under protein precipitation conditions.

1 ml polypropylene SPE cartridges were prepared containing four different SPE media. The SPE media was held in place within each SPE cartridge using upper and lower 20 μm polyethylene frits. The first SPE cartridge contained 30 mg of silica (DAISOGEL® SP, Daiso Co., Ltd., Osaka, Japan) with a pore size of 120 Å and a particle size of 20 μm. The second SPE cartridge contained 30 mg of zirconia-coated silica, prepared using the methods described in Example 1. The third cartridge contained 30 mg of titania-coated silica, prepared using the methods described in Example 1. A fourth cartridge contained 30 mg of ceria-coated silica, prepared using the methods described in Example 1.

For each SPE cartridge, 100 μl of rat plasma was diluted with 300 μl of a 1% formic acid solution in acetonitrile, mixed, and centrifuged to remove any precipitated protein. The resulting supernate was passed through each SPE cartridge using methods described in Example 3, and the resulting eluate for each supernate was analyzed by HPLC-MS. As a control, a separate sample was prepared and analyzed as above using protein precipitation only without further SPE filtration.

The HPLC analysis used a Supelco ASCENTIS® Si column (Sigma-Aldrich, St. Louis, Mo., USA) with a length of 5 cm, an inner diameter of 2.1 mm, and a 3 µm particle size. The HPLC was conducted at a temperature of 50° C. and a flow rate of 0.4 ml/min. The mobile phase consisted of 10 mM ammonium formate at a pH of 4.5 and methanol, the gradient of which is listed in Table 2 below:

TABLE 2

Gradient of Liquid Phase Used in HPLC Analysis

| Time (min) | Ammonium formate (%) | Methanol (%) |
| --- | --- | --- |
| 0 | 80 | 20 |
| 0.2 | 80 | 20 |
| 0.3 | 50 | 50 |
| 1.3 | 0 | 100 |
| 10 | 0 | 100 |
| 10.5 | 80 | 20 |

The mass spectrometry analysis used a MicroMass ZQ single quadrupole instrument with the following settings and conditions: ionization: ESI+, capillary (KV): 3.50, cone (V) 60, extractor: 3, RF lens: 0, source temp: 125° C., desolvation temp: 350° C., desolvation gas: 250 l/hr, cone gas: 90 l/hr, monitoring: scan mode from 80-1000 m/z, extracted ion: 184 and 104 m/z.

LC-MS diagrams targeting phospholipid content after protein precipitation only, without any further SPE processing (control), and protein precipitation followed by SPE processing using uncoated silica, zirconia-coated silica, titania-coated silica, and ceria-coated silica are shown in FIG. 6, FIG. 7, FIG. 8, FIG. 9, and FIG. 10, respectively. The LC-MS responses for phospholipids eluted from each of the SPE media were determined and compared to protein precipitation only (control), assuming that protein precipitation resulted in 0% removal of phospholipids. The results are summarized in Table 3 below.

TABLE 3

Fraction of Phospholipid Removed by 4 Different SPE Media

| SPE Media | Phospholipid Removed by SPE Phase Material (% of original supernate) |
| --- | --- |
| Silica alone | 43% |
| Zirconia-coated silica | 93% |
| Titania-coated silica | 100% |
| Ceria-coated silica | 100% |

In summary, the ceria-coated silica, zirconia-coated silica, and titania-coated silica SPE phase compositions offered excellent removal of phospholipids from plasma samples after previously preparing the samples using protein precipitation methods.

Example 5. Affinity of Zirconia-Coated Silica SPE Phase to a Representative Group of Pharmaceutical Compounds and Metabolites was Assessed The zirconia-coated silica SPE phase was shown to be highly effective at screening out phospholipids in bioanalytical samples in Examples 3 and 4, even under protein precipitating conditions. An additional experiment was conducted to determine the selectivity of the zirconia-coated silica SPE phase for analytes of interest, such as pharmaceutical compounds and metabolites, under conditions sufficient for selectively removing phospholipid compounds.

SPE cartridges containing 30 mg of zirconia-coated silica were prepared as described in Example 4. Standard mix solutions of 12 different compounds consisting of 600 ng/ml of each compound dissolved in a solution of 75% acetonitrile with 1% formic acid and 25% water were prepared. 400 µl of each mix solution was passed through the SPE cartridges with the aid of a SPE vacuum manifold, and the resulting eluate for each cartridge was collected and analyzed by HPLC-MS.

The HPLC analysis used a Supelco DISCOVERY® C18 column (Sigma-Aldrich, St. Louis, Mo., USA) with a length of 5 cm, an inner diameter of 2.1 mm, and 3 µm particle size. The HPLC was conducted at a temperature of 50° C., a flow rate of 200 µl/min, and an injection volume of 5 µl. The mobile phase consisted of 95% 13 mM ammonium formate in methanol, and 5% 13 mM ammonium formate in water.

The mass spectrometry analysis used a MicroMass ZQ single quadrupole instrument with the following settings and conditions: ionization: ESI+, capillary (KV): 3.50, cone (V) 60, extractor: 3, RF lens: 0, source temp: 125° C., desolvation temp: 350° C., desolvation gas: 250 l/hr, cone gas: 90 l/hr, monitoring: scan mode from 80-1000 m/z, extracted ion: compound specific m/z.

The results of the HPLC-MS analysis for the filtrates of each of the twelve mixtures are summarized in Table 4. The results for each ingredient in each mixture were converted into the amount recovered in the filtrate, expressed as a percent of the unfiltered mixture. The target recovery level of at least 55% recovery for each compound was easily reached for 94% of the compounds included in the twelve mixtures.

TABLE 4

Recovery Rates of Mixtures Passed Through Zi-coated Silica SPE Media

| Compounds | MW (mono) | ESI+ | Amount before extraction (XIC) | Amount after extraction (XIC) | Recovery (% original) |
| --- | --- | --- | --- | --- | --- |
| Mixture 1 | | | | | |
| m-toluamide | 135.07 | 136.07 | 126480136 | 97264864 | 76.90 |
| 4-hydroxy-3-methoxyphenylacetic acid | 182.06 | 183.06 | 22800212 | 17278058 | 75.78 |
| propazine | 229.11 | 230.11 | 97665752 | 80976872 | 82.91 |
| mirtazapine | 265.16 | 266.16 | 105867184 | 72262248 | 68.26 |
| benzoylecognine | 289.13 | 290.13 | 62144948 | 25234658 | 40.61 |
| linomycin | 406.21 | 407.21 | 9117189 | 7604725 | 83.41 |

TABLE 4-continued

Recovery Rates of Mixtures Passed Through Zi-coated Silica SPE Media

| Compounds | MW (mono) | ESI+ | Amount before extraction (XIC) | Amount after extraction (XIC) | Recovery (% original) |
|---|---|---|---|---|---|
| Mixture 2 | | | | | |
| ritonavir | 720.31 | 721.31 | 12814102 | 8433283 | 65.81 |
| n-acetyl-l-cysteine | 163.03 | 164.03 | 38623572 | 30404742 | 78.72 |
| nalidixic acid | 232.08 | 233.08 | 9552439 | 6278669 | 65.73 |
| desipramine | 266.17 | 267.17 | 96139472 | 77405648 | 80.51 |
| benzylamine | 107.07 | 108.07 | 20964796 | 33771960 | 161.09 |
| dofetilide | 441.13 | 442.13 | 41493132 | 33249524 | 80.13 |
| Mixture 3 | | | | | |
| 2-deoxyguanosine | 267.09 | 268.09 | 25557700 | 21464814 | 83.99 |
| mifepristone | 429.26 | 430.26 | 64747208 | 53532212 | 82.68 |
| benzanilide | 197.08 | 198.08 | 66199440 | 49822108 | 75.26 |
| nifedipine | 346.11 | 347.11 | 5901884 | 4311448 | 73.05 |
| quinapril | 438.21 | 439.21 | 6574409 | 4754345 | 72.32 |
| Mixture 4 | | | | | |
| apigenin | 270.05 | 271.05 | 23970790 | 16339217 | 68.16 |
| corticosterone | 346.21 | 347.21 | 5901884 | 4311448 | 73.05 |
| folic acid | 441.13 | 442.13 | 41493132 | 33249524 | 80.13 |
| cytosine | 111.04 | 112.04 | 52176028 | 71311744 | 136.68 |
| imiquimod | 240.13 | 241.13 | 93999680 | 74645216 | 79.41 |
| nevirapine | 266.11 | 267.11 | 96139472 | 77405648 | 80.51 |
| simazine | 201.07 | 202.07 | 70499432 | 52413136 | 74.35 |
| Mixture 5 | | | | | |
| estrone | 270.16 | 271.16 | 25630924 | 25897844 | 101.04 |
| venlafaxine | 277.2 | 278.2 | 68316592 | 67112952 | 98.24 |
| creatinine | 113.05 | 114.05 | 37201524 | 30245016 | 81.30 |
| l-lysine | 146.1 | 147.1 | 12863601 | 16987302 | 132.06 |
| memantine | 179.16 | 180.16 | 41916936 | 37810432 | 90.20 |
| a-methylbenzylamine | 121.08 | 122.08 | 11023444 | 16078490 | 145.86 |
| Mixture 6 | | | | | |
| dapsone | 248.06 | 249.06 | 105494368 | 98016304 | 92.91 |
| prilocaine | 220.15 | 221.15 | 355476288 | 3.52E+08 | 99.13 |
| desmethyldiazepam | 270.05 | 271.05 | 25630924 | 25897844 | 101.04 |
| diflucan (fluconazole) | 306.1 | 307.1 | 3420399 | 2839325 | 83.01 |
| captopril | 217.07 | 218.07 | 24092826 | 20963350 | 87.01 |
| Mixture 7 | | | | | |
| pyrimethamine | 248.08 | 249.08 | 105442072 | 1E+08 | 94.96 |
| fenfluraime | 231.12 | 232.12 | 69780768 | 60936636 | 87.33 |
| dextromethorphan | 271.19 | 272.19 | 153701552 | 1.32E+08 | 85.66 |
| xylazine | 220.1 | 221.1 | 355398432 | 3.53E+08 | 99.19 |
| 2-deoxyadenosine | 251 | 252 | 6467978 | 7816253 | 120.85 |
| maprotiline | 277.18 | 278.18 | 68316592 | 67112952 | 98.24 |
| Mixture 8 | | | | | |
| atrazine | 215.09 | 216.09 | 73019280 | 57121224 | 78.23 |
| mianserin | 264.16 | 265.16 | 83827664 | 68501960 | 81.72 |
| phenylbutazone | 308.15 | 309.15 | 7037525 | 3701506 | 52.60 |
| floxin (ofloxacin) | 361.14 | 362.14 | 292219424 | | 0.00 |
| niacinamide | 122.04 | 123.04 | 28446544 | 56544360 | 198.77 |
| clenbuterol | 276.07 | 277.07 | 8158692 | 8953208 | 109.74 |
| Mixture 9 | | | | | |
| sulfadiazine | 250.05 | 251.05 | 6066408 | 3597459 | 59.30 |
| n-acetylprocainamide | 277.17 | 278.17 | 57256968 | 44192764 | 77.18 |
| promazine | 284.13 | 285.13 | 55770524 | 43027904 | 77.15 |
| 4-aminophenylacetic acid | 151.06 | 152.06 | 25719988 | 21218440 | 82.50 |
| trenbolone | 270.16 | 271.16 | 68761848 | 51695468 | 75.18 |
| Mixture 10 | | | | | |
| tamoxifen | 371.22 | 372.22 | 173316688 | 1.45E+08 | 83.56 |
| 5-fluorocytosine | 129.02 | 130.02 | 18569570 | 13626637 | 73.38 |
| 2-Amino-3-phenyl-1-propanol | 151.09 | 152.09 | 25719988 | 21218440 | 82.50 |
| hippuric acid | 179.05 | 180.05 | 98845000 | 74262880 | 75.13 |
| sertraline | 305.07 | 306.07 | 6206996 | 5953191 | 95.91 |
| haloperidol | 375.14 | 376.14 | 71763880 | 58925732 | 82.11 |
| virginiamycin M1 | 525.24 | 526.24 | 2887174 | 1472945 | 51.02 |

TABLE 4-continued

Recovery Rates of Mixtures Passed Through Zi-coated Silica SPE Media

| Compounds | MW (mono) | ESI+ | Amount before extraction (XIC) | Amount after extraction (XIC) | Recovery (% original) |
|---|---|---|---|---|---|
| Mixture 11 | | | | | |
| vigabatrin | 129.07 | 130.07 | 18569570 | 13626637 | 73.38 |
| phenacetin (p-acetophenetidide) | 179.09 | 180.09 | 98845000 | 74262880 | 75.13 |
| 4-decyloxybenzoic acid | 278.18 | 279.18 | 16968362 | 14449392 | 85.15 |
| clomipramine | 314.15 | 315.15 | 37481840 | 31531476 | 84.12 |
| fluoxetine | 309.13 | 310.13 | 6154572 | 7095674 | 115.29 |
| riboflavin | 376.13 | 377.13 | 24951728 | 16573426 | 66.42 |
| 5-aminosalicylic Acid | 153.04 | 154.04 | 16568016 | 10365297 | 62.56 |
| Mixture 12 | | | | | |
| xanthosine | 284.07 | 285.07 | 55770524 | 37640212 | 67.49 |
| mesoridazine | 386.14 | 387.14 | 87603968 | 54980640 | 62.76 |
| theobromine | 180.06 | 181.06 | 25590428 | 23044046 | 90.05 |

The results of this experiment demonstrated that the zirconia-coated silica SPE media possessed a low affinity for the overwhelming majority of the compounds tested, representing a variety of pharmaceutical compounds and metabolites.

Example 6. Effectiveness of Zirconia-Coated Silica at Removing Phospholipids from Rat Plasma was Compared with Zirconium Oxide Particles An experiment was conducted to evaluate the performance of a zirconia-coated silica SPE media, in comparison to pure zirconium oxide in the extraction of phospholipids for bioanalytical samples.

A 96-well plate was prepared by packing SPE media into each well using two opposing filter/frits. The upper frit consisted of a 20 µm porosity polyethylene frit and the lower frit consisted of a 0.2 µm filter/frit commonly used to filter out particulate biomatter after protein precipitation. The extraction media tested consisted of: 50 mg of zirconium oxide particles, 180 mg of zirconium oxide particles, and 50 mg of zirconia-coated silica particles.

As a control, 100 µl of rat plasma sample was subjected to standard protein precipitation without SPE processing using the method described in Example 4. The remaining test samples were subjected to hybrid SPE/protein precipitation by first applying 100 µl of rat plasma, followed by 300 µl of acetonitrile with 1% formic acid into each test well. The plate was then agitated for 1 minute, and vacuum was applied to draw the samples through the wells. The resulting eluate from each well was collected and analyzed directly by HPLC.

The HPLC analysis used a Supelco ASCENTIS® Express C18 column (Sigma-Aldrich, St. Louis, Mo., USA) with a length of 5 cm, an inner diameter of 4.5 mm, and 2.7 µm particle size. The HPLC was conducted at a temperature of 35° C. and a flow rate of 500 µl/min. Mass-spectrometry detection was conducted using a Sciex API 3200 Q TRAP with the following settings and conditions: ionization: ESI+, ion-source: turbospray, ion-spray voltage: 5500 V, source temperature: 425° C., ion-source gas 1:35 psi, ion-source gas 2:45 psi, declustering potential: 125 V, entrance potential: 10 V, MRM transitions: phospholipids (184 m/z and 104 m/z). The mobile phase consisted of 10 mM ammonium acetate and 10 mM ammonium acetate in acetonitrile, the gradient of which is listed in Table 5 below.

TABLE 5

Gradient of Mobile Phase Used in HPLC Analysis

| Time (min) | Ammonium acetate (%) | Ammonium acetate in acetonitrile (%) |
|---|---|---|
| 0 | 95 | 5 |
| 10 | 50 | 50 |
| 18 | 50 | 50 |
| 18.1 | 95 | 5 |
| 22 | 95 | 5 |

Figure 11:
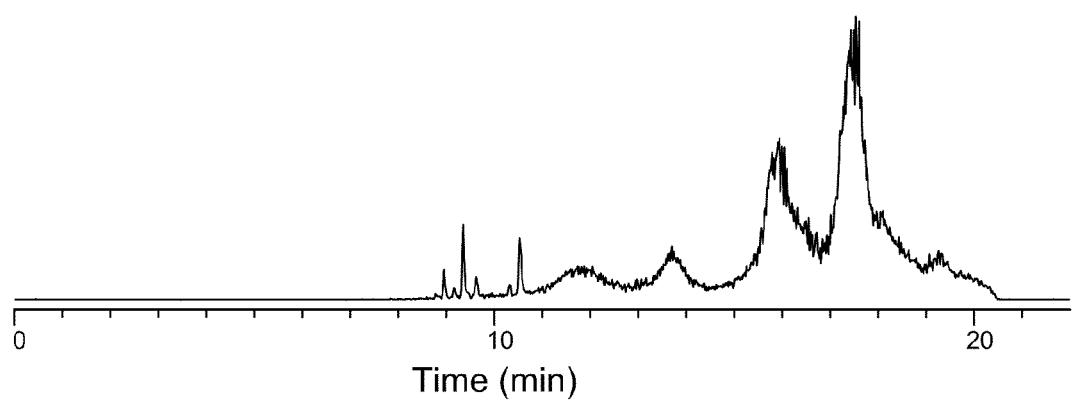
FIG. 11 is an LC-MS diagram of the phospholipids content (MRM: 184 and 104 m/z) of rat plasma after standard protein precipitation.
Figure 12:
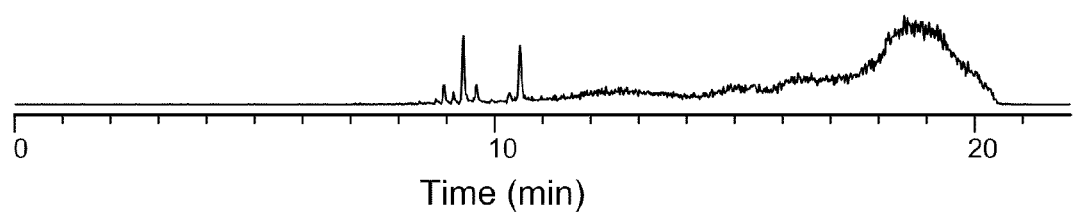
FIG. 12 is an LC-MS diagram of the phospholipids content (MRM: 184 and 104 m/z) of a protein-precipitated rat plasma sample after further SPE filtration using 50 mg zirconium oxide.
Figure 13:
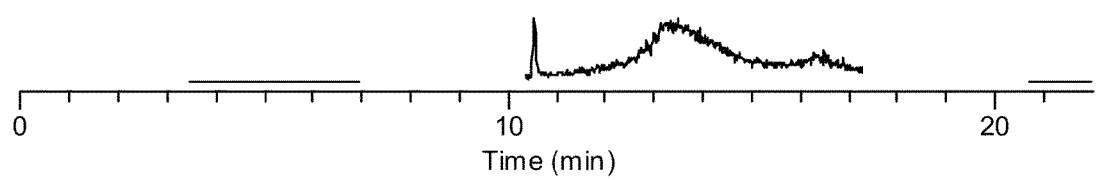
FIG. 13 is an LC-MS diagram of the phospholipids content (MRM: 184 and 104 m/z) of a protein-precipitated rat plasma sample after further SPE filtration using 180 mg zirconium oxide.
Figure 14:
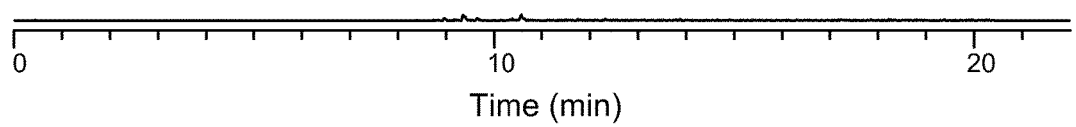
FIG. 14 is an LC-MS diagram of the phospholipids content (MRM: 184 and 104 m/z) of a protein-precipitated rat plasma sample after further SPE filtration using 50 mg zirconia-coated silica.

The HPLC diagram obtained for the rat plasma sample that was protein precipitated, but not filtered by SPE, is shown in FIG. 11. The HPLC diagram obtained for the protein-precipitated rat plasma sample filtered by SPE using 50 mg of zirconium oxide particles in the well, 180 mg of zirconium oxide particles in the well, and 50 mg of zirconia-coated silica particles in the well are shown in FIG. 12, FIG. 13 and FIG. 14 respectively. The peak response levels of the detected phospholipids for each processed sample were measured and compared against the peak response level of the control sample resulting from standard protein precipitation without further SPE filtration. The percent of phospholipids removed relative to the phospholipids removed using protein precipitation alone are summarized in Table 6.

TABLE 6

Phospholipids Removed by Different Sample Preparation Protocols

| Sample Preparation | % Phospholipid Removal |
|---|---|
| Standard Protein Precipitation | 0% |
| Zirconium Oxide 50 mg | 46% |
| Zirconium Oxide 180 mg | 49% |
| Zirconia-coated Silica 50 mg | 99% |

The results of this experiment demonstrated the enhanced capacity for the binding of phospholipids by the zirconia-coated silica media relative to the zirconium oxide media. Pure zirconium oxide had limited effectiveness in bioanalytical sample preparation applications due to its low capacity for the removal of phospholipids. The high surface area of the zirconia-coated silica particles enhanced the capacity of this media to a level sufficient to remove 99% of the sample's phospholipids relative to the phospholipids removed by standard protein precipitation methods.

Example 7. Hybrid SPE/Protein Precipitation Used to Determine the Magnitude of Ion Suppression Effects of Phospholipids on Detection of Selected Compounds To determine the effect of phospholipids on the ionization of non-acidic compounds in electrospray positive ion mode LC-MS, an experiment was conducted to compare the response levels of these non-acidic compounds detected by LC-MS in the presence and absence of phospholipids. The experiment proceeded in two stages. Biological samples processed by either standard protein precipitation or hybrid SPE/protein precipitation (protein precipitation followed by zirconium-coated silica SPE filtration) were analyzed in a manner in which the phospholipids that were inadequately removed during each sample prep process were selectively retained chromatographically on a C18 reverse phase HPLC column. Subsequent injection of a standard mixture of non-acidic compounds into the HPLC columns enabled the overlap of phospholipids with the non-acidic compounds resulting in an effective method for the determination of the ion-suppression effect of phospholipids. By modifying the gradient conditions of the phospholipids, retention overlap of the non-acidic standard mixture with the desired range of phospholipid species was controlled.

Rat plasma samples were subjected to standard protein precipitation using the methods described in Example 4. An aliquot of the supernate resulting from the protein-precipitated rat plasma samples was further subjected to filtration through a 1 ml SPE cartridge containing 30 mg of zirconia-coated silica SPE media for phospholipid removal, using the methods described in Example 4.

The effect of the phospholipids extracted from rat plasma samples, using the hybrid SPE/protein precipitation method, described in Example 4, on the ionization of the test mixture was assessed by comparing the LC-MS diagrams of selected compounds in the presence and absence of the extracted phospholipids. The measurements used to determine this effect were performed in two sequential stages.

Initially, the blank rat plasma samples processed by standard protein precipitation alone or protein precipitation followed by zirconium-coated silica SPE filtration were injected onto the chromatographic columns and retained through the gradient system described in Table 7 below. The gradient described in Table 7 was designed to retain any phospholipids still evident in the samples after sample processing. Next, a standard solution consisting of 100 ng/ml each of clonidine, protryptiline, clomipramine and desmethyldiazepam was prepared, injected into the same chromatographic column, and LC-MS analysis was performed using the gradient given in Table 8 below. By selectively overlapping the standard compounds with the phospholipids during chromatographic analysis, the ionization effect of phospholipids on the standard compounds was determined. The methods used in this experiment eliminated other potentially confounding factors, such as endogenous biological sample salts or anticoagulants, which can also cause ion-suppression.

The HPLC analysis used a Discovery C18 column (Sigma-Aldrich, St. Louis, Mo., USA) with a length of 5 cm, an inner diameter of 2.1 mm, and a 3 μm particle size. The HPLC was conducted at a temperature of 50° C. and a flow rate of 200 μl/min and an injection volume of 5 μl. The mobile phase consisted of 13 mM Ammonium Acetate in Methanol and 13 mM Ammonium Acetate in Water. The gradient used in the first stage of the experiment is given in Table 7 below, and the gradient used in the second stage of the experiment is given in Table 8 below:

TABLE 7

Gradient of Liquid Phase Used in Stage 1 of HPLC Analysis

| Time (min) | Ammonium Acetate in Water (%) | Ammonium Acetate in Methanol (%) |
| --- | --- | --- |
| 0 | 40 | 60 |
| 7 | 40 | 60 |
| 12 | 0 | 100 |
| 17 | 0 | 100 |

TABLE 8

Gradient of Liquid Phase Used in Stage 2 of HPLC Analysis

| Time (min) | Ammonium Acetate in Water (%) | Ammonium Acetate in Methanol (%) |
| --- | --- | --- |
| 0 | 0 | 100 |
| 7 | 0 | 100 |
| 12 | 40 | 60 |
| 17 | 40 | 60 |

Figure 15:
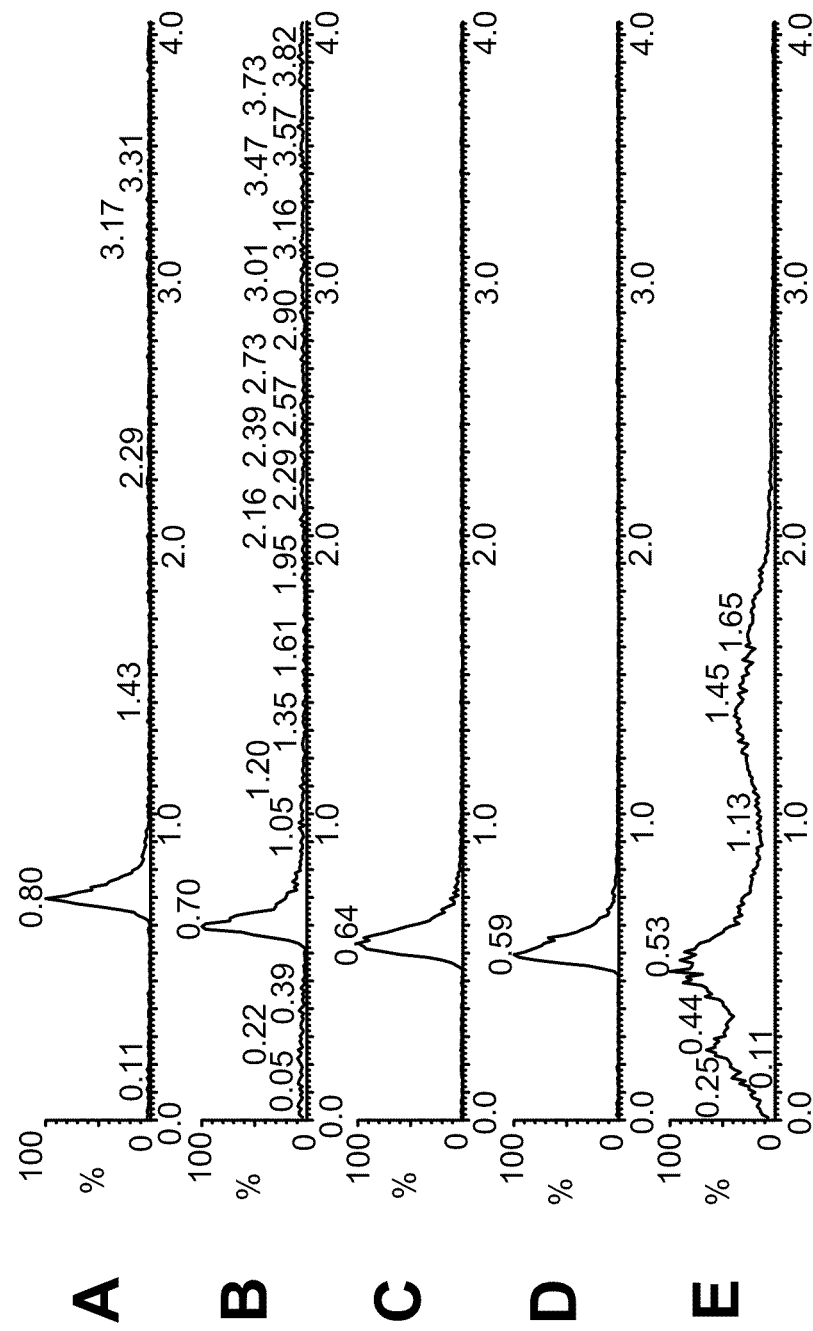
FIG. 15 is a series of LC-MS diagrams that depict the ion-traces (MRM) and co-elution of each of the analytes of interest with phospholipids injected in stage 1.

The mass spectrometry analysis used a MicroMass ZQ single quadrupole instrument with the following settings and conditions: ionization: ESI+, capillary (KV): 3.50, cone (V) 40, extractor: 3, RF lens: 0, source temp: 125° C., desolvation temp: 350° C., desolvation gas: 250 l/hr, cone gas: 90 l/hr, monitoring: scan mode from 80-400 m/z, extracted ion: 184, 230, 264, 271, and 315 m/z. The HPLC diagrams showing the amounts of Clonidine (m/z 230), Protryptiline (m/z 264), Clomipramine (m/z 315), Desmethyldiazepam (m/z 271), and Phospholipids (m/z 184). Using this two-step gradient, co-elution of the phospholipids with analytes was achieved, and is shown in FIG. 15.

In the second stage of this experiment, LC-MS response levels of each of the non-acidic test compounds were determined using columns prepared using injections of blank rat plasma sample subjected to protein precipitation alone, using injections of blank rat plasma sample subjected to protein precipitation followed by zirconium-coated silica SPE filtration, or control columns prepared using no prior injections. The results were expressed as percent response of each compound that was measured using the control column. The results are summarized in Table 9.

TABLE 9

Effect of Phospholipids on Ionization of 4 Compounds Added to Rat Plasma Samples Prepared Using Protein Precipitation and Hybrid SPE/Protein Precipitation

| Rat plasma sample preparation | Clonidine (m/z 230) (% ionization response) | Protryptiline (m/z 264) (% ionization response) | Desmethyldiazapam (m/z 271) (% ionization response) | Clomipramine (m/z 315) (% ionization response) |
|---|---|---|---|---|
| Hybrid SPE/Protein Precipitation | 96.70% | 104.11% | 102.55% | 97.81% |
| Standard Protein Precipitation Alone | 54.50% | 44.72% | 81.85% | 110.91% |

The ion-suppression effect of phospholipids on the non-acidic compounds tested resulted in up to 50% signal suppression when overlapped with extracts derived from standard protein precipitation of rat plasma. When using the hybrid SPE/protein precipitation approach, more than 99% of the phospholipids were extracted from the rat plasma sample resulting in minimal signal suppression of the non-acidic compounds tested.

Example 8. The Effect of Formic Acid on Analyte Recovery after Sample Preparation Using the Hybrid SPE/Protein Precipitation Method was Determined for Two Representative Pharmaceutical Compounds Previous examples, described above, involve an initial step of mixing the 100 μL bioanalytical sample with a dilute formic acid in acetonitrile solution. An experiment was conducted to determine the effect of formic acid on analyte recovery and phospholipid removal using hybrid SPE/protein precipitation methods. Formic acid is a strong enough Lewis Base to prevent most acidic pharmaceutical compounds from binding with the zirconia ions in the SPE phase, and may also inhibit the binding of non-acidic pharmaceutical compounds to residual silanol groups on the silica support surface of the SPE phase.

The effects of variations in the formic acid/acetonitrile mixture used in the initial steps of the hybrid SPE/protein precipitation sample preparation method on efficiency of analyte recovery was assessed for two representative drug compounds: propranolol, a non-acidic compound, and ketoprofen, an acidic compound.

A hybrid SPE 96-well plate was prepared by packing 50 mg of zirconia-coated silica particles (as prepared in Example 1) into each well between two opposing filter/frits. The upper frit consisted of a 5 μm porosity PTFE frit and the lower consisted of a 0.2 μm filter/frit commonly used to filter out particulate bio-matter after protein precipitation. 100 μl rat plasma samples spiked at the level of 100 ng/ml ketoprofen and propanol were transferred in duplicate to the individual wells of the 96-well plate followed by 300 μl acetonitrile containing formic or acetic acid at a concentration ranging between 0% and 2%. The 96-well plate was vortexed for 1 minute, and vacuum pressure was applied to the well plate using a 96-well plate vacuum manifold and the resulting eluate was analyzed directly via LC-MS analysis.

The HPLC analysis used a Discovery HS F5 column (Sigma-Aldrich, St. Louis, Mo., USA) with a length of 100 cm, an inner diameter of 2.1 mm, and a particle size of 3 μm. The HPLC was conducted at a temperature of 50° C. and a flow rate of 200 μl/min and an injection volume of 5 μl. The mobile phase consisted of 13 mM Ammonium Acetate in Methanol and 13 mM Ammonium Acetate in Water. The gradient used for the HPLC analysis is given in Table 10 below.

TABLE 10

Gradient of Liquid Phase Used in HPLC Analysis

| Time (min) | Ammonium Acetate in Water (%) | Ammonium Acetate in Methanol (%) |
|---|---|---|
| 0 | 75 | 25 |
| 2 | 95 | 5 |
| 4.5 | 95 | 5 |
| 5 | 75 | 25 |
| 7 | 75 | 25 |

Mass-spectrometry detection was conducted using a Sciex API 3200 Q TRAP with the following settings and conditions: ionization: ESI+, curtain gas (psi): 25, ion-source: turbospray, ion-spray voltage (V): 4500, source temperature (° C.): 450, ion-source gas 1 (psi): 35, ion-source gas 2 (psi): 20, collision gas (psi): 4, MRM Transitions: propanolol (260.30/116.10) and ketoprofen (255.20/209.10).

The LC-MS data for the samples containing propanol and ketoprofen were analyzed to determine the percent absolute recovery of each compound. Absolute recovery was calculated against external calibration standards (data not shown). The results are summarized in Table 11 to compare the effects of formic and acetic acid on the absolute recovery of propanolol and ketoprofen.

TABLE 11

Effect of Organic Acid Concentration on the Recovery of Acidic and Non-acidic Pharmaceutical Drug Compounds after Hybrid SPE/Protein Precipitation

| Percent of organic acid in solution with acetonitrile | Propanolol (Non-acidic) Recovery (% of original sample) | | Ketoprofen (Acidic) Recovery (% of original sample) | |
|---|---|---|---|---|
| | Formic acid used | Acetic acid used | Formic acid used | Acetic acid used |
| 0.0% | 73% | 73% | 0% | 0% |
| 0.1% | 77% | 73% | 0% | 0% |
| 0.2% | 75% | 70% | 35% | 7% |
| 0.5% | 72% | 72% | 84% | 51% |
| 1.0% | 75% | 70% | 96% | 69% |
| 1.5% | 77% | 68% | 114% | 78% |
| 2.0% | 77% | 72% | 114% | 78% |

The results of this study indicated that the addition of organic acid enhanced the recovery of pharmaceutical acidic compounds processed using the hybrid SPE/protein precipitation method. The zirconia-coated silica SPE phase retained ketoprofen, an acidic pharmaceutical compound, in the absence of any organic acid, but with the addition of either formic acid or acetic acid, the recovery of ketoprofen was greatly enhanced. Although both organic acids enhanced the recovery of ketoprofen, formic acid completely inhibited the retention of ketoprofen by the HybridSPE phase, as evidenced by the 100% recovery for concentrations of formic acid that were 1% or greater, as shown in Table 11. By contrast, the organic acids had negligible impact on the recovery of the non-acidic molecule propanolol for any of the organic acid concentrations tested.

Example 9. Analyte Recovery Using Hybrid SPE/Protein Precipitation Methods was Determined to be Sensitive to Variations in the Relative Proportion of Protein Precipitation Agent Used To further optimize the hybrid SPE/protein precipitation sample preparation method, an experiment was conducted to determine the effect of the relative volume of protein precipitation agent added to the bioanalytical sample during the hybrid SPE/protein precipitation method on the subsequent recovery of analytes.

The wells of a 96 well plate were packed with 50 mg of zirconia-coated silica SPE media, as described in Example 8. Rat plasma samples were spiked at the levels of 100 ng/ml propanolol and ketoprofen. 100 µl aliquots of the spiked rat plasma were added to each test well and mixed with either 1% formic acid in acetonitrile or 1% acetic acid in acetonitrile. The precipitating agent volume ratios tested in this experiment ranged from 1:3 (100 µl plasma: 300 µl precipitating agent) to 1:5 (100 µl plasma: 500 µl precipitating agent). The resulting eluate derived from each test was analyzed using HPLC-MS as described in Example 8.

The HPLC-MS data for the samples containing propanol and ketoprofen were analyzed to determine the percent absolute recovery of each compound. Absolute recovery was calculated against external calibration standards (data not shown). A comparison of the effects of the amount of organic acid/precipitating agent added to biological samples on the absolute recovery of propanolol and ketoprofen are summarized in Table 12.

TABLE 12

Effect of the Volume of Protein Precipitation Agent Relative to Sample Volume on the Recovery of Acidic and Non-acidic Pharmaceutical Drug Compounds after Hybrid SPE/Protein Precipitation

| Ratio of Sample Volume to Protein | Propanolol (Non-acidic) Recovery (% of original sample) | | Ketoprofen (Acidic) Recovery (% of original sample) | |
|---|---|---|---|---|
| Precipitation Agent Volume | Formic acid used | Acetic acid used | Formic acid used | Acetic acid used |
| 1:2 | 70% | 68% | 68% | 44% |
| 1:3 | 75% | 70% | 96% | 69% |
| 1:5 | 70% | 62% | 107% | 82% |

The results of this experiment indicated that the recovery of ketoprofen, an acidic pharmaceutical molecule, was sensitive to relative volume of protein precipitation agent used in the hybrid SPE/protein precipitation process. A minimum ratio of protein precipitation agent to sample volume ratio of 3:1 was necessary for optimal recovery of the ketoprofen analyte. Although a 5:1 volume ratio provided a slightly better recovery of ketoprofen, the added volume of protein precipitation agent diluted the sample, resulting in decreased sensitivity during analysis (data not shown).

Based on the results of the present example, as well as the results presented in Example 8, the likely optimal precipitation agent was determined to be 1-2% formic acid in acetonitrile, added to the bioanalytical sample at a 3:1 ratio (precipitation agent:sample). Formic acid is an ideal reagent for the hybrid SPE/protein precipitation because it was not a strong enough Lewis base to displace the phosphate moiety inherent with phospholipids from the zirconia SPE functional groups, but the formic acid was strong enough to keep carboxylic acid moieties, such as those found in most acidic pharmaceutical compounds, from binding to the Zr—Si phase used in the hybrid SPE/protein precipitation method. While formic acid did not play a major role in controlling non-acidic compound binding, formic acid minimized secondary cation-exchange interactions between the exposed silanol groups on the silica SPE surface and non-acidic compounds.

Example 10. Filtration of Hybrid SPE/Protein Precipitated Samples was Optimized Through the Use of a PTFE Upper Frit Previous methods of hybrid SPE/protein precipitation described in Examples 2 and 6 utilized standard 20 µm PE (polyethylene) upper frits. However, continued use of this method revealed that protein precipitation within the 96-well plate and subsequent filtration using the frit/packed-bed/filter assembly resulted in a very cloudy eluate. Such cloudiness may lead to subsequent system failure during LC-MS-MS due to clogging and/or increased backpressure. The cloudiness was due to the plasma samples partially leaking through the upper frit prior to the addition of the precipitating agent, resulting in some of the proteins in the samples precipitating after the eluates had passed through the packed bed assemblies.

An experiment was conducted to determine the effect of the material composition and porosity of the upper frit on the turbidity of the eluate in the hybrid SPE/protein precipitation system. 96-well plates were prepared as described in Example 6, in which 50 mg of zirconia-coated silica media was packed in a 96-well SPE plate. The bottom filter/frit consisted of a 0.2 µm porosity filter/frit assembly common in standard 96-well precipitation plates. The upper frits tested in the example consisted of 20-µm porosity PE filters, 5-µm porosity PTFE (polytetrafluoroethylene) filters, 7-µm porosity PE filters, and 10-µm porosity PTFE filters.

Blank rat plasma samples were processed using the 96-well plate described above and the hybrid SPE/protein precipitation method described in Example 6. The resulting eluate of each test well was collected for visual inspection and analysis. The results of the visual analysis are summarized in Table 13.

TABLE 13

The Effect of Upper Frit Types on the Turbidity of Eluates Resulting from the Hybrid SPE/Protein Precipitation of Rat Plasma

| Upper Frit Type and Porosity in Well | Visual Turbidity of Eluates |
|---|---|
| 20 µm PE | Most cloudy |
| 5 µm PTFE | Clear |
| 7 µm PE | Very cloudy |
| 10 µm PTFE | Little cloudy |

PTFE, a hydrophobic polymer used to mold one of the frit materials under investigation, inhibited the passage of the aqueous plasma sample, requiring negative pressure to induce the flow of the sample through the frit into the SPE media below. However, the pore size of the 10-µm PTFE frit lowered the impedence of the filter sufficiently to allow the passage of some aqueous plasma prior to the addition of the protein precipitation agent to the well. Both the 7-µm PE and 20-µm PE frits also allowed plasma sample to pass through to the SPE media prior to the addition of the protein precipitation agent. Using the 5-µm PTFE frit greatly enhanced the effectiveness of the hybrid SPE/protein precipitation method by impeding the flow of the aqueous bioanalytical sample long enough to allow time for the addition of a protein precipitation agent prior to the passage of the sample through the frit to the SPE media in the well. The hydrophobic nature of the acetonitrile used as a protein precipitating agent facilitated flow through the upper frit. 400 µl of the protein-precipitated bioanalytical sample liquid passed through the entire well assembly (5 µM PTFE upper frit+SPE media+0.2 µM lower filter) in 1-2 minutes, compared to the standard protein precipitation method in which the same amount of bioanalytical sample took about 5-10 minutes to flow through the entire well assembly, which contained only a single 0.2 µM filter.

The results of this experiment demonstrated that a 5 µM PTFE upper filter is optimal for the hybrid SPE/protein precipitation method, since this filter delayed the flow of the bioanalytical sample into the SPE media just long enough to give time for the addition of protein precipitation agent, yet the device allowed the entire 400 µl of the bioanalytical sample to flow through the entire well assembly in less that two minutes (data not shown).

Example 11. Hybrid SPE/Protein Precipitation Sample Preparation Method Compared to Existing SPE Methods and Existing Protein Precipitation Methods To assess the effectiveness of the hybrid SPE/protein precipitation sample treatment method relative to other benchmark sample treatment processes, an experiment was conducted to compare the performance of the hybrid SPE/protein precipitation method to standard SPE sample treatment methods as well as standard protein precipitation methods.

A hybrid SPE 96-well plate was prepared using the method described in Example 8. The SPE media used for comparison in this example consisted of Oasis® HLB SPE media (Waters, Inc.) which is a macroporous copolymer of divinylbenzene and N-vinylpyrrolidone, and YH-OH SPE media (Yuhai Chemical Technologies) which is a macroporous hydroxylated polystyrene/divinylbenzene polymer. Both SPE phases were packed separately into 1 ml polypropylene SPE cartridges between two 20-µm porosity PE frits. The bed weight for the Oasis HLB and YH-OH media was 60 mg and 50 mg, respectively.

Rat plasma was spiked with propanolol and ketoprofen at the level of 100 ng/ml for each compound. 100 µl of blank and spiked rat plasma were subjected to hybrid SPE/protein precipitation using the method described in Example 6. 100 µl of blank and spiked rat plasma were separately subjected to standard protein precipitation (without further SPE processing) as described in Example 4. For the standard SPE methods using Oasis HLB and YH-OH SPE cartridges, 200 µl of blank and spiked rat plasma were loaded onto each separate SPE cartridge after preconditioning with 1 ml methanol followed by 1 ml deionized water with the aid of an SPE vacuum manifold. After sample loading, the cartridges were washed with 1 ml of 5% methanol in deionized water twice, and eluted with 1 ml methanol. The resulting eluate was evaporated under nitrogen to dryness and reconstituted with 800 µl 75% acetonitrile containing 1% formic acid. The resulting eluate or supernate of some of the blank rat plasma samples processed through standard SPE and standard protein precipitation methods were spiked with ketoprofen and propanolol at the level of 100 ng/ml after sample treatment prior to HPLC-MS analysis. The resulting eluate or supernate derived from each test was analyzed by HPLC-MS using the method described in Example 8.

Figure 16:
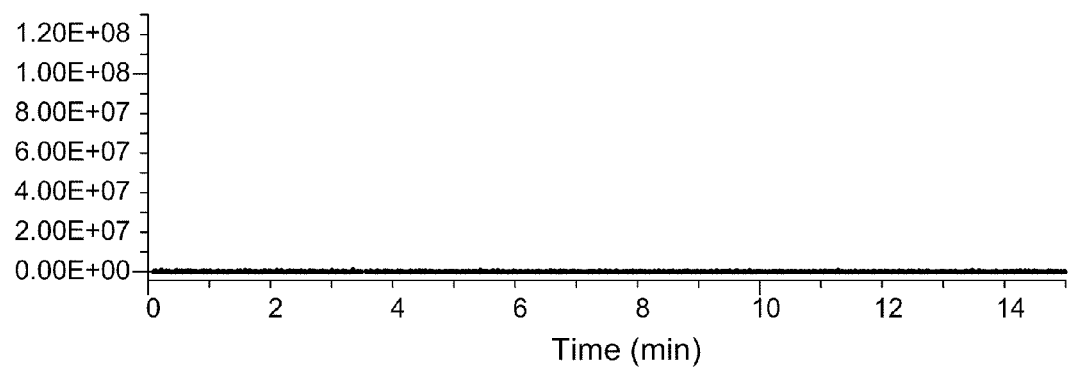
FIG. 16 is an LC-MS diagram of the phospholipid content (m/z 184) of blank rat plasma treated after protein precipitation by zirconia-coated silica SPE filtration.
Figure 17:
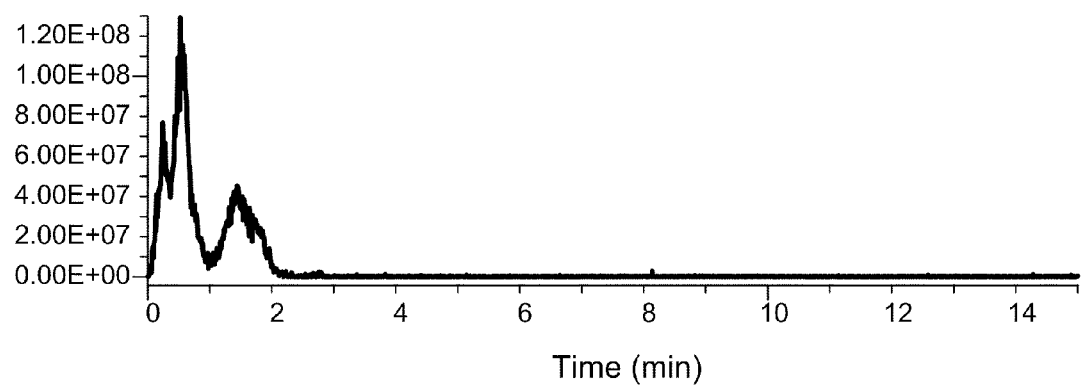
FIG. 17 is an LC-MS diagram comparing the phospholipids content (m/z 184) of blank rat plasma treated using protein precipitation alone.
Figure 18:
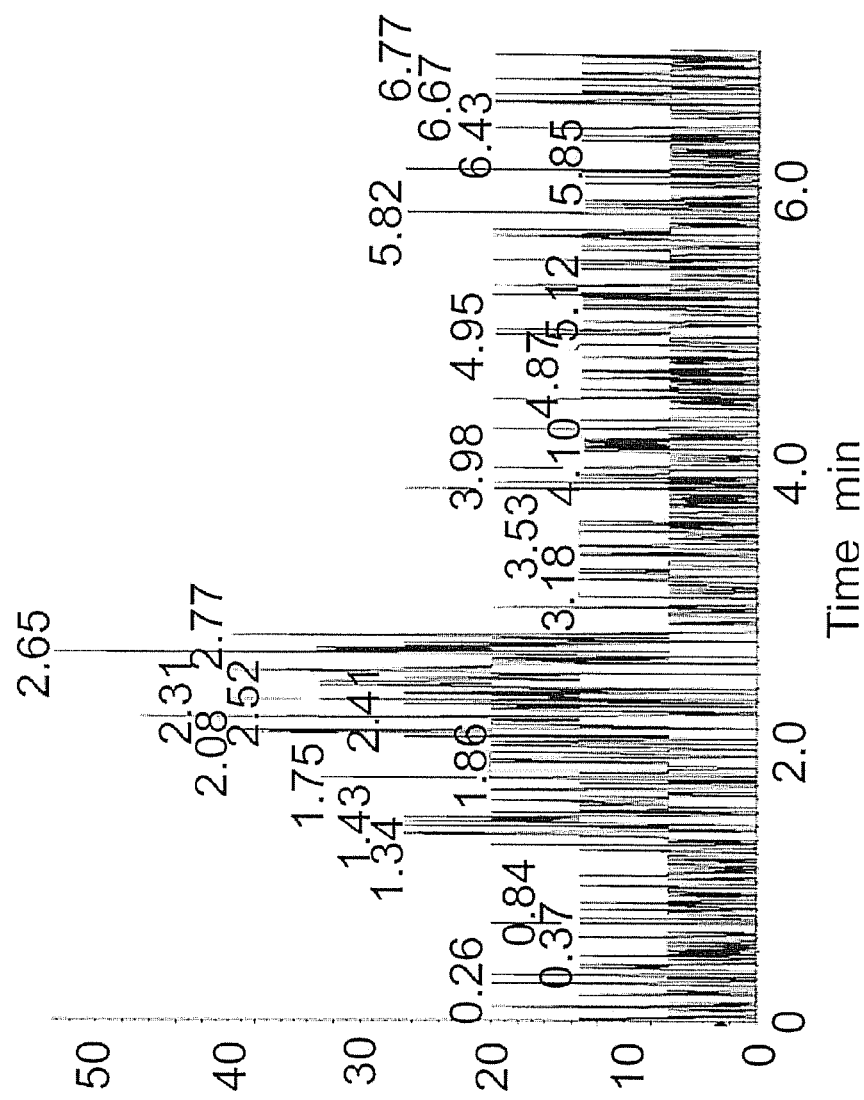
FIG. 18 is an LC-MS diagram (total ion chromatogram) of blank rat plasma processed by the hybrid SPE/protein precipitation method.
Figure 19:
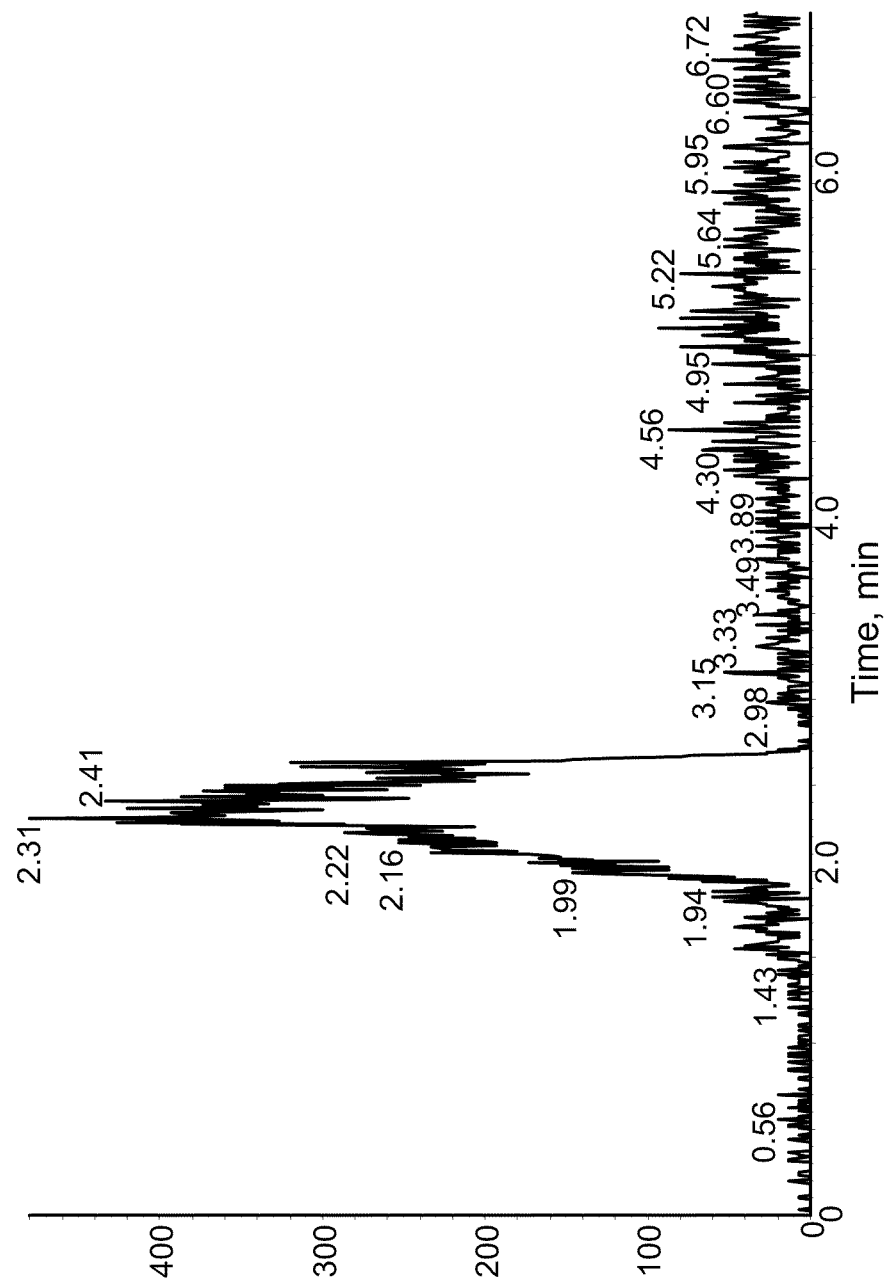
FIG. 19 is an LC-MS diagram (total ion chromatogram) of blank rat plasma processed by standard protein precipitation alone.
Figure 20:
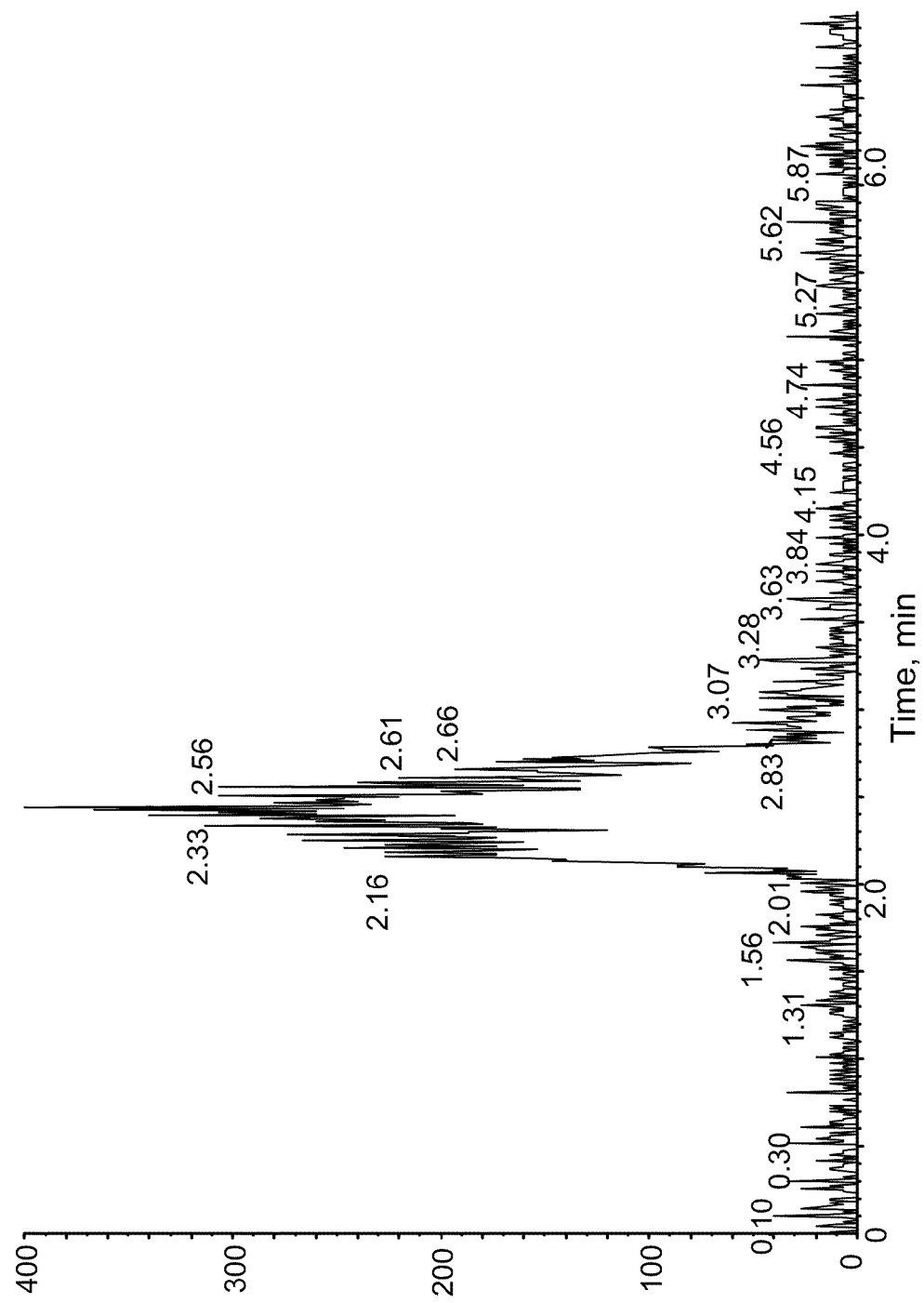
FIG. 20 is an LC-MS diagram (total ion chromatogram) of blank rat plasma processed by standard SPE methodology using Oasis HLB.
Figure 21:
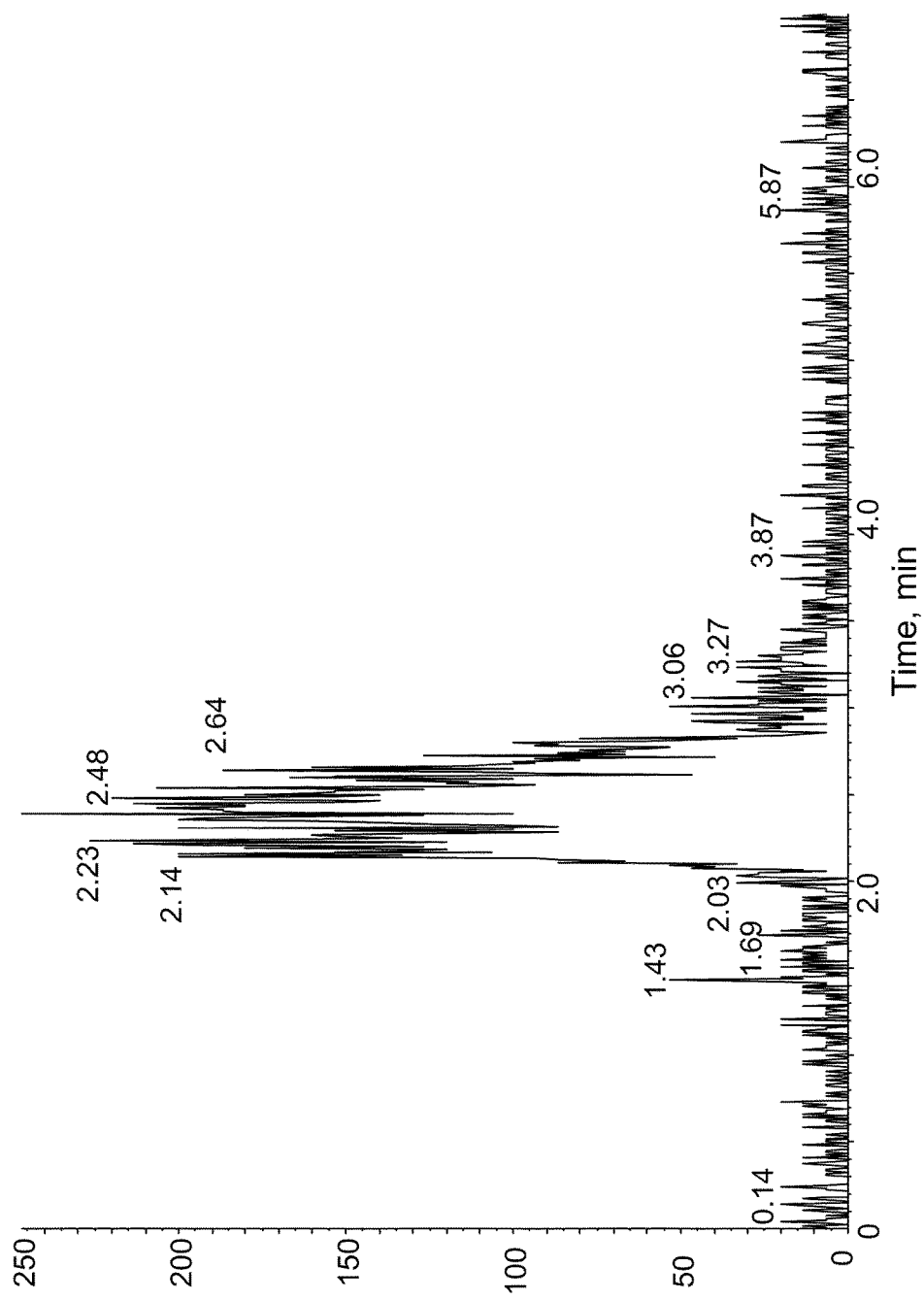
FIG. 21 is an LC-MS diagram (total ion chromatogram) of blank rat plasma processed by standard SPE methodology using YH-OH.
Figure 22:
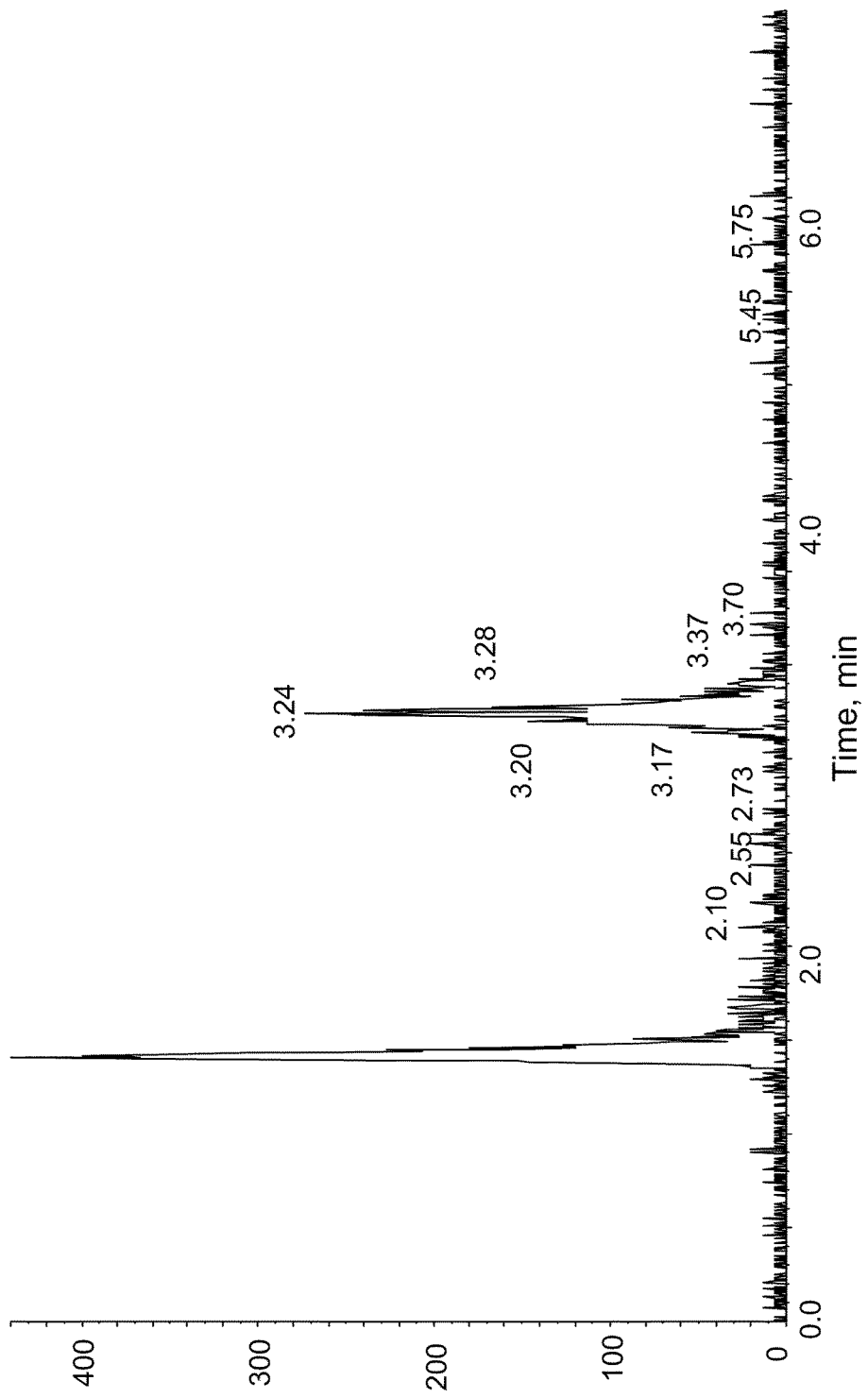
FIG. 22 is an LC-MS diagram (MRM Transitions: propanolol (260.30/116.10) and ketoprofen (255.20/209.10)) of 100 ng/ml ketoprofen and propanolol spiked plasma processed by the hybrid SPE-protein precipitation method.
Figure 23:
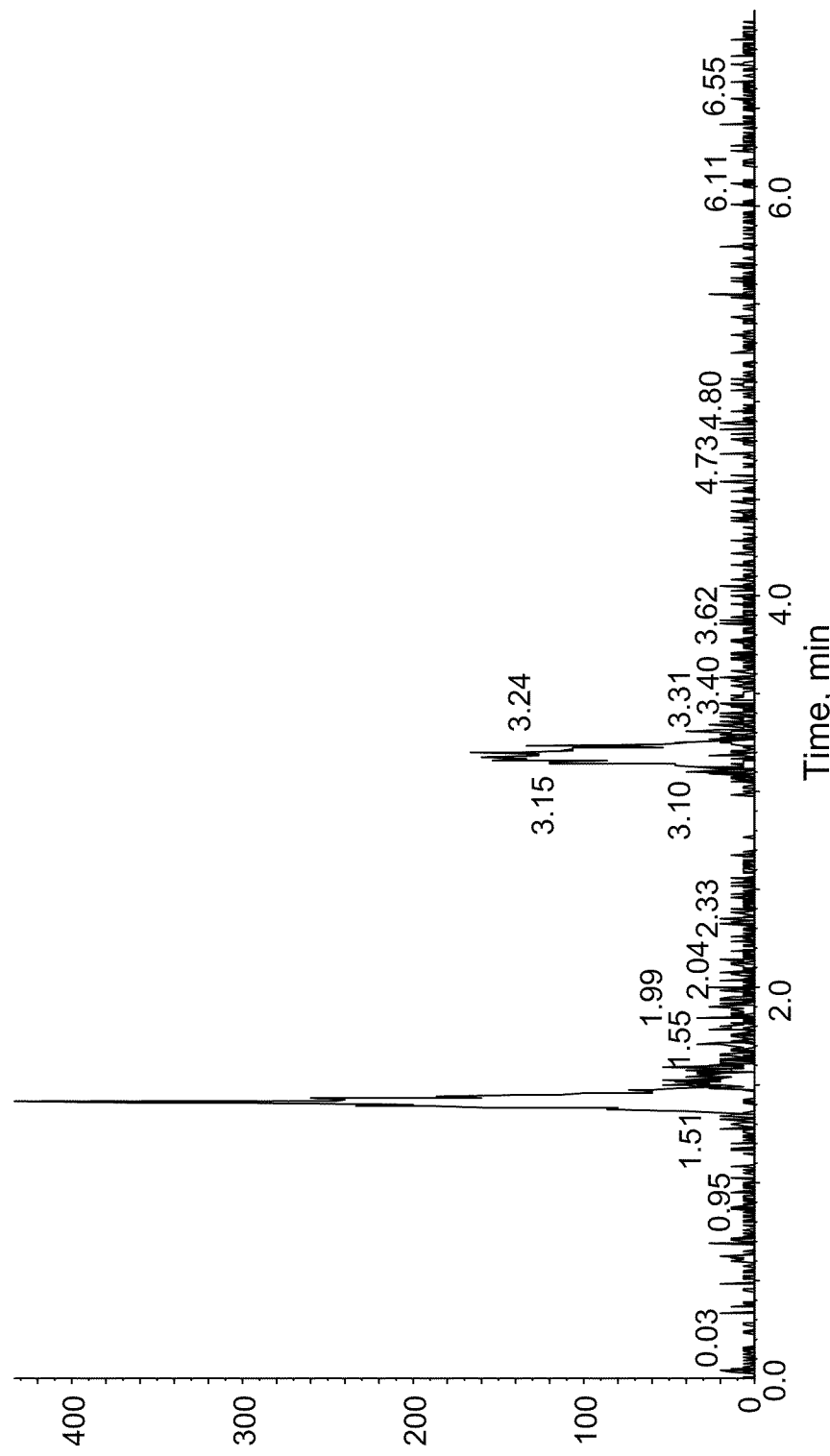
FIG. 23 is an LC-MS diagram (MRM Transitions: propanolol (260.30/116.10) and ketoprofen (255.20/209.10)) of 100 ng/ml ketoprofen and propanolol spiked plasma processed by standard protein precipitation alone.
Figure 24:
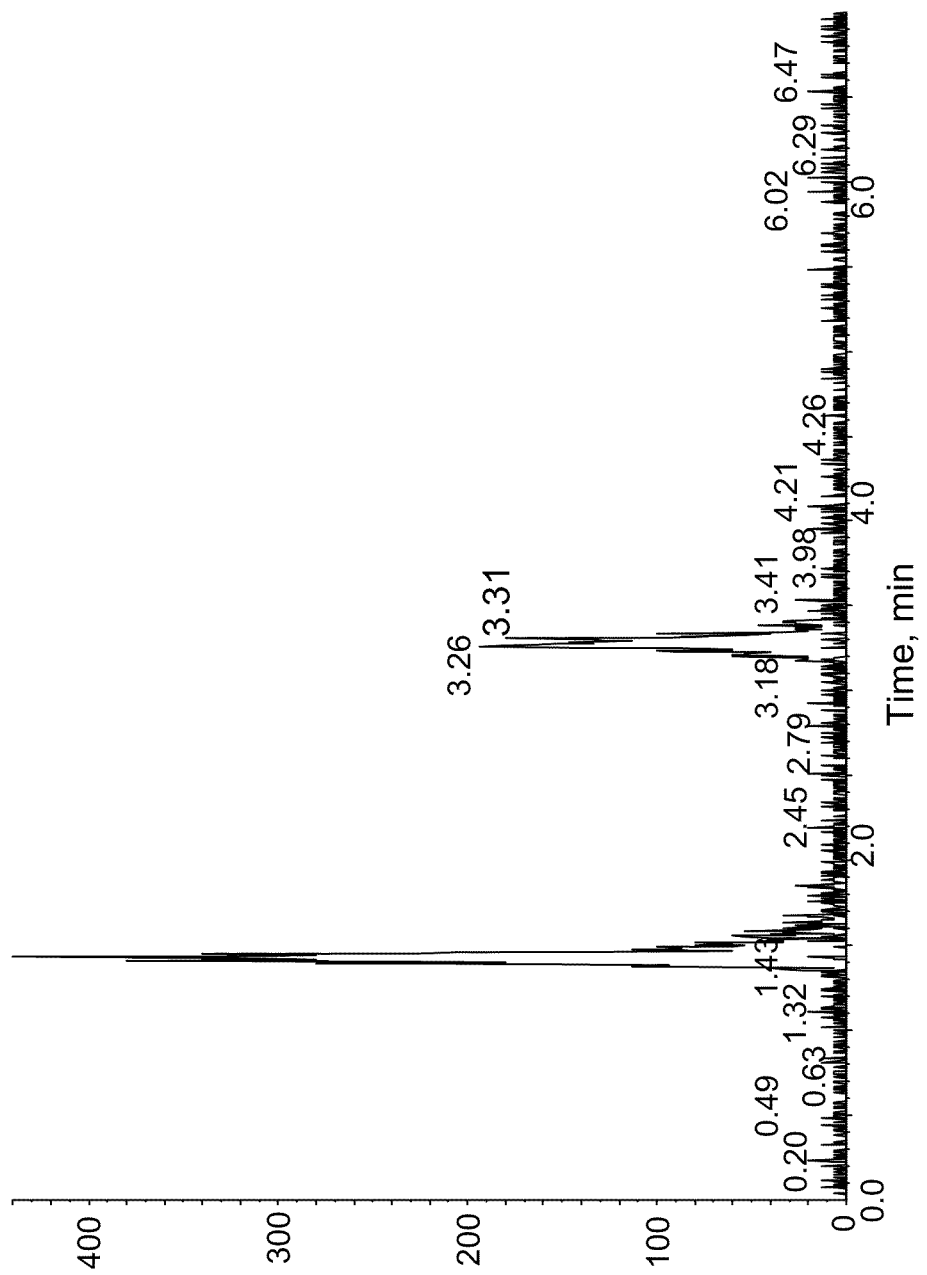
FIG. 24 is an LC-MS diagram (MRM Transitions: propanolol (260.30/116.10) and ketoprofen (255.20/209.10)) of 100 ng/ml ketoprofen and propanolol spiked plasma processed with standard SPE methodology using YH-OH.
Figure 25:
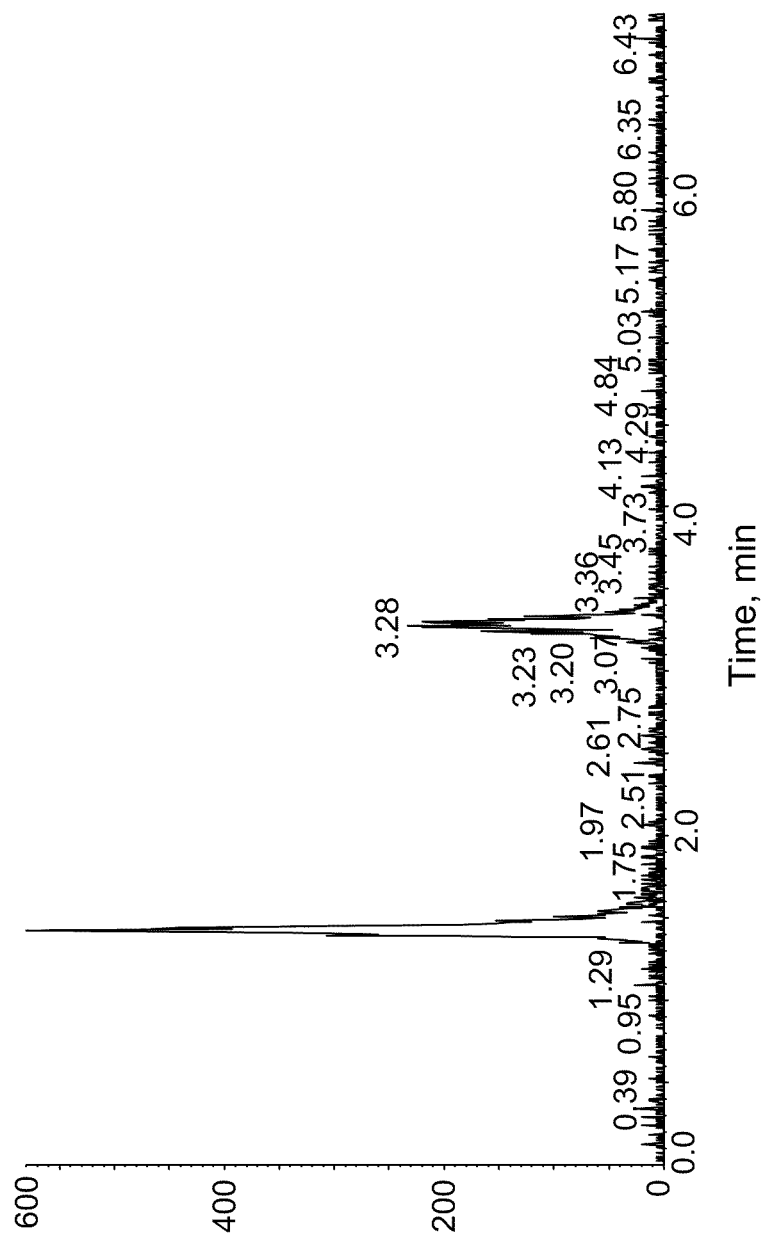
FIG. 25 is an LC-MS diagram (MRM Transitions: propanolol (260.30/116.10) and ketoprofen (255.20/209.10)) of 100 ng/ml ketoprofen and propanolol spiked plasma processed by standard SPE methodology using Oasis HLB.

After sample treatment using one of the four methods described and/or subsequent spiking with the pharmaceutical molecules, all samples were subjected to analysis to determine the absolute recovery of the pharmaceutical compounds achieved using each of the sample treatment methods. Absolute recovery was calculated against an external calibration curve for each of the compounds tested (data not shown). FIG. 16 is an LC-MS diagram (m/z 184) of the blank rat plasma, with no pharmaceutical molecules added, after treatment using the hybrid SPE/protein precipitation method. FIG. 17 is an LC-MS diagram (m/z 184) of the blank rat plasma, with no pharmaceutical molecules added, after treatment using protein precipitation alone. FIG. 18 is an LC-MS diagram (total ion chromatograms) of the blank rat plasma, with no pharmaceutical molecules added, after treatment using the hybrid SPE/protein precipitation method, indicating that all phospholipids and proteins were eliminated from the sample. FIGS. 19, 20, and 21 are LC-MS diagrams (total ion chromatograms) of the blank rat plasma, with no pharmaceutical molecules added, after sample treatment using protein precipitation only, after standard SPE using Oasis HLB media, and after standard SPE using YH-OH media, respectively. These figures indicate that none of the existing methods were as effective as the hybrid SPE/protein precipitation method at eliminating the potentially interfering endogenous sample components, such as proteins and phospholipids, from the bioanalytical samples tested.

Figure 26:
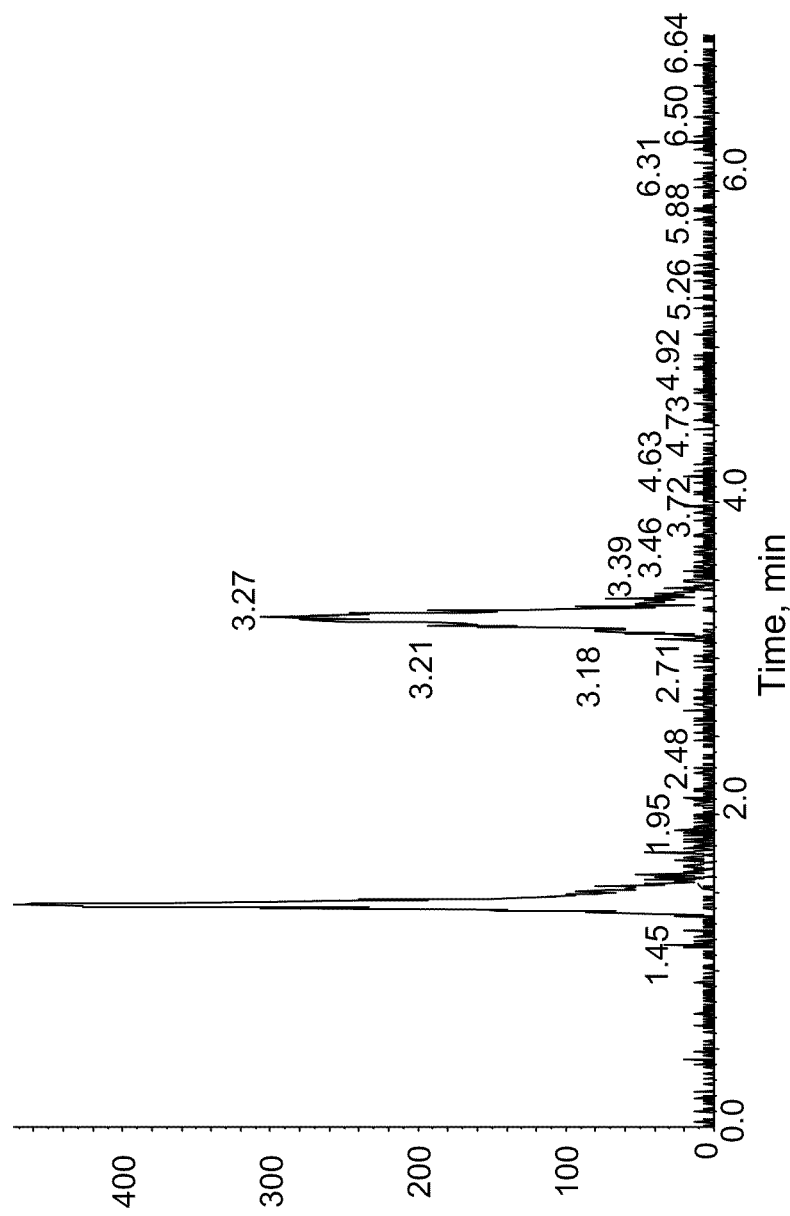
FIG. 26 is an LC-MS diagram (MRM Transitions: propanolol (260.30/116.10) and ketoprofen (255.20/209.10) of 100 ng/ml ketoprofen and propanolol spiked into the eluent of blank rat plasma after treatment with standard SPE methodology using YH-OH.
Figure 27:
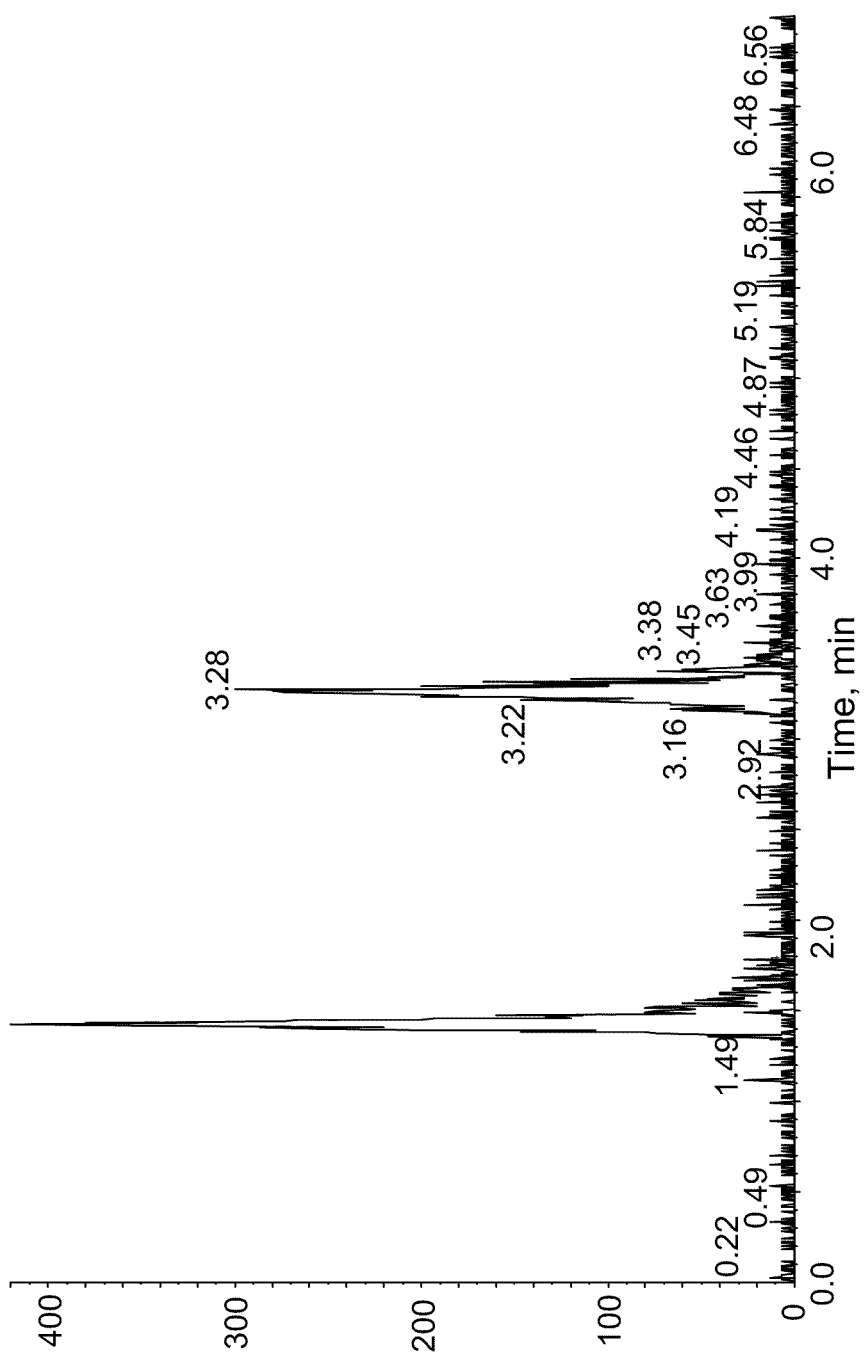
FIG. 27 is an LC-MS diagram (MRM Transitions: propanolol (260.30/116.10) and ketoprofen (255.20/209.10)) of 100 ng/ml ketoprofen and propanolol spiked into the eluent of blank rat plasma after treatment with standard SPE methodology using Oasis HLB.

FIGS. 22, 23, 24, and 25 are LC-MS diagrams (MRM Transitions: propanolol (260.30/116.10) and ketoprofen (255.20/209.10)) of rat plasma with pharmaceutical molecules added prior to sample treatment using the hybrid SPE/protein precipitation method, protein precipitation only, standard SPE using the YHOH media, and standard SPE using the Oasis HLB media, respectively. FIGS. 26 and 27 are HPLC-MS diagrams (MRM Transitions: propanolol (260.30/116.10) and ketoprofen (255.20/209.10)) of rat plasma with pharmaceutical molecules added after SPE sample treatment using the YHOH media, and the Oasis HLB media, respectively. The data resulting from HPLC-MS of the samples spiked with pharmaceutical molecules before and after filtration through the various chromatographic media as described above were analyzed to determine the absolute recovery of analytes after sample treatment. Table 14 shows a summary of these data.

TABLE 14

Comparison of Compound Recovery After Treatment of Samples Using 4 Different Sample Preparation Methods

| Sample Preparation Method | Time of Addition of Pharmaceutical Molecules | Ketoprofen (Acidic) Recovery (% original) | Propanolol (Non-acidic) Recovery (% original) |
| --- | --- | --- | --- |
| Hybrid SPE/Protein Precipitation | Pre-treatment | 82.0% | 68.0% |
| Standard Protein Precipitation | Pre-treatment | 58.8% | 37.0% |
| YHOH SPE | Pre-treatment | 78.4% | 42.0% |
|  | Post-treatment | 89.6% | 82.0% |

TABLE 14-continued

Comparison of Compound Recovery After Treatment of Samples Using 4 Different Sample Preparation Methods

| Sample Preparation Method | Time of Addition of Pharmaceutical Molecules | Ketoprofen (Acidic) Recovery (% original) | Propanolol (Non-acidic) Recovery (% original) |
|---|---|---|---|
| Oasis HLB SPE | Pre-treatment | 76.4% | 44.4% |
| | Post-treatment | 78.4% | 72.0% |

The data summarized in Table 16 indicated that treating the bioanalytical sample using protein precipitation alone recovered the smallest percentage of the pharmaceutical molecules of any treatment tested. Pre-treatment of the bioanalytical samples using the hybrid SPE/protein precipitation method as well as the other two standard SPE treatments yielded a similar level of recovery of the acidic ketoprofen molecules. However, both of the other two standard SPE sample treatments had significant adsorption of the non-acidic propranolol molecules, and required additional steps, such as conditioning, washing, elution, evaporation, and reconstitution, in order to recover propranolol with adequate selectivity prior to HPLC-MS analysis.

The results of this experiment indicated that sample preparation using the hybrid SPE/protein precipitation method was as fast and easy as the standard protein precipitation method, and provided a higher recovery of drug compounds in the bioanalytical samples. The hybrid SPE/protein precipitation method demonstrated a recovery of drug compounds that was comparable to existing SPE sample preparation techniques, and yielded much cleaner samples.

Example 12. Zirconia-Coated Silica SPE Phase was Compared to Ceria-SCX Lanthanide Phase for Effectiveness at Removing Phospholipids from Bioanalytical Samples Experiments were conducted to evaluate the performance of the zirconia-coated silica SPE media in comparison to the lanthanide-loaded strong cation exchange (SCX) SPE media for the treatment of bioanalytical samples. The zirconia-coated silica SPE media was compared to the ceria-loaded SCX SPE media, as well as to the standard SCX SPE media, using the standard protein precipitation sample preparation as a reference, for the effective extraction of phospholipids from rat plasma.

1-ml SPE cartridges were packed with 30 mg of SPE phase, as described in Example 3, using zirconia-coated silica SPE media or SCX SPE media consisting of a benzene sulfonic acid functional group polymerically bonded to 40-60 µM silica particles. In addition, ceria-loaded SCX SPE cartridges were prepared by first packing 1 ml SPE cartridges with SCX SPE as described above. The SCX cartridges were then conditioned with 2 ml methanol followed by 2 ml deionized water with the aid of an SPE vacuum manifold at a flow rate of 1 drop per second. Next, a 2 ml saturated solution of cerium acetate was passed through the cartridge followed by a 2 ml deionized water wash, a 2 ml methanol wash, and vacuum application prior to use.

Rat plasma was subjected to protein precipitation by combining 1 ml of rat plasma with 3 ml of 1% formic acid in acetonitrile followed by 1 minute of agitation and 3 minutes of centrifugation at 15,000 rpm. A 400 µl aliquot of the resulting supernate was passed through each of the SPE cartridges described above at a flow rate of 1 drop per second with the aid of an SPE vacuum manifold.

The phospholipid contents of the resulting eluate from each cartridge were analyzed using HPLC-MS. The HPLC analysis used a ASCENTIS® Express C18 column (Sigma-Aldrich, St. Louis, Mo., USA) with a length of 5 cm, an inner diameter of 2.1 mm, and 2.7 µm particle size. The mobile phase consisted of a 10 mM solution of ammonium acetate in a 95:5 solution of methanol and water. The HPLC was conducted at a temperature of 50° C., a flow rate of 200 µl/min, an injection volume of 10 µl, and a run time of 30 minutes.

The mass spectrometry analysis used an LCQ Ion Trap single quadrupole instrument with the following settings and conditions: ionization: ESI+, capillary (KV): 15, cone (V) 6.0, extractor: 2, RF lens: 0, source temp: 200° C., desolvation temp: 350° C., desolvation gas: 250 l/hr, cone gas: 90 l/hr, monitoring: scan mode from 80-1000 m/z, and extracted ions: m/z 184, 496, 784, 786, and 834. The extracted ions were specific to the major phospholipid ions present in bioanalytical samples.

Figure 28:
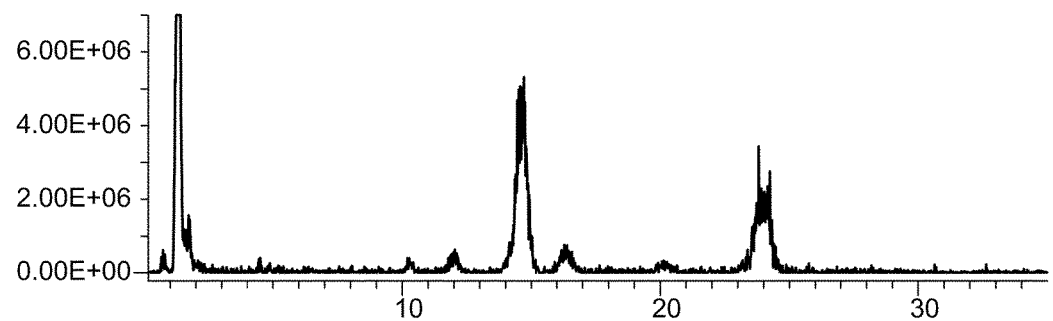
FIG. 28 is an LC-MS diagram of the phospholipids content (extracted ions from total ion chromatogram: m/z 184, 496, 784, 786, and 834) of a rat plasma sample treated using protein precipitation alone.
Figure 29:
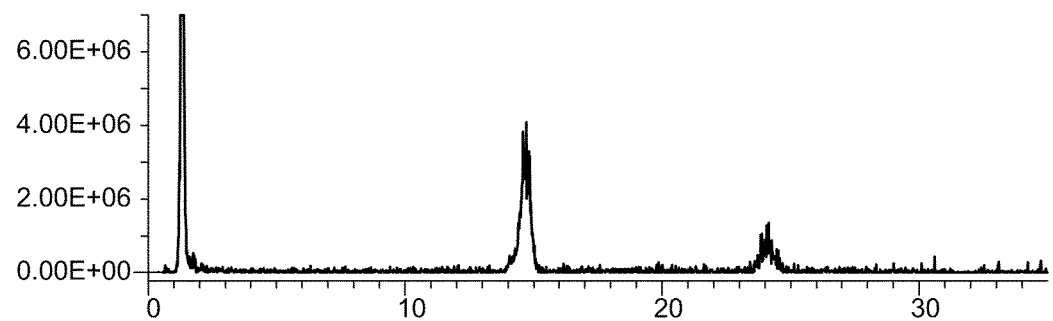
FIG. 29 is an LC-MS diagram of the phospholipids content (extracted ions from total ion chromatogram: m/z 184, 496, 784, 786, and 834) of a rat plasma sample treated using protein precipitation followed by filtration through a SPE cartridge loaded with SCX chromatographic media.
Figure 30:
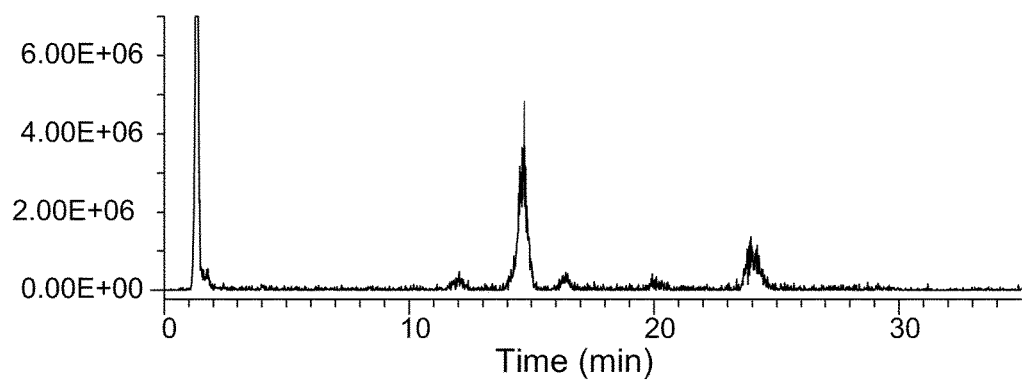
FIG. 30 is an LC-MS diagram of the phospholipids content (extracted ions from total ion chromatogram: m/z 184, 496, 784, 786, and 834) of a rat plasma sample treated using protein precipitation followed by filtration through a SPE cartridge packed with ceria-loaded SCX chromatographic media.
Figure 31:
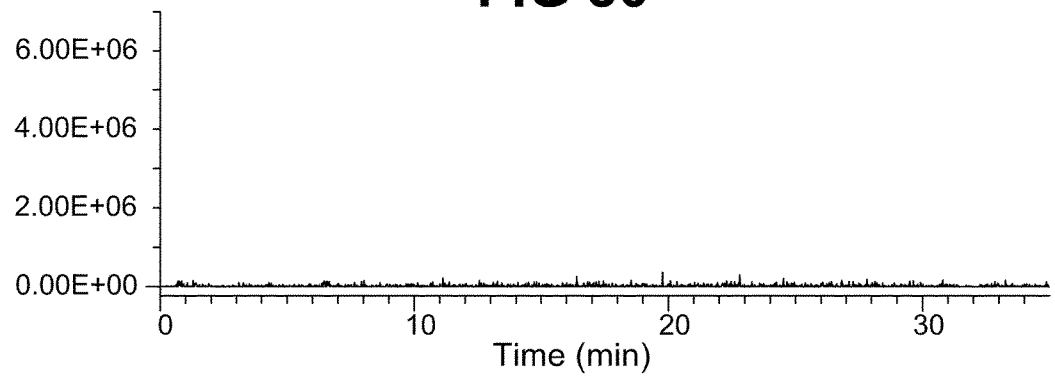
FIG. 31 is an LC-MS diagram of the phospholipids content (extracted ions from total ion chromatogram: m/z 184, 496, 784, 786, and 834) of a rat plasma sample treated using protein precipitation followed by filtration through a SPE cartridge loaded with zirconia-coated silica chromatographic media.

FIG. 28 is an HPLC-MS diagram for the rat plasma sample treated using standard protein precipitation only. FIG. 29 is an HPLC-MS diagram for the protein-precipitated rat plasma sample additionally treated using the SPE cartridge packed with SCX media particles. FIG. 30 is an HPLC-MS diagram for the protein-precipitated rat plasma sample additionally treated using the SPE cartridge packed with ceria-loaded SCX media particles. FIG. 31 is an HPLC-MS diagram for the protein-precipitated rat plasma sample treated using the SPE cartridge packed with zirconia-coated silica SPE media.

The results of the HPLC-MS analysis described above were summarized by comparing the phospholipid content of each treated sample to the phospholipid content of the protein-precipitated sample. The effectiveness of each sample treatment methods was then expressed as a percent of the phospholipids remaining in the protein-precipitated sample, and is summarized in Table 15 below:

TABLE 15

Comparison of Phospholipid Removal from Rat Plasma Samples Using Three Different SPE Phase Media and Protein Precipitation.

| Method of Sample Treatment | Summed m/z area | Phospholipid Removal (% of SPP sample) |
|---|---|---|
| Standard Protein Precipitation (SPP) | 6.04E+11 | 0% |
| SPP + SPE using SCX Media | 2.48E+11 | 58% |
| SPP + SPE using Ce-loaded SCX Media | 2.04E+11 | 66% |
| SPP + SPE using Zirconia-coated Silica Media | 0.00E+00 | 100% |

The results of this experiment determined that the SCX SPE media extracted 58% of the phospholipids from the protein-precipitated rat plasma. The cation exchange functionality of the SCX SPE media created an ionic bond with the zwitterionic polar head group of the phospholipids, resulting in the retention of the phospholipids on the SPE media. Loading the SCX media with ceria slightly improved the performance of the SCX media by boosting the extraction of the phospholipids from the protein-precipitated rat plasma to a level of 66% of the total phospholipids in the plasma. However, the zirconia-coated silica SPE media, with no special loading or other pre-treatment, extracted 100% of the phospholipids from the protein-precipitated rat plasma.

Example 13. The Preparation of SPE Phase by Linking Zirconia to Silica Substrate Via a Single-Layered, Non-Cross-Linked Alkyl Linker was Demonstrated To validate a method of producing a hydrophobic zirconia-coated silica SPE phase that included the zirconia linked to the silica substrate via single-layered and non-cross-linked alkyl linkers, the following experiment was conducted. Briefly, the production of the SPE phase was achieved in two major stages: preparation of the single-layered alkyl linker and attachment of one end of the linker to the silica substrate, and generation and attachment of the zirconia to the free end of the alkyl linker.

Two sizes of porous silica particles were obtained commercially for use as a substrate from one of two suppliers (Davisil Silica, Sigma, St. Louis, USA or Fuji Silysia Chemical, Aichi, Japan). The large Sigma silica particles had a particle size of 250-500 µm, a pore size of 150 Å, and a surface area of 300 $m^2$/g. The small Fuji silica particles had a particle size of 20-45 µm, a pore size of 70 Å, and a surface area of 477 $m^2$/g.

For the alkyl linking agent, a C8 linking agent (1,8-bis(trichlorosilyl)octane, or $Cl_3Si(CH_2)_8SiCl_3$) was obtained (Gelest Inc, Morrisville, Pa., USA). The C8 linking agent had two reactive groups at the two ends of the molecules. The reactive groups at one end of the alkyl linker were to bond to the silica substrate, and the reactive groups at the opposite end were to couple with the zirconia.

The silica particles were pretreated for bonding by placing the particles into a vacuum oven at 120° C. for 16 hours under full vacuum. The dried silica particles were suspended by stirring the particles in toluene with a small amount of chloroform in a 4-neck reaction flask at room temperature. The C8 linking agent was slowly dropped into the reaction flask through a dropping funnel while stirring. The reaction was accelerated by raising the temperature to a reflux temperature of 110° C. The temperature and stirring of the reaction was maintained for 16 hours. The reaction was then cooled down to below 60° C. As a result of the reaction, the surface of the silica particles were coated with a single layer of the C8 linker (trichlorosilyl)octane), with one end bonded to the silica surface and the opposite end available for further reaction or linking purposes.

The zirconia was generated and coupled with the C8 linker layer of the silica particles by slowly dropping zirconium propoxide (Sigma, St. Louis, USA) into the reaction flask, and stirring the mixture at a reflux temperature of 110° C. for 16 hours. The resulting zirconia-C8 coated silica particles were sequentially washed with toluene, dichloromethane, methanol, 50% methanol in water, and finally methanol. The rinsed particles were dried in a vacuum oven at 60° C. for 16 hours, and subsequently stored in a desiccator.

The results of this experiment demonstrated the efficacy of a method of producing a hydrophobic zirconia-coated silica SPE phase consisting of zirconia attached to silica supports via cross-linked C8 linkers.

Example 14. The Preparation of SPE Phase by Linking Zirconia to Silica Substrate Via Multiple-Layered, Cross-Linked Alkyl Linkers was Demonstrated To validate a method of producing a hydrophobic zirconia-coated silica SPE phase that included zirconia linked to silica via multiple-layered and cross-linked alkyl linkers, the following experiment was conducted. Briefly, the production of the SPE phase was achieved in three major stages: preparation of a first single-layered alkyl linker, preparation of an additional layer of alkyl linkers cross-linked to the first alkyl linker layer, and generation and coupling of the zirconia to the free end of the alkyl linker.

Porous silica particles similar to the large particles used in Example 13 (Davisil Silica, Sigma, St. Louis, USA) were pretreated for bonding by placing the silica particles into a vacuum oven at 120° C. for 16 hours under full vacuum. The dried silica particles were suspended by stirring in toluene with a small amount of chloroform and triethylamine in a 4-neck reaction flask at room temperature. The C8 linking agent used previously in Example 13 was slowly dropped into the reaction flask through a dropping funnel. The reaction mixture was stirred at a reflux temperature of 110° C. for 16 hours. The reaction was then cooled down to below 60° C., resulting in silica particles with a single layer of non-cross-linked C8 linkers.

An additional layer of C8 linkers was cross-linked to the single layer of alkyl linkers by adding a small amount of water to the reaction mixture. A mixture of water and propanol (1:2 by volume) was slowly dropped into the reaction flask to initiate the cross-linking of the C8 linkers. The reaction temperature was raised to 110° C. and maintained for 2 hours. The reaction mixture was then cooled down to room temperature.

Zirconia was generated and attached to the free ends of the C8 linkers by slowly dropping zirconium propoxide (Sigma, St. Louis, USA) into the reaction flask and stirred at a reflux temperature of 110° C. for 16 hours. The resulting zirconia/C8-coated silica particles were sequentially washed with toluene, dichloromethane, methanol, 50% methanol in water, and finally methanol. The rinsed particles were dried in a vacuum oven at 60° C. for 16 hours, and subsequently stored in a desiccator.

The results of this experiment demonstrated the efficacy of a method of producing a hydrophobic zirconia-coated silica SPE phase consisting of zirconia attached to silica supports via multiple layers of cross-linked C8 linkers.

Example 15. The Preparation of SPE Phase by Linking Zirconia to Silica Substrate Via Multiple-Layered, Cross-Linked Alkyl Linkers Using a Second Method was Demonstrated To validate a method of producing a hydrophobic zirconia-coated silica SPE phase that included zirconia linked to silica via multiple-layered and cross-linked alkyl linkers, the following experiment was conducted. Briefly, the production of the SPE phase was achieved in three major stages: preparation of a first single-layered alkyl linker, preparation of an additional layer of alkyl linkers cross-linked to the first alkyl linker layer, and generation and attachment of the zirconia to the free end of the alkyl linker.

35 g of small porous silica particles similar to the Fuji particles used in Example 13 (Fuji Silysia Chemical, Aichi, Japan) were placed into a 4-neck reaction flask with an attached Dean and Stark water trap and condenser, thermocouple, and overhead stirrer. The small silica particles were suspended by stirring in toluene at room temperature. The temperature of the suspension was increased to a reflux temperature of 110° C. and toluene was allowed to distill into the water trap. The water trap was drained for a first time and then allowed to refill by allowing reflux to continue for an additional hour. The mixture was then cooled to room temperature and the water trap was drained a second time.

After cooling to room temperature, 2.5 g of water was added to the mixture, followed by two hours of stirring. 5 mL of triethylamine was then added to the mixture, followed by the slow addition of 50 mL of 1,8-bis(trimethoxysilyl)octane using a dropping funnel while continuously stirring. The temperature of the reaction mixture was increased to 60° C. and stirred overnight.

After reacting overnight, the temperature control of the flask was set to 100° C., and the stopcock of the Dean and Stark water trap was opened. As the reaction mixture heated up, methanol produced in the reaction and triethylamine residue in the reaction mixture distilled into the water trap. Distillate from the reaction mixture was collected in the water trap until the reaction mixture reached a temperature of 100° C. Once a temperature of 100° C. was achieved, the stopcock of the Dean and Stark water trap was closed and the reaction proceeded in the flask at this temperature for 2 hours. A slight positive nitrogen pressure was introduced and maintained during all steps of this process.

The temperature control of the flask was increased to 110° C. and toluene was allowed to distill into the water trap. The water trap was filled and drained a total of 4 times. The reaction mixture in the flask was then cooled to room temperature (35° C.). A dry addition funnel was attached to the flask and 51 g of zirconium propoxide solution in isopropanol was slowly added. The reaction mixture was maintained at this temperature and stirred for 2 hours, and then heated to 110° C. and stirred overnight.

The reaction mixture was cooled to 70° C. prior to filtration. The reaction solvent was decanted and the silica particles were rinsed in the flask with toluene, and the rinse toluene was decanted. Fresh toluene was added to the flask and the toluene-silica mixture was transferred to the filtration funnel. In the funnel, the silica was washed sequentially using toluene, dichloromethane, methanol, water, 1% formic acid in water, a 1:1 water-methanol mixture, and finally methanol. After filtration, the filtration funnel was aspirated for an additional hour. The filtered silica was dried in a vacuum oven at 80° C. overnight, and the dried material was stored in a desiccator.

The results of this experiment demonstrated the efficacy of a second method of producing a hydrophobic zirconia-coated silica SPE phase consisting of zirconia attached to silica supports via multiple layers of cross-linked C8 linkers.

Example 16. The Preparation of SPE Phase by Bonding Both Alkyl Chains and Zirconia Directly to a Silica Substrate was Demonstrated To validate a method of producing a hydrophobic zirconia-coated silica SPE phase that included both zirconia and an alkyl linker directly bonded to silica, the following experiment was conducted.

50 g of silica similar to the small Fuji particles described in Example 13 were suspended in toluene in a 4-neck flask with an attached Dean and Stark water trap and condenser, thermocouple and overhead stirrer. The temperature control was set to a reflux temperature of 110° C. and toluene was distilled into the trap. After draining the trap once, distillation of the toluene was continued for an additional hour. The reaction mixture was then cooled to 70° C. and the trap was drained for a second time.

Imidazole was ground with mortar and pestle, and 5.4 g of the imidazole powder was added to the cooled reaction mixture, followed by 14.3 mL of octydecylchlorodimethylsilane. The reaction mixture was stirred at 110° C. overnight.

The reaction mixture was cooled to 70° C. prior to filtration. The reaction solvent was decanted and the silica particles were rinsed in the flask with toluene, and the rinse toluene was decanted. Fresh toluene was added to the flask and the toluene-silica mixture was transferred to the filtration funnel. In the funnel, the silica was washed sequentially using toluene, methanol, a 1:1 methanol:water mixture, and finally methanol. After filtration, the filtration funnel was aspirated for an additional hour. The filtered silica was dried in a vacuum oven at 90° C. overnight, yielding silica particles with a single coating of C18 linkers with no reactive groups on the exposed ends of the linkers.

An addition funnel was dried in the vacuum oven at 130° C., and used to transfer the C18-coated silica particles into a clean 4-neck reaction flask with similar attachments to the first flask described previously. The silica was suspended in toluene within the flask, and the flask was flushed with nitrogen. While maintaining a slight positive nitrogen pressure within the flask, the reaction mixture was heated to a reflux temperature of 110° C. and toluene was distilled into the trap. After filling and draining the trap two times, the reaction mixture was cooled to a room temperature of 35° C.

Zirconium propoxide was added slowly to the reaction mixture over a period of one hour through an dry addition funnel attached to the flask. The reaction mixture was stirred at room temperature for three hours, and then the reaction mixture was stirred continuously at a temperature of 110° C. overnight.

The reaction mixture was again cooled to 70° C. prior to a second round of filtration and rinsing. The reaction solvent was decanted and the silica particles were rinsed in the flask with toluene, and the rinse toluene was decanted. Fresh toluene was added to the flask and the toluene-silica mixture was transferred to the filtration funnel and aspirated for one hour.

The dried silica was transferred to another reaction flask and stirred for one hour in 300 mL of 1% formic acid solution in water. The upper fluid layer containing residual toluene was extracted from the flask, and 100-200 mL of additional water (100-200 mL) was added and stirred for an additional hour. The upper fluid layer containing residual toluene was extracted from the flask a second time.

The reaction mixture was filtered through a filtration funnel and rinsed with water followed by methanol. After filtration, the filtration funnel was aspirated for an additional hour. The filtered silica was dried in a vacuum oven at 80° C. overnight, yielding a silica particle with C18 alkyl chains and zirconia bonded directly to the surface of the particle, as illustrated in FIG. 32B.

The results of this experiment demonstrated a method for producing a hydrophobic zirconia-coated silica SPE phase that included both zirconia and a C18 alkyl linker directly bonded to a silica particulate substrate.

Example 17. The Removal of Phospholipids from Biological Samples Using Hydrophobic PVDF Membranes was Evaluated To demonstrate the efficacy of hydrophobic PVDF membrane adsorbents at removing phospholipids from biological samples, the following experiments were conducted.

Bovine plasma was subjected to a protein precipitation process in which the plasma was contacted with a solution of 1% ammonium formate in methanol, and then centrifuged at 5000 g for 10 minutes. The protein-precipitated supernate was divided into 100 μL samples and subjected to one of three additional sample treatments prior to LC-MS analysis:

1) no treatment (control); 2) vortex mixing with a single polyvinyldifluoride (PVDF) membrane for 10 minutes; and 3) vortex mixing with two PVDF membranes for 10 minutes.

Each sample was subjected to LC/MS analysis performed on an Agilent 1100 HPLC (Agilent Technologies, Inc., Santa Clara, Calif., USA) with QTRAP 3200 mass spec (Applied Biosystems, Forster City, Calif., USA). Chromatographic separation of each sample was carried out using an Ascentis Express RP-Amide HPLC column (Sigma, St. Louis, Mo., USA) at a flow rate 200 µL/min. This column had a length of 5 cm and an inner diameter of 2.1 mm and was packed with 2.7 µm particles. The phospholipids were monitored at MRM transitions 184/184 and 104/104 after in-source fragmentation.

Figure 33:
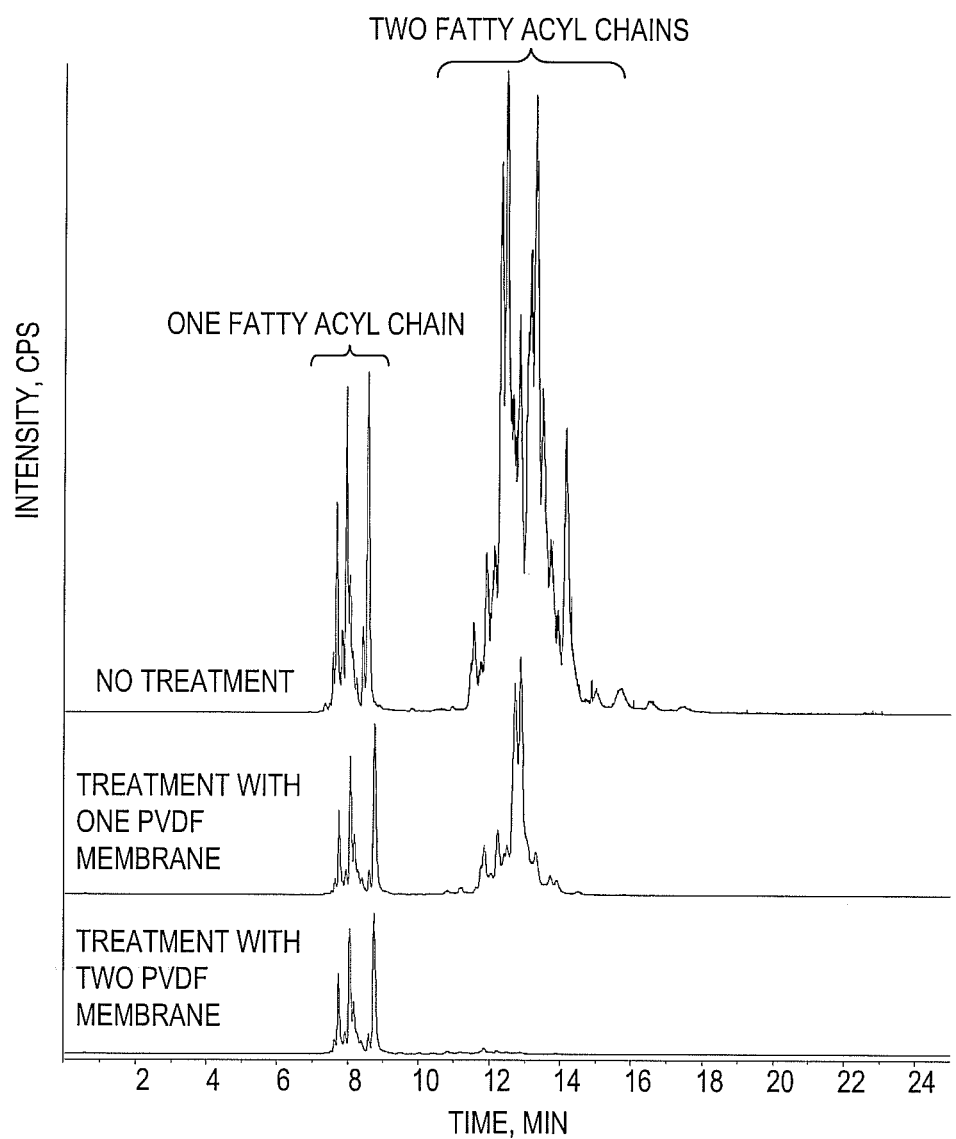
FIG. 33 are LC-MS diagrams of the lipids content in bovine plasma samples before and after treatment with one or two PVDF membranes.

The results of the LC/MS analysis of the treated bovine plasma samples are summarized in FIG. 33. The signals produced by the double-chain phospholipids eluted at about 11-15 minutes decreased due to treatment with either one or two PVDF membranes, indicating the removal of these phospholipids from the PVDF-treated samples. However, the signals produced by the single-chain phospholipids at about 7-9 minutes were relatively unchanged when treated with either one or two PVDF membranes.

The results of this experiment demonstrated that the treatment of protein-precipitated bovine plasma samples using multiple PVDF membranes was highly effective at removing double-chain phospholipids from the samples, but was significantly less effective at removing single-chain phospholipids from the same samples.

Example 18. The Removal of Phospholipids from Biological Samples Using Hydrophobic Zirconia-Coated SPE Media was Evaluated To demonstrate the efficacy of hydrophobic zirconia-coated silica adsorbents at removing phospholipids from biological samples, the following experiments were conducted.

25 µL samples of bovine plasma were subjected to a protein precipitation process similar to the process described in Example 17. The protein-precipitated supernate was subjected to one of two additional sample treatments prior to LC-MS analysis: 1) no treatment (control); 2) vortex mixing with a 30 mg of the large hydrophobic zirconia-coated silica particles similar to the particles produced in Example 14. These particles included zirconia attached to the silica by coupling to the free ends of cross-linked C8 alkyl chains. The silica had a particle size of about 250-500 µm.

Figure 34:
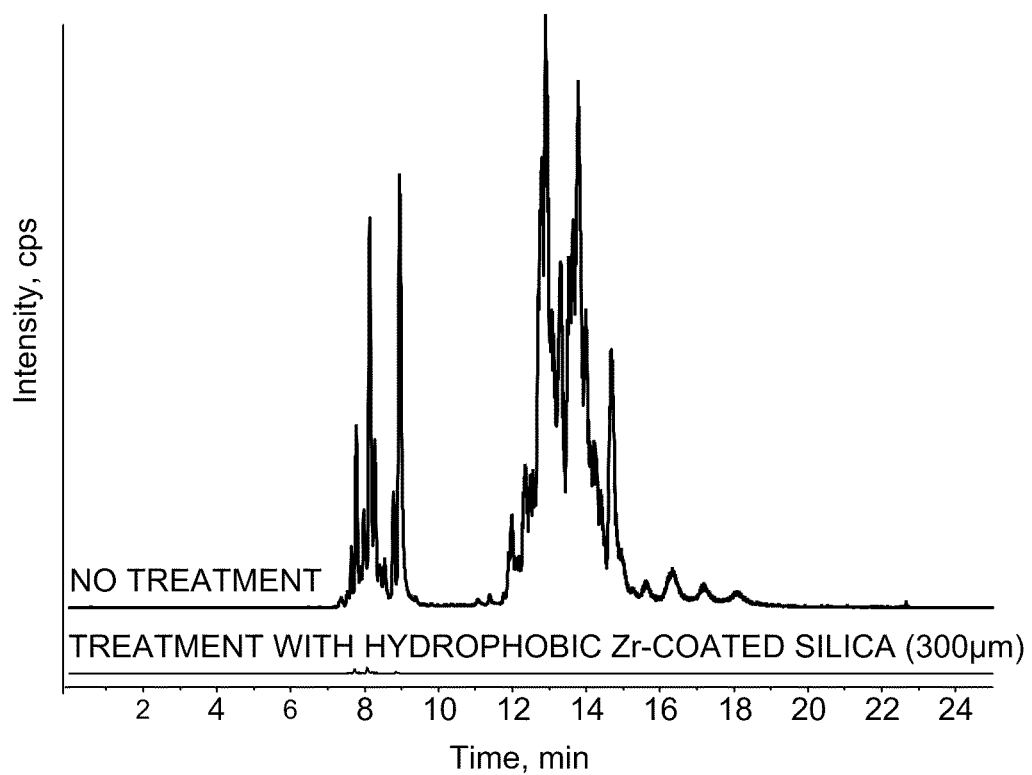
FIG. 34 are LC-MS diagrams of the phospholipid content in bovine plasma samples before and after treatment with hydrophobic zirconia-coated sorbents

LC/MS analysis was performed on the samples using methods similar to those described in Example 17, and the results of this analysis are summarized in FIG. 34. The signals produced by both the double-chain phospholipids at about 11-15 minutes and the single-chain phospholipids at about 7-9 minutes were reduced due to treatment with the Hybrid SPE particles. Quantitatively, the hydrophobic zirconia-coated silica adsorbents removed 99% single-chain phospholipids and 100% of the double-chain phospholipids from the protein-precipitated bovine plasma samples.

In addition, a similar experiment was conducted with a range of volumes (25, 50, and 100 µL) of protein-precipitated bovine plasma samples treated similarly to the previous samples, using the same 30 mg quantity of hydrophobic zirconia-coated silica adsorbents. Table 16 summarizes the overall results of this experiment.

TABLE 16

Comparison of Phospholipid Removal from Bovine Plasma Samples.

| Sample | Phospholipids Removed (% Untreated) | | |
|---|---|---|---|
| Volume (µL) | Single-chain Phospholipids | Double-chain Phospholipids | Total |
| 25 | 96.6% | 100.0% | 99.1% |
| 50 | 88.9% | 99.5% | 96.6% |
| 100 | 63.8% | 98.0% | 88.9% |

The hydrophobic zirconia-coated silica adsorbents removed nearly all of the double-chain phospholipids from all volumes of the bovine plasma samples, although the percentage of double-chain phospholipids removed decreased slightly for the larger sample volumes. The amount of single-chain phospholipids removed by the hydrophobic zirconia-coated silica adsorbents declined more sharply for larger sample volumes. The particular composition of hydrophobic zirconia-coated silica adsorbents used in this experiment may be more sensitive to saturation effects for the capture of single-chain phospholipids compared to the capture of double-chain phospholipids.

The results of this experiment demonstrated that the treatment of protein-precipitated bovine plasma samples using hydrophobic zirconia-coated silica adsorbents that had zirconia attached to the silica via cross-linked C8 alkyl chains was effective at removing both single-chain and double-chain phospholipids from the protein-precipitated bovine plasma samples.

Example 19. The Removal of Phospholipids from Biological Samples Using Hybrid SPE Media (Zirconia Alone Bonded to Silica) was Evaluated To compare the efficacy of bare silica and zirconia alone bonded to silica particles (Hybrid SPE) at removing phospholipids from biological samples, the following experiments were conducted.

25 µL samples of bovine plasma were subjected to a protein precipitation process similar to the process described in Example 17. The protein-precipitated supernate was subjected to one of four additional sample treatments prior to LC-MS analysis: 1) no treatment (control); 2) vortex mixing with 30 mg of bare (uncoated) 300-µm silica particles; 3) vortex mixing with 30 mg of the Hybrid SPE with a small particle size of 20 µm; and 4) vortex mixing with 30 mg of the Hybrid SPE particles with a large particle size of 300 µm.

Figure 35:
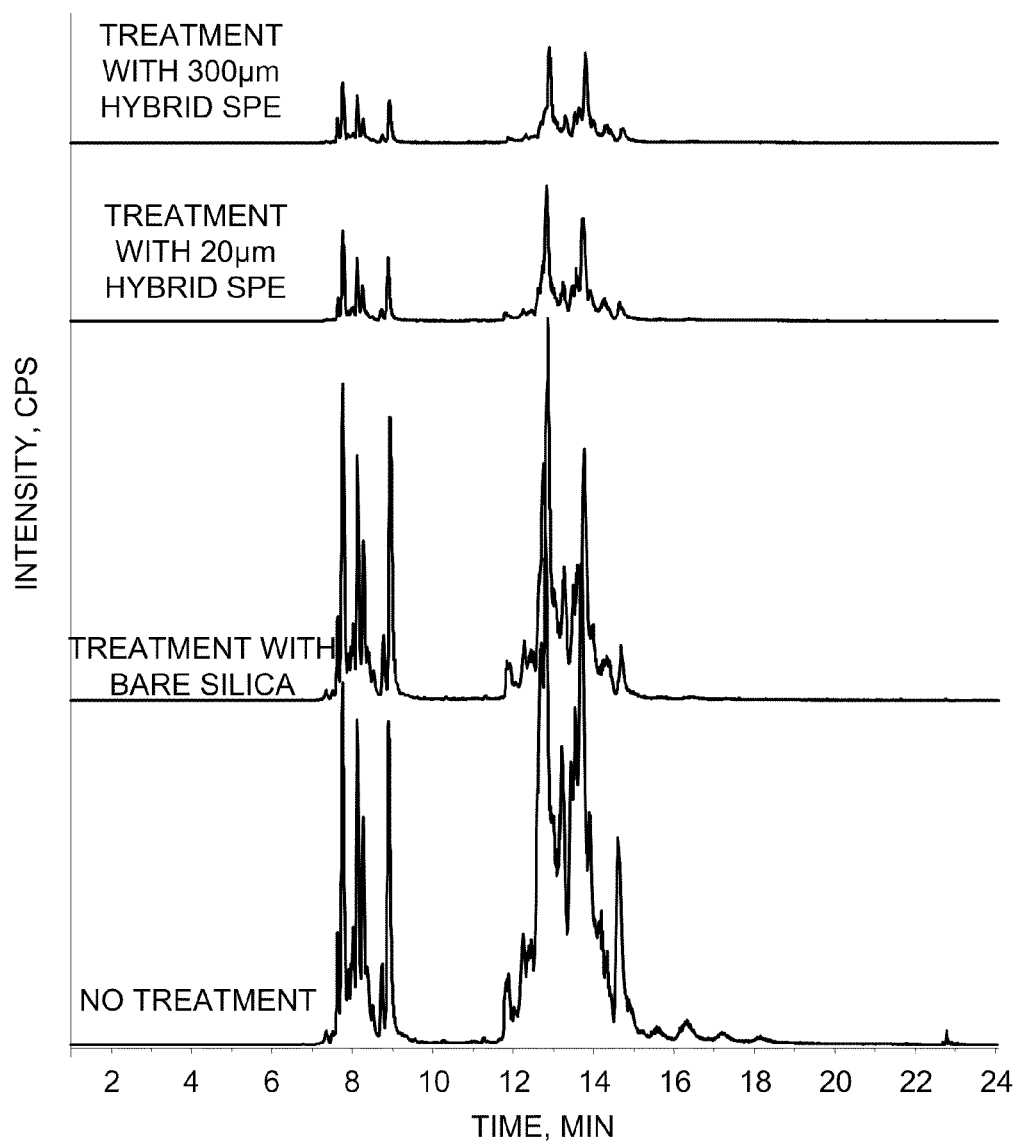
FIG. 35 is an LC-MS diagram of the phospholipids content in bovine plasma samples before and after treatment with bare silica, zirconia coated on 20 µm silica, and zirconia coated on 300 µM silica.

LC/MS analysis was performed on the samples, and the results of this analysis are summarized in FIG. 35. The total concentrations of single-chain and double-chain phospholipids were reduced by 50% after treatment with bare silica particles. After treatment with the small (20 µm) and large (300-µm) Hybrid SPE adsorbents, the total phospholipid concentration was reduced by 86% and 89%, respectively. By comparison, the hydrophobic zirconia-coated silica particles removed 99.1% of the total phospholipids from a similar 25-µL bovine plasma sample, as summarized in Table 16 above. Further, the same amount of hydrophobic zirconia-coated silica adsorbents removed about 97% of the total phospholipids from 50-µL bovine plasma samples that were twice the volume of the samples treated in this experiment.

The results of this experiment demonstrated that the neither of the Hybrid SPE adsorbents nor the bare silica adsorbent were as effective at removing phospholipids from biological samples as the hydrophobic zirconia-coated silica adsorbent composition.

Example 20. The Efficacy of Hydrophobic Zirconia-Coated SPE Particles at the Removal of Glycerides was Evaluated To evaluate the efficacy of hydrophobic zirconium oxide adsorbents at removing glycerides from biological samples, the following experiments were conducted.

A series of stock glyceride solutions containing monoleins, dioleins, and trioleins dissolved in solutions of acetonitrile in water at various concentrations were formed. The compositions of the stock glyceride solutions are summarized in Table 17.

TABLE 17

Stock Glyceride Solutions Treated with Adsorbents.

| Glyceride in Solution | Glyceride Concentration (µg/mL) | Solvent Composition (% volume) | |
|---|---|---|---|
| | | Acetonitrile | Water |
| monoolein | 75-100 | 100% | 0% |
| | | 90% | 10% |
| | | 75% | 25% |
| diolein | 150-200 | 100% | 0% |
| | | 90% | 10% |
| | | 75% | 25% |
| triolein | 75-100 | 100% | 0% |
| | | 90% | 10% |

1-mL samples taken from each of the stock glyceride samples described in Table 17 were combined with 25 mg of the hydrophobic zirconia-coated silica SPE particles having various compositions as described in Table 18: adsorbent A produced using the procedure described in Example 14, adsorbent B was produced by procedure described in Example 23, adsorbent C produced using the procedure described in Example 15, and adsorbent D produced using the procedure described in Example 24. Each mixture was shaken by hand for 1 min and then centrifuged at 10000 rpm for 2 min. The top supernatant layer was decanted into an HPLC vial and analyzed for the presence of glycerides using HPLC and an Evaporative Light Scattering Detector. A calibration curve for quantitation was made using 20 µg/mL to 200 µg/mL solutions of each of the glycerides in 90% acetonitrile and 75% acetonitrile. The concentration of glycerides in the each of the supernates was calculated using the appropriate calibration curve. The amount of glycerides removed from each sample was determined by subtracting the concentration of glycerides in the supernates from the original sample concentration.

Additional adsorbents were obtained and combined with 1-mL samples taken from the stock glycerides, and the amount of glyceride removed from each sample was determined in a similar manner to the measurements described for the hydrophobic zirconia-coated silica particles. The additional adsorbents included zirconia-coated silica particles similar to those produced in Example 1, alumina particles (Supelco, Bellefonte, Pa., USA), bare silica (Supelco, Bellefonte, Pa., USA), aminopropyl silica (Supelco, Bellefonte, Pa., USA), PSA (primary secondary amine, Supelco, Bellefonte, Pa., USA), Lipid Removal Agent (calcium silicate hydrate, Supelco, Bellefonte, Pa., USA), octadecyl-coated silica (Supelco, Bellefonte, Pa., USA), and a combination of the zirconia-coated silica particles and the Hybrid SPE, and a mixture of octadecyl-coated silica and the zirconia-coated silica. The composition, physical characteristics, and amounts of all adsorbents combined with the 1-mL stock glycerine samples are summarized in Table 18.

TABLE 18

Adsorbents Combined With 1-mL Glyceride Samples.

| Adsorbent (Abbreviation in Figures) | Amount Added (mg) | Particle Size (µm) | Pore Size (Å) | Surface Area (m$^2$/g) |
|---|---|---|---|---|
| Silica with Zirconia Attached to Free End of C8 Linker (A) | 25 | 300 | 150 | 300 |
| Silica with Zirconia Attached to Free End of C8 Linker (B) | 25 | 300 | 150 | 300 |
| Silica with Zirconia Attached to Free Ends of Cross-Linked C8 Linkers (C) | 25 | 60 | 70 | 477 |
| Silica with Zirconia and C18 Attached Independently (D) | 25 | 60 | 70 | 477 |
| Zirconia-Coated Silica (Hybrid SPE) | 25 | 40-60 | 30 | 100 |
| Alumina (Alumina) | 25 | 40-250 | 58 | 155 |
| Bare Silica (Silica) | 25 | 31-80 | 66 | 500 |
| Aminopropyl Silica (NH$_2$) | 25 | 31-80 | 66 | 500 |
| Primary Secondary Amine (PSA) | 25 | 40-75 | 70 | 480 |
| Lipid Removal Agent/Calcium Silica Hydrate (LRA) | 25 | — | — | 120 |
| Octadecyl-Coated Silica (C18) | 25 | 31-80 | 66 | 500 |
| Zirconia-Coated Silica + Octadecyl-Coated Silica (Hybrid + C18) | 50 | 20-45/31-80 | 30/66 | 100/500 |

Figure 36:
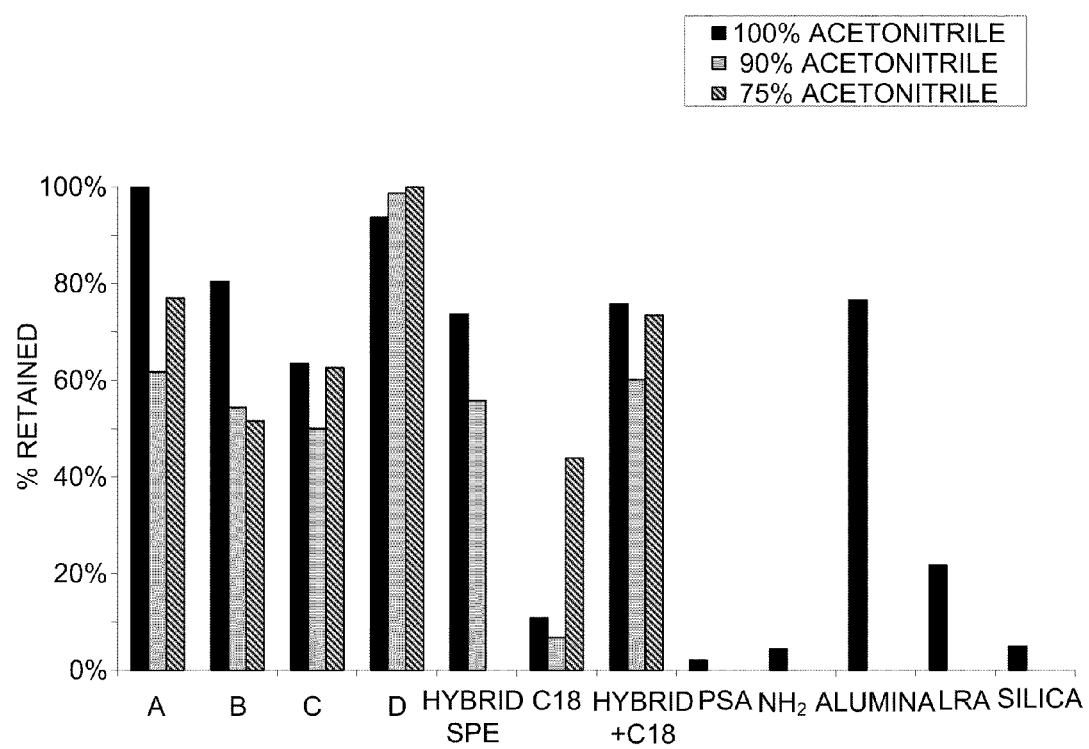
FIG. 36 is a comparison of the amount of monoglycerides retained by twelve different exemplary SPE media compositions.

The amount of monoglyceride (monoolein) removed from each sample by the various adsorbent compositions is summarized in FIG. 36 for the three different sample compositions. All of the materials the included both zirconia and hydrophobic alkyl groups (adsorbents A, B, C, D, and the mixture of zirconia-coated silica and octadecyl-coated silica) achieved greater than 50% removal of the monooleins in the sample for all sample compositions ranging from 75% to 100% acetonitrile solvent. The particles having zirconia and C18 groups attached separately to the same silica substrate retained more than 90% of the monoglycerides in all three sample compositions.

Figure 37:
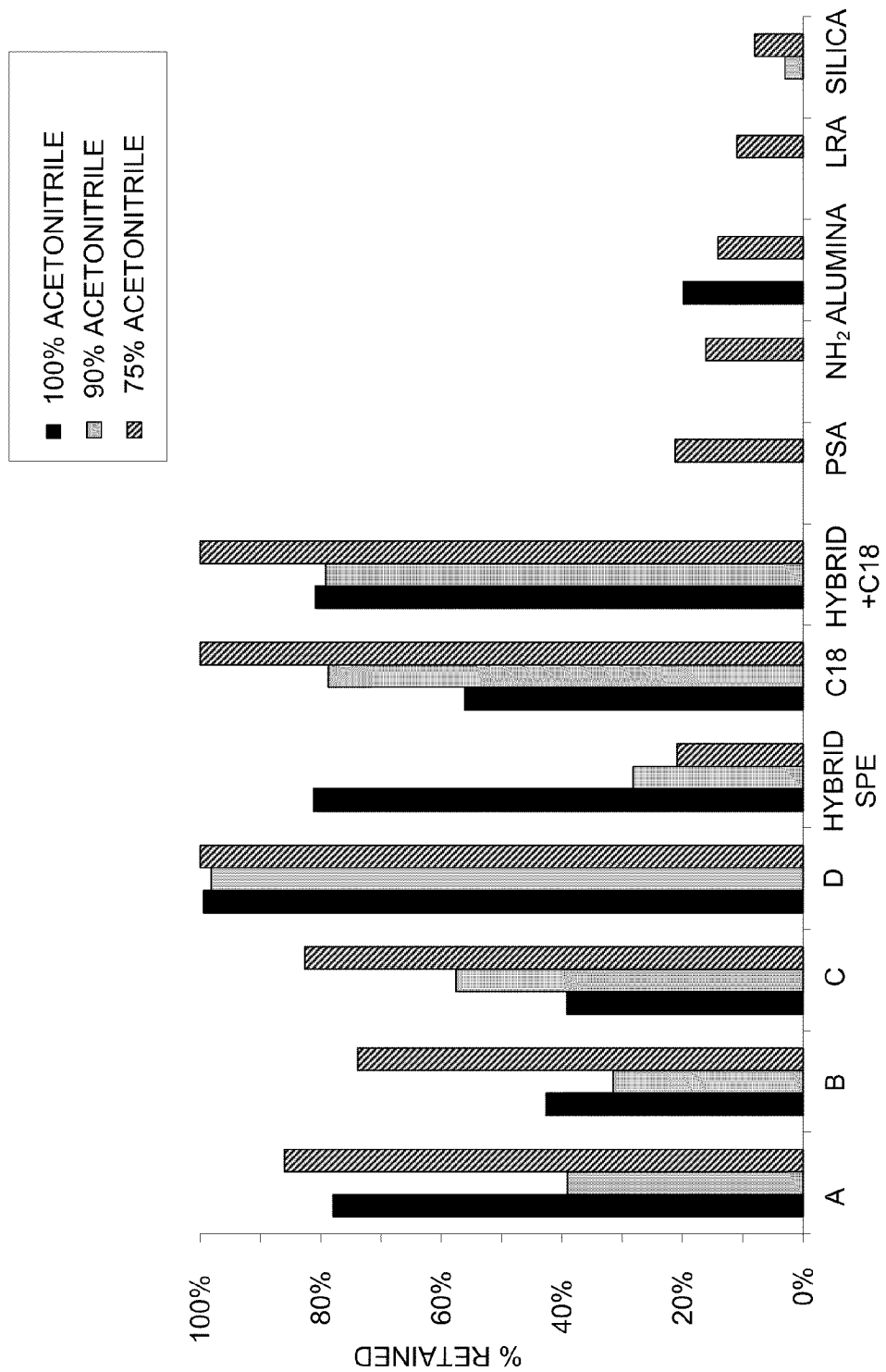
FIG. 37 is a comparison of the amount of diglycerides retained by twelve different exemplary SPE media compositions.
Figure 38:
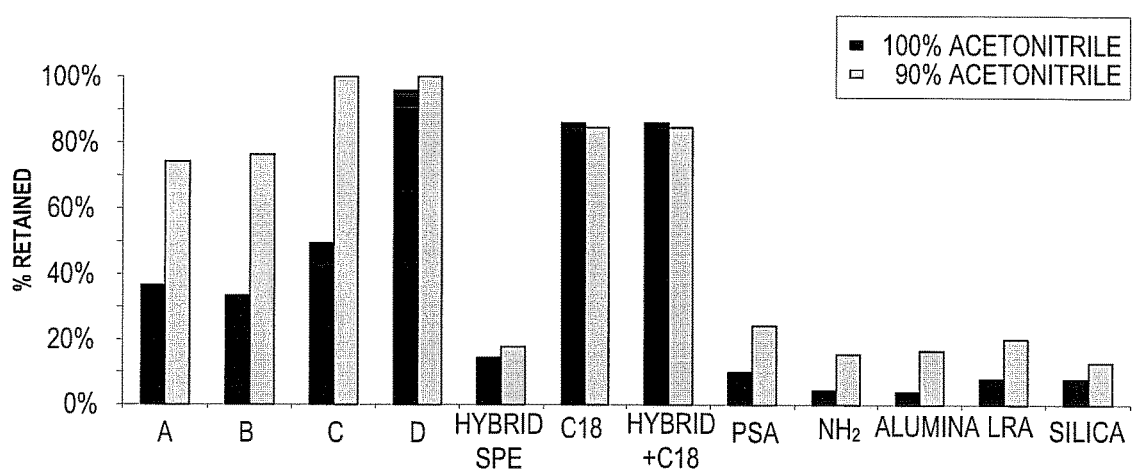
FIG. 38 is a comparison of the amount of triglycerides retained by twelve different exemplary SPE media compositions.

The amount of diglyceride (diolein) removed from the samples by the various adsorbent compositions is summarized in FIG. 37 for the three different sample compositions. Only the hydrophobic zirconia-coated silica (adsorbent D), the octadecyl-coated silica (C18), and the mixture of zirconia-coated silica (Hybrid SPE) and C18 achieved over 50% removal of diglycerides in all sample compositions. The particles of adsorbent D matched or surpassed the efficacy of all other adsorbent compositions for all sample compositions. A similar result was obtained for the removal of triglycerides (triolein) by the various adsorbent compositions, as summarized in FIG. 38 for sample compositions with 90% and 100% acetonitrile solvents.

The results of this experiment demonstrated that adsorbent compositions that included both hydrophobic and transitional metal oxide moieties were most effective at removing monoglycerides from sample solution with acetonitrile solvent concentrations ranging from 75% to 100%. Further, any adsorbent composition containing hydrophobic C8-C18 moieties were most effective at removing both diglycerides and triglycerides from sample solutions with acetonitrile solvent concentrations ranging from 75% to 100%, regardless of the presence or absence of transitional metal oxide moieties on the same particle substrate, or the presence or absence of separate transitional metal oxide-coated silica particles. Overall, the particles having both C18 groups and zirconia bonded independently to the silica substrate surpassed the performance of any of the other adsorbent compositions for all glyceride species and sample compositions tested.

Example 21. The Recovery of Target Analytes after Treatment with Hydrophobic Zirconia-Coated Silica SPE Phase was Evaluated To evaluate the specific affinity of the hydrophobic zirconia-coated silica SPE phase for lipids relative to a variety of target analytes, the following experiment was conducted. Bovine plasma was spiked with 6 different target analyte compounds, listed in Table 18, at a concentration of 25 ng/mL. 25 µL aliquots of the spiked plasma were subjected to protein precipitation by vortexing the aliquots for 30 s with 75 µL of a 1% ammonium formate solution in methanol, followed by centrifugation at 5000 g for 3 minutes. The resulting supernate was transferred into clean sample tubes and subjected to lipid-removal by aspirating and dispensing for a total of twenty times through Hamilton pipette tips packed with 30 mg of the hydrophobic zirconia-coated silica adsorbent similar to the particles described in Example 14. The lipid-free samples were then mixed with an equal volume of 0.1% acetic acid solution in water and readied for LC-MS analysis.

LC-MS analysis of each sample was carried out on a QTrap 3200 mass spectrometer (Applied Biosystems, Foster City, Calif., USA) coupled with an Agilent 1100 LC (Agilent Technologies, Inc., Santa Clara, Calif., USA). 3 µL of each treated sample was injected and separated on a Express RP-Amide column (Supelco, Bellefonte, Pa., USA) that was 5 cm long, had an inner diameter of 2.1 mm, and was packed with 2.7 particles I.D., 5 cm length, and 2.7 µm particles with 100 Å pores. The HPLC phase of the analysis was operated under isocratic conditions with 43% mobile phase B, where the mobile phase A was 0.1% formic acid in water and mobile phase B was 0.1% formic acid in a 50%/50% mixture of methanol and acetonitrile. Flow rate through the HPLC column was 0.2 mL/min and each analyte concentration was monitored using the MRM transitions listed in Table 19. The mass spectrometric parameters were set as follows: CUR (35), IS (5000), TEM (350), GS1 (30), GS2 (30), ihe (ON), CAD (10), and CXP (4).

The amount of each analyte recovered from the protein-precipitated and adsorbent-treated bovine plasma samples spiked with analytes is summarized in Table 19. Overall, the treated bovine plasma samples retained at least 65% of all of the samples spiked into the samples, regardless of whether the sample was neutral or basic.

TABLE 19

Recoveries of Basic and Neutral Compounds from Protein-Precipitated/Adsorbent-Treated Bovine Plasma Samples

| Analyte Compound | Analyte pH | ACD/LogP | MRM transition | Average Recovery (% original) |
| --- | --- | --- | --- | --- |
| Doxepin | Basic | 3.86 | 280/107 | 80.3 |
| Imipramine | Basic | 4.80 | 281/86 | 64.9 |
| Desipramine | Basic | 4.13 | 267/72 | 81.7 |
| Amitriptyline | Basic | 4.92 | 278/233 | 72.8 |
| Trimipramine | Basic | 5.15 | 295/100 | 74.1 |
| Clomipramine | Basic | 5.40 | 315/86 | 69.0 |
| Drospirenone | Neutral | 3.2 | 367/97 | 105.4 |

The results of this experiment demonstrated the hydrophobic zirconia-coated silica SPE media selectively removed lipids from bovine plasma samples and showed little or no affinity for analytes with a variety of compound structures and chemical characteristics.

Example 22. The Preparation of SPE Phase by Linking Zirconia to Silica Substrate Via C3 Linkers was Demonstrated To validate a method of producing a hydrophobic zirconia-coated silica SPE phase that included zirconia linked to silica via C3 linkers, the following experiment was conducted.

20 grams of porous silica particles similar to the large particles used in Example 13 (Davisil Silica, Sigma, St. Louis, USA) were pretreated for bonding by placing the silica particles into a vacuum oven at 120° C. for 16 hours under full vacuum. The dried silica particles were suspended with stirring at room temperature in 200 mL toluene and 20 mL of chloroform in a 4-neck reaction flask with an attached Dean and Stark water trap and condenser, thermocouple, and overhead stirrer. 15 grams of a C3 linking agent, 1,3-bis (trichlorosilyl)propane or $Cl_3Si(CH_2)_3SiCl_3$ (Gelest Inc, Morrisville, Pa., USA) was slowly dropped into the reaction flask through a dropping funnel and the temperature of the reaction mixture was raised to a reflux temperature of 110° C. The reaction mixture was stirred at this temperature for 16 hours. The reaction was then cooled to below 60° C., resulting in silica particles with a single layer of non-cross-linked C3 linkers. The reaction mixture was then filtered, and the filtered particles were sequentially washed with toluene, methanol, methanol/water (50/50), and methanol, and then dried in a vacuum oven at 60° C. overnight.

The dried particles were re-suspended in 300 mL of toluene in the four-neck reaction flask, and heated to reflux temperature until about 50 mL of toluene was distilled into a Dean and Stark trap to eliminate any residual water.

Zirconia was generated and attached to the free ends of the C3 linkers by slowly dropping a 70% solution of zirconium propoxide in propanol (Sigma, St. Louis, USA) into the reaction flask and stirred at a reflux temperature of 110° C. for 16 hours. The resulting zirconia-C3 coated silica particles were sequentially washed with toluene, dichloromethane, methanol, 50% methanol in water, and finally methanol. The rinsed particles were dried in a vacuum oven at 60° C. for 16 hours, and subsequently stored in a desiccator.

The results of this experiment validated a method of producing a hydrophobic zirconia-coated silica SPE phase consisting of zirconia attached to silica supports via C3 linkers.

Example 23. The Preparation of SPE Phase by Linking Zirconia to Silica Substrate Via Multiple-Layered, Cross-Linked C8 Linkers was Demonstrated To validate a method of producing a hydrophobic zirconia-coated silica SPE phase that included zirconia linked to silica via C8 linkers, the following experiment was conducted.

20 grams of porous silica particles similar to the large particles used in Example 13 (Davisil Silica, Sigma, St. Louis, USA) were pretreated for bonding by placing the silica particles into a vacuum oven at 120° C. for 16 hours under full vacuum. The dried silica particles were suspended by stirring at room temperature in 300 mL toluene in a 4-neck reaction flask with an attached Dean and Stark water trap and condenser, thermocouple, and overhead stirrer. 0.5 grams of p-toluenesulfonic acid dissolved in 10 mL of toluene was added to the reaction flask. 21 grams of a C8 linking agent, 1,3-bis(trimethoxysilyl)octyl or $(MeO)_3Si(CH_2)_8Si(MeO)_3$ (Gelest Inc, Morrisville, Pa., USA) was slowly dropped into the reaction flask through a dropping funnel and the temperature of the reaction mixture was raised to a reflux temperature of 110° C. The reaction mixture was stirred at this temperature for 16 hours. The reaction was then cooled down to below 60° C., resulting in silica particles with a single layer of non-cross-linked C8 linkers.

The reaction mixture was then combined with 9-18 mL of a water/n-propanol mixture (1:2 by volume), and then continuously stirred at 90° C. for two hours. The reaction mixture was then heated to a reflux temperature of 110° C. and maintained at this temperature until about 50 mL of toluene has distilled into the Dean and Stark trap in order to eliminate any residual water in the reaction mixture.

Zirconia was then generated and attached to the free ends of the C8 linkers by slowly dropping 40 mL of a 70% solution of zirconium propoxide in propanol (Sigma, St. Louis, USA) into the reaction flask and stirring at 110° C. for 16 hours. The resulting zirconia-C8 coated silica particles were rinsed several times with toluene, and any supernate was decanted. The particles were then sequentially washed with dichloromethane, methanol, 50% methanol in water, and finally methanol. The rinsed particles were dried in a vacuum oven at 60° C. for 16 hours, and subsequently stored in desiccator.

The results of this experiment demonstrated the efficacy of a method of producing a hydrophobic zirconia-coated silica SPE phase consisting of zirconia attached to silica supports via C8 linkers.

Example 24. The Preparation of SPE Phase by Linking Zirconia to Silica Substrate Via Multiple-Layered, Cross-Linked C18 Linkers was Demonstrated To validate a method of producing a hydrophobic zirconia-coated silica SPE phase that included zirconia linked to silica via C18 linkers, the following experiment was conducted.

30 grams of porous silica particles similar to the large particles used in Example 13 (Davisil Silica, Sigma, St. Louis, USA) were pretreated for bonding by placing the silica particles into a vacuum oven at 120° C. for 16 hours under full vacuum. The dried silica particles were suspended in toluene and stirred at room temperature in a 4-neck reaction flask with an attached Dean and Stark water trap and condenser, thermocouple, and overhead stirrer. 17.5 mL of grams of a C18 linking agent, octydecyltrichloromethylsilane (Gelest Inc, Morrisville, Pa., USA) was slowly dropped into the reaction flask through a dropping funnel and the temperature of the reaction mixture was raised to a reflux temperature of 110° C. The reaction mixture was stirred at this temperature overnight. The reaction was then cooled down to below 70° C. and then the particles were filtered, sequentially washed with toluene, methylene chloride, methanol, and toluene. and then aspirated for 10 minutes after the last filtration.

The rinsed particles were re-suspended in toluene in the four-neck reaction flask. The flask was flushed with nitrogen prior to heating the reaction mixture, and a slight positive nitrogen pressure was maintained within the flask for the remaining steps of the reaction. The reaction mixture was heated to a reflux temperature of 110° C. and maintained at this temperature as distilled toluene filled the Dean and Stark trap through two cycles of draining.

The flask was then cooled to a room temperature of 35° C. and zirconia was generated and attached to the free ends of the C18 linkers by slowly dropping a 70% solution of zirconium propoxide in propanol (Sigma, St. Louis, USA) into the reaction flask over a period of one hour and held at this temperature for an additional hour. The reaction mixture was then stirred at 110° C. overnight.

The suspended particles were cooled to 70° C., the liquid upper layer was decanted, and the particles were washed twice with toluene, decanting between washings. The particles were then resuspended in methylene chloride, and then transferred to a filter funnel. In the filter funnel, the particles were sequentially washed with methylene chloride, methanol, 50% methanol in water, and finally methanol. After aspirating the filter funnel for an additional hour, the rinsed particles were dried in a vacuum oven at 80° C. overnight, and subsequently stored in a desiccator.

The results of this experiment demonstrated the efficacy of a method of producing a hydrophobic zirconia-coated silica SPE phase consisting of zirconia attached to silica supports via C18 linkers.

While the invention has been explained in relation to exemplary embodiments, it is to be understood that various modifications thereof will become apparent to those skilled in the art upon reading the description. Therefore, it is to be understood that the invention disclosed herein is intended to cover such modifications as fall within the scope of the appended claims.

What is claimed is:

1. A solid phase extraction (SPE) media for selective removal of lipids from a sample comprising:
   a. a porous silica substrate with any one or more of a particle size ranging from about 10 nm to about 1000 µm, a pore size ranging from about 30 Å to about 1000 Å, and a surface area ranging from about 5 m²/g to about 1000 m²/g;
   b. a hydrophobic alkyl linker having an attached end and a free end opposite the attached end, the attached end covalently bonded to the substrate, wherein the alkyl ranges from $C_3$ to $C_{18}$; and,
   c. zirconia bonded to the porous silica substrate through a bridging bond.

2. The SPE media of claim 1, wherein the sample comprises a biological sample, a food matrix, an environmental sample, a sample from a biotechnology process, or any combination thereof.

3. The SPE media of claim 1, wherein the sample further comprises an acidic analyte, a non-acidic analyte, or a mixture of an acidic analyte and a non-acidic analyte.

4. A solid phase extraction (SPE) media for selective removal of lipids from a sample comprising:
   a. a porous silica substrate with any one or more of a particle size ranging from about 10 nm to about 1000 µm, a pore size ranging from about 30 Å to about 1000 Å, and a surface area ranging from about 5 m²/g to about 1000 m²/g;
   b. a hydrophobic alkyl linker comprising an attached end covalently bonded to the substrate and a free end opposite the attached end, wherein the alkyl ranges from $C_3$ to $C_{18}$; and,
   c. zirconia covalently bonded through a bridging bond coupled to the free end of the hydrophobic alkyl linker.

5. The SPE media of claim 4, wherein the sample comprises a biological sample, a food matrix, an environmental sample, a sample from a biotechnology process, or any combination thereof.

6. The SPE media of claim 4, wherein the sample further comprises an acidic analyte, a non-acidic analyte, or a mixture of an acidic analyte and a non-acidic analyte.

7. A solid phase extraction (SPE) media for selective removal of lipids from a sample, the SPE comprising a mixture of:
   a. a first particle comprising zirconia bonded through a bridging bond to a porous silica substrate having any one or more of a particle size ranging from about 10 nm to about 1000 μm, a pore size ranging from about 30 Å to about 1000 Å, and a surface area ranging from about 5 $m^2/g$ to about 1000 $m^2/g$,
   b. a second particle comprising a hydrophobic alkyl linker ranging from $C_3$ to $C_{18}$ having an attached end and a free end opposite the attached end, the attached end covalently bonded to a second porous silica substrate, the second porous silica substrate having any one or more of a particle size ranging from about 10 nm to about 1000 μm, a pore size ranging from about 30 Å to about 1000 Å, and a surface area ranging from about 5 $m^2/g$ to about 1000 $m^2/g$.

8. The SPE media of claim 7, wherein the sample comprises a biological sample, a food matrix, an environmental sample, a sample from a biotechnology process, or any combination thereof.

9. The SPE media of claim 7, wherein the sample further comprises an acidic analyte, a non-acidic analyte, or a mixture of an acidic analyte and a non-acidic analyte.

* * * * *